US012090167B2

(12) United States Patent
Tahara et al.

(10) Patent No.: US 12,090,167 B2
(45) Date of Patent: Sep. 17, 2024

(54) THERAPEUTIC PHARMACEUTICAL COMPOSITION FOR CANCER INCLUDING miRNA

(71) Applicant: PURMX THERAPEUTICS, INC., Hiroshima (JP)

(72) Inventors: Hidetoshi Tahara, Hiroshima (JP); Masaki Kinehara, Hiroshima (JP); Yuki Yamamoto, Hiroshima (JP)

(73) Assignee: PURMX THERAPEUTICS, INC., Hiroshima (JP)

( * ) Notice: Subject to any disclaimer, the term of this patent is extended or adjusted under 35 U.S.C. 154(b) by 0 days.

(21) Appl. No.: 17/694,982

(22) Filed: Mar. 15, 2022

(65) Prior Publication Data

US 2022/0218733 A1 Jul. 14, 2022

Related U.S. Application Data

(62) Division of application No. 16/760,817, filed as application No. PCT/JP2018/041139 on Nov. 6, 2018, now Pat. No. 11,311,568.

(30) Foreign Application Priority Data

Nov. 9, 2017 (JP) ................................ 2017-216336

(51) Int. Cl.

| | |
|---|---|
| ***C07H 21/04*** | (2006.01) |
| ***A61K 31/713*** | (2006.01) |
| ***A61K 47/42*** | (2017.01) |
| ***A61P 35/00*** | (2006.01) |
| ***C12N 15/113*** | (2010.01) |
| *A61K 45/06* | (2006.01) |

(52) U.S. Cl.

CPC ............ *A61K 31/713* (2013.01); *A61K 47/42* (2013.01); *A61P 35/00* (2018.01); *C12N 15/113* (2013.01); *A61K 45/06* (2013.01); *C12N 2310/141* (2013.01)

(58) Field of Classification Search

CPC ........................ C12N 15/113; C12N 2310/141
See application file for complete search history.

(56) References Cited

U.S. PATENT DOCUMENTS

| | | | | |
|---|---|---|---|---|
| 2009/0202624 | A1 | 8/2009 | Inazawa et al. | |
| 2009/0246875 | A1 | 10/2009 | Yamanaka | C12N 5/0696 435/455 |
| 2010/0227909 | A1 | 9/2010 | Cleary et al. | |
| 2011/0076768 | A1 | 3/2011 | Inazawa et al. | |
| 2012/0157334 | A1 | 6/2012 | Beaudenon-Huibregtse et al. | |
| 2012/0315640 | A1 | 12/2012 | Tahara | |
| 2014/0154303 | A1 | 6/2014 | Tan et al. | |
| 2015/0147384 | A1* | 5/2015 | Koutsopoulos | A61K 9/1075 514/44 R |

FOREIGN PATENT DOCUMENTS

| | | | | |
|---|---|---|---|---|
| CA | 2977624 | A1 | 9/2016 | |
| EP | 2088208 | A1 | 8/2009 | |
| JP | 2008239596 | A | 10/2008 | |
| JP | 2010222338 | A | 10/2010 | |
| JP | 2015519374 | A | 7/2015 | |
| WO | 2010078037 | A2 | 7/2010 | |
| WO | WO 2011/057003 | A2 | 5/2011 | C12N 2310/141 |
| WO | 2012108843 | A1 | 8/2012 | |
| WO | WO 2014/125277 | A1 | 8/2014 | C12N 2310/141 |
| WO | 2015020122 | A1 | 2/2015 | |

OTHER PUBLICATIONS

Krutzfeldt et al. (Nucleic Acids Research, 2007, 35, 9, 2885-2892).*
Zou et al. (The Journal of Biological Chemistry, 287, 6, 4148-4156, 2012).*
Stenvang et al. (Seminars in Cancer Biology, 18, 2, 2008, 89-102).*
Dessie et al. (2018 IEEE 18th International Conference on Bioinformatics and Bioengineering (BIBE), Taichung, Taiwan, 2018, pp. 263-268).*
Veit et al. (Anticancer Research, 35, 1271-1278, 2015).*
Fu Dewang et al: "MiR 631/ZAP70: A novel axis in the migration and invasion of prostate cancer cells" Biochemical and Biophysical Research Communications, 469(3):345-351 2016.
Lisheng Zhang et al: "MicroRNA 657 promotes tumorigenesis in a hepatocellular carcinoma by targeting transducin-like enhancer protein 1 through nuclear factor kappa B pathways" Hepatology, 57(5):1919-1930 2013.
Xi Hao et al: "hsa-miR-631 resensitizes bortezomib resistant multiple myeloma cell lines by inhibiting UbcH10" Oncology Reports, 37(2):961-968 2016.
Godbole et al. (Cancer Biology & Therapy, Sep. 2017, 8, 10, 801-805).
Mohammed et al. (Nature, 2015, 523, 313-317).
International Preliminary Report on Patentability, PCTJP18041139, mailed May 12, 2020, 5 pages.
International Search Report and Written Opinion corresponding to PCTJP18041139, mailed Feb. 5, 2019, 7 pages.
He et al. "MIR-137 silencing of BRD4 suppresses oral squamous cell carcinoma cells proliferation, migration and invasion" Int. J. Clin. Exp. Pathol., 10(1):409-416 2017.
Kinehara et al. "Growth suppression of cancer cells by senescence-inducible miRNA" Tissue Culture Research Communication, 35(1):85 2016.

(Continued)

*Primary Examiner* — Amy Rose Hudson
(74) *Attorney, Agent, or Firm* — Myers Bigel, P.A.

(57) ABSTRACT

The object of the present invention is to find a pharmaceutical having strong cancer therapeutic effect. The present invention provides a pharmaceutical composition for cancer therapy comprising a transcription or processing product of a gene encoding a miRNA, wherein said miRNA is one or more miRNAs selected from the group consisting of miR-3140, miR-137, miR-631, and miR-657, pharmaceutical composition.

10 Claims, 33 Drawing Sheets

Specification includes a Sequence Listing.

(56) References Cited

OTHER PUBLICATIONS

Tonouchi et al. "miR-3140 suppresses tumor cell growth by targeting BRD4 via its coding sequence and downregulates the BRD4-NUT fusion oncoprotein" Scientific Reports, 8:4482, 13 pages 2018.
Krutzfeldt, Jan , et al., "Specificity, duplex degradation and subcellular localization of antagomirs", Nucleic Acids Research, vol. 35, No. 9, 2007, 2885-2892.
Li, Pei , et al., "MicroRNAs in laryngeal cancer: implications for diagnosis, prognosis and therapy", Am J Transl Res, 2016, 1935-1944.
Zhang, Lisheng , et al., "MicroRNA-657 Promotes Tumorigenesis in Hepatocellular Carcinoma by Targeting Transducin-Like Enhancer Protein 1 Through Nuclear Factor Kappa B Pathways", 2013, 1919-1930.
Guo, Jinling , et al., "miR-13 7 suppresses cell growth in ovarian cancer by targeting AEG-1", Biochemical and Biophysical Research Communications 441:357-363 (Oct. 19, 2013).
Liu, Li-Li , et al., "FoxD3-regulated microRNA-137 suppresses tumour growth and metastasis in human hepatocellular carcinoma by targeting AKT2", Oncotarget 5(13):5113-5124 (Jun. 10, 2014).
Peng, Yong , et al., "The role of MicroRNAs in human cancer", Signal Transduction and Targeted Therapy 1, 15004 (Jan. 28, 2016) 9 pages.
Sun, Jie , et al., "MIR-137 inhibits proliferation and angiogenesis of human glioblastoma cells by targeting EZH2", J Neurooncol 122:481-489 (May 5, 2015).
Zhang, Huimin , et al., "MicroRNA-137 is negatively associated with clinical outcome and regulates tumor development through EZH2 in cervical cancer", J Cell Biochem. 119:938-947 (Jul. 5, 2017).
Zhu, Xiaolan , et al., "miR-137 inhibits the proliferation of lung cancer cells by targeting Cdc42 and Cdk6", FEBS Letters 587:73-81 (2013).

* cited by examiner

Effect against mesothelioma cell strains

Effect against mesothelioma cell strains

Effect against uterine sarcoma cell strains miR-3140-3p SIGNIFICANTLY INDUCE APOPTOSIS ON CANCER STEM CELLS Effect against lung cancer strains Antitumor effect of miR-3140-3p in subcutaneous transplantation of malignant pleural mesothelioma cancer cells CHANGE IN TUMOR PROLIFERATION WHEN ADMINISTERING miR-3140 (IMAGING)

CHANGE IN TUMOR PROLIFERATION WHEN ADMINISTERING miRNA (IMAGING AT ENDPOINT)
TRANSPLANTED CELL: HSC-4 (TONGUE CANCER CELL)

IMAGING RESULTS WHEN miR-3140-3p IS ADMINISTERED ONCE

Mouse survival rates when miR-3140-3p is administered once

Imaging results when miR-3140-3p is administered twice

Imaging results when miR-3140-3p is administered three times

Imaging results when miR-3140-3p is administered three times three administrations Calculation of $IC_{50}$ value of miR-3140-3p against EHMES-10

THERAPEUTIC PHARMACEUTICAL COMPOSITION FOR CANCER INCLUDING miRNA

TECHNICAL FIELD

The present invention relates to a pharmaceutical composition for cancer therapy comprising a transcription or processing product of a gene encoding a particular miRNA.

BACKGROUND ART

MicroRNA (hereinafter miRNA) is a functional nucleic acid that is encoded on the genome and ultimately becomes a minuscule RNA of about 20-25 bases long through a multistep production process. miRNA is classified as a functional ncRNA (non-coding RNA), and it is being elucidated that it plays an important role in various biological phenomena (such as regulation of gene expression etc.). Various miRNAs that has come to be well-known thus far including human miRNA are registered in the miRBase (see http://www.mirbase.org/).

miRNA is indicated to be associated with the onset and progression of e.g. cancer, cardiovascular disease, neurodegenerative disease, psychiatric disease, chronic inflammatory disease, and the like. Particularly in recent years, it has been indicated that miRNA is deeply involved in canceration or aging of cells.

For example, Patent Literature 1 describes that miR-22 promotes the aging of cells and suppresses invasion and metastasis of cancer. Moreover, Patent Literature 2 describes that a composition comprising miR-34 may be employed for cancer therapy.

CITATION LIST

[Patent Literature 1] WO2011/078037
[Patent Literature 2] WO2008/137867

SUMMARY OF THE INVENTION

Problems to be Solved by the Invention

The present inventors diligently searched for miRNAs having therapeutic effect against cancer from among a great number of miRNAs.

Means for Solving the Problems

As a result, the present inventors found particular miRNAs that have significantly stronger cancer therapeutic effect than the miRNAs described in prior art, thus arriving at the completion of the present invention.

In other words, the present invention relates to a pharmaceutical composition for cancer therapy comprising a transcription or processing product of a gene encoding a miRNA, characterized in that said miRNA is one or more miRNAs selected from the group consisting of miR-3140, miR-137, miR-631, and miR-657.

One embodiment of the present invention is characterized in that said cancer is a solid cancer.

One embodiment of the present invention is characterized in that said solid cancer is colon cancer, pancreatic cancer, tongue cancer, mesothelioma, uterine sarcoma, osteosarcoma, breast cancer, lung cancer, or head and neck cancer.

One embodiment of the present invention is characterized in that said transcription or processing product of a gene encoding a miRNA is a pri-miRNA, a pre-miRNA, a double-stranded mature-miRNA, a single-strand mature-miRNA expressed from the 5'-end of a pre-miRNA, or a single-strand mature-miRNA expressed from the 3'-end of a pre-miRNA.

One embodiment of the present invention is characterized in that said miRNA is:

(i) a mature-miRNA consisting of a sequence represented by SEQ ID NO. 1, SEQ ID NO. 2, SEQ ID NO. 5, SEQ ID NO. 8, or SEQ ID NO. 11;

(ii) a miRNA having substitution, addition, and/or deletion of 1-5 bases to a mature-miRNA consisting of a sequence represented by SEQ ID NO. 1, SEQ ID NO. 2, SEQ ID NO. 5, SEQ ID NO. 8, or SEQ ID NO. 11, as well as having cancer therapeutic effect; or (iii) a miRNA having 80% or more sequence homology against a mature-miRNA consisting of a sequence represented by SEQ ID NO. 1, SEQ ID NO. 2, SEQ ID NO. 5, SEQ ID NO. 8, or SEQ ID NO. 11, as well as having cancer therapeutic effect.

One embodiment of the present invention is characterized in that said miRNA is chemically modified.

One embodiment of the present invention is characterized in that said chemical modification is one or more chemical modifications selected from the group consisting of LNA-tion, BNA-tion, ENA-ation, 2'-OMe modification, phosphorothioation, S-TuD-ation, morpholino modification, peptide addition, glycosylation, aptamer addition, hydrophobic molecule addition, polymer addition, and addition of unmodified DNA.

One embodiment of the present invention is characterized in that said pharmaceutical composition further comprises a nucleic acid transfection agent.

One embodiment of the present invention is characterized in that said transfection agent is a lipid-based transfection agent, a polymer-based transfection agent, a magnetic particle-based transfection agent, an exosome for nucleic acid delivery, or a viral protein for nucleic acid delivery.

One embodiment of the present invention is characterized in that said transfection agent is a transfection agent comprising a peptide represented by amino acid sequences GGGGDD (G4D2), GGGGGGDD (G6D2), GGGGGGGGDD (G8D2), GGGGGGGGGGDD (G10D2), AAAAAAD (A6D), AAAAAADD (A6D2), AAAAAAK (A6K), AAAAAAKK (A6K2), VVVVVVD (V6D), VVVVVVDD (V6D2), VVVVVVK (V6K), VVVVVVKK (V6K2), LLLLLLD (L6D), LLLLLLDD (L6D2), LLLLLLK (L6K), or LLLLLLKK (L6K2).

One embodiment of the present invention is characterized in that the pharmaceutical composition of the present invention is for topical administration.

One embodiment of the present invention is characterized in that the pharmaceutical composition of the present invention is used in combination with other anticancer agents.

One embodiment of the present invention is characterized in that said other anticancer agents are one or more anticancer agents selected from the group consisting of an alkylating agent, a platinum preparation, a metabolism antagonist, a topoisomerase inhibitor, a microtubular inhibitor, an anti-cancerous antibiotic, a molecular target drug, a hormone preparation, an immunomodulation drug, an interferon, an interleukin, a plant-derived anticancer agent, and a BRM preparation.

Another embodiment of the present invention relates to the use of a transcription or processing product of a gene encoding a miRNA for manufacturing a pharmaceutical composition for cancer therapy, characterized in that said miRNA is one or more miRNAs selected from the group consisting of miR-3140, miR-137, miR-631, and miR-657.

Another embodiment of the present invention relates to a cancer therapy method comprising a step of applying to a cancer patient a therapeutically effective amount of an anti-cancerous pharmaceutical composition comprising a transcription or processing product of a gene encoding a miRNA, characterized in that said miRNA is one or more miRNAs selected from the group consisting of miR-3140, miR-137, miR-631, and miR-657.

An invention of any combination of one or more characteristics listed above is encompassed by the scope of the present invention.

DESCRIPTION OF EMBODIMENTS

Figure 1:
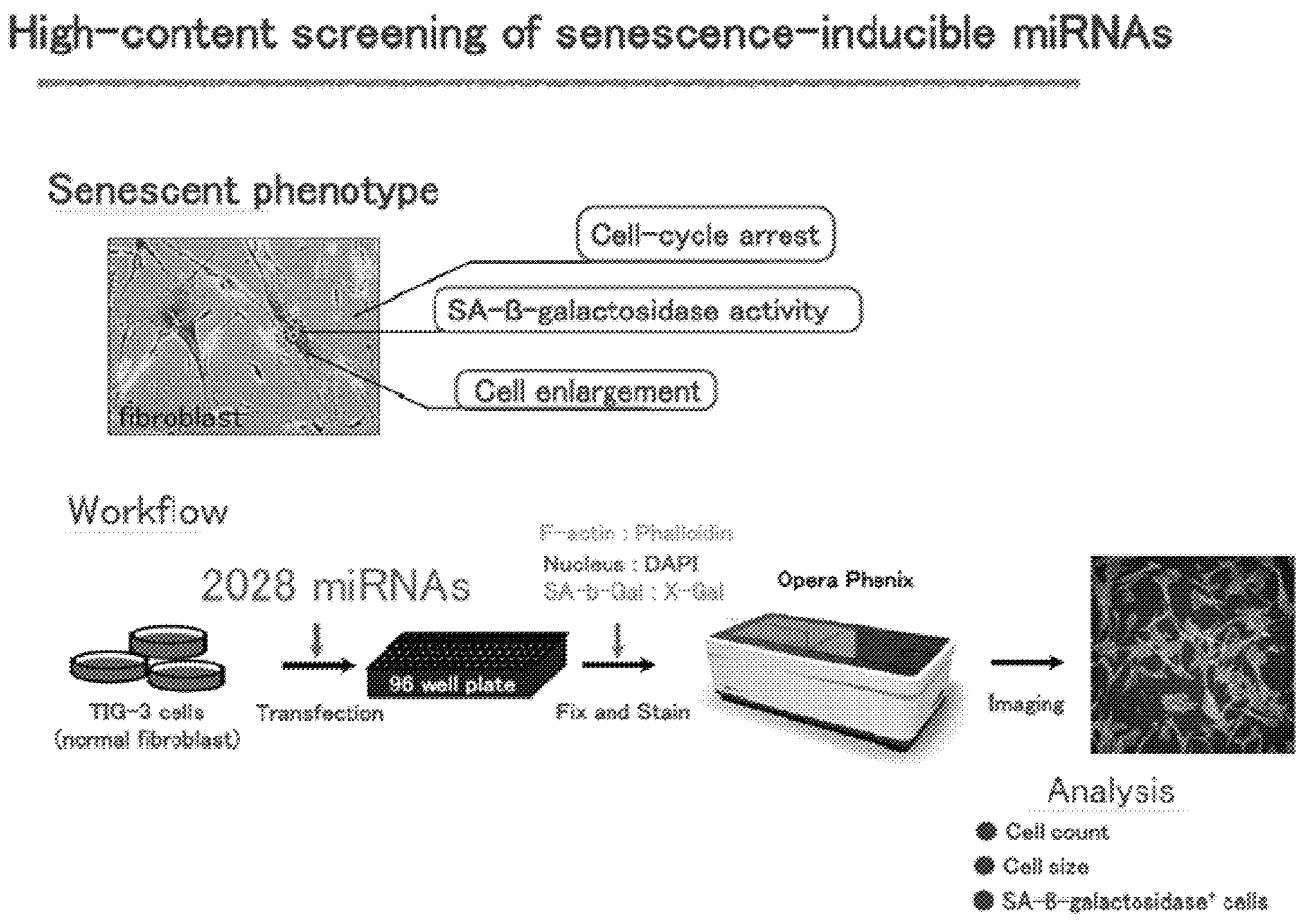
FIG. 1 describes the flow of miRNA screening in the Examples.

The present invention relates to a pharmaceutical composition for cancer therapy comprising a transcription or processing product of a gene encoding a miRNA (micro-RNA). A general miRNA is biosynthesized via a continuous process. The primary transcription product of a gene encoding a miRNA is called a Primary miRNA transcript (pri-miRNA), and generally has a stem-loop hairpin structure. Pri-miRNA is cleaved by a microprocessor complex, takes a hairpin form by Drosha which is a RNase III-series enzyme, and precursor miRNA (pre-miRNA) which is an intermediate precursor of about 70 bases is produced. The pre-miRNA is then transported from the nucleus to the cytoplasm. In the cytoplasm, it is further cleaved by Dicer which is another RNase III enzyme, and a double-stranded mature miRNA is produced. In general, among the two strands, "-5p" is added to that expressed from the 5'-end of the precursor and "-3p" is added to that expressed from the 3'-end, and are represented as "hsa-miR-21-5p" and "hsa-miR-21-3p". Note that in principle, well-known miRNAs are registered in the miRBase (http://www.mirbase.org/).

Note that only one of the strands in the mature miRNA may exert the desired effect, or each of the stands may exert the desired effect, or the desired effect may be exerted in the double-stranded state. Moreover, the desired effect may also be exerted in pri-miRNA state or pre-miRNA state.

The nucleic acid comprised in the composition of the present invention may be a transcription or processing product of a gene encoding one or more miRNAs selected from the group consisting of miR-3140, miR-137, miR-631, and miR-657, and may also be a variant or a modification that retains the function of the aforementioned nucleic acid.

The sequence of the transcription or processing product of the gene encoding miR-3140 used in one embodiment of the present invention is as follows.

TABLE 1

| Name | Sequence |
|---|---|
| Mature-miRNA (miR-3140-5p) | ACCUGAAUUACCAAAAGCUUU (SEQ ID NO. 1) |
| Mature-miRNA (miR-3140-3p) | AGCUUUUGGGAAUUCAGGUAGU (SEQ ID NO. 2) |

TABLE 1-continued

| Name | Sequence |
|---|---|
| Pre-miRNA | CCUCUUGAGGUACCUGAAUUACCAAAAGCUUUAUGU AUUCUGAAGUUAUUGAAAAUAAGAGCUUUUGGGAAU UCAGGUAGUUCAGGAGUG (SEQ ID NO. 3) |

Note that the sequence of the intron region encoding the pri-miRNA of miR-3140 is shown in SEQ ID NO. 4.

The sequence of the transcription or processing product of the gene encoding miR-137 used in one embodiment of the present invention is as follows.

TABLE 2

| Name | Sequence |
|---|---|
| Mature-miRNA (miR-137-3p) | UUAUUGCUUAAGAAUACGCGUAG (SEQ ID NO. 5) |
| Pre-miRNA | GGUCCUCUGACUCUCUUCGGUGACGGGUAUUCUUGGGU GGAUAAUACGGAUUACGUUGUUAUUGCUUAAGAAUACG CGUAGUCGAGGAGAGUACCAGCGGCA (SEQ ID NO. 6) |

Note that the sequence of the intron region encoding the pri-miRNA of miR-137 is shown in SEQ ID NO. 7.

The sequence of the transcription or processing product of the gene encoding miR-631 used in one embodiment of the present invention is as follows.

TABLE 3

| Name | Sequence |
|---|---|
| Mature-miRNA (miR-631-5p) | AGACCUGGCCCAGACCUCAGC (SEQ ID NO. 8) |
| Pre-miRNA | GUGGGGAGCCUGGUUAGACCUGGCCCAGACCUCAGCUA CACAAGCUGAUGGACUGAGUCAGGGGCCACACUCUCC (SEQ ID NO. 9) |

Note that the sequence of the intron region encoding the pri-miRNA of miR-631 is shown in SEQ ID NO. 10.

The sequence of the transcription or processing product of the gene encoding miR-657 used in one embodiment of the present invention is as follows.

TABLE 4

| Name | Sequence |
|---|---|
| Mature-miRNA (miR-657-3p) | GGCAGGUUCUCACCCUCUCUAGG (SEQ ID NO. 11) |
| Pre-miRNA | GUGUAGUAGAGCUAGGAGGAGAGGGUCCUGGAGAAGCG UGGACCGGUCCGGGUGGGUUCCGGCAGGUUCUCACCCU CUCUAGGCCCCAUUCUCCUCUG (SEQ ID NO. 12) |

Note that the sequence of the intron region encoding the pri-miRNA of miR-657 is shown in SEQ ID NO. 13.

The nucleic acid comprised in the composition of the present invention may be e.g. a nucleic acid having substitution, addition, and/or deletion of 1, 2, 3, 4, or 5 bases to a mature-miRNA consisting of a sequence represented by SEQ ID NO. 1, SEQ ID NO. 2, SEQ ID NO. 5, SEQ ID NO. 8, or SEQ ID NO. 11, as well as having the effect of inhibiting cancer cell growth. The substitution of a base to the mature-miRNA may be e.g. a conservative substitution of RNA known in the art.

Moreover, the nucleic acid comprised in the composition of the present invention may be e.g. a nucleic acid having 80% or more (preferably, 85% or more, 90% or more, 95% or more) sequence homology (or sequence identity) to a mature-miRNA consisting of a sequence represented by SEQ ID NO. 1, SEQ ID NO. 2, SEQ ID NO. 5, SEQ ID NO. 8, or SEQ ID NO. 11, as well as having the effect of inhibiting cancer cell growth.

A mature-miRNA consisting of a sequence represented by SEQ ID NO. 1, SEQ ID NO. 2, SEQ ID NO. 5, SEQ ID NO. 8, or SEQ ID NO. 11 can be easily manufactured by a RNA synthesis equipment commonly used in the art, and a nucleic acid having a particular base substituted, added, and/or deleted can similarly be easily manufactured. Moreover, numerous companies accept commissioned synthesis of nucleic acids, and it is also easy to obtain RNA of the desired sequence from such companies. Accordingly, those skilled in the art will be able to investigate the nature and function of a variant or modification of a mature-miRNA consisting of a sequence represented by SEQ ID NO. 1, SEQ ID NO. 2, SEQ ID NO. 5, SEQ ID NO. 8, or SEQ ID NO. 11 by conventional means without excessive burden.

Moreover, the nucleic acid comprised in the composition of the present invention may have received a chemical modification well-known in the art with the purpose of improving the stability or specificity etc. of RNA. Chemical modification that may be employed in the present invention may be e.g. LNA (Locked Nucleic Acid)-tion, BNA (Bridged Nucleic Acid)-tion, ENA (2'-O,4'-C-Ethylene-bridged Nucleic Acids)-tion, 2'-OMe modification, phosphorothioation (S-ation), S-TuD (Synthetic Tough Decoy)-ation, morpholino modification, peptide addition, glycosylation, aptamer addition, hydrophobic molecule addition such as cholesterol, polymer addition such as PEG, or addition of unmodified DNA. These chemical modifications can be performed by a well-known means known in the art.

The present invention can be employed for various cancer therapies, e.g. it can be favorably employed for solid cancer. More preferably, the subject of the present invention may be colon cancer, pancreatic cancer, tongue cancer, mesothelioma, uterine sarcoma, osteosarcoma, breast cancer, lung cancer, or head and neck cancer.

In order to appropriately introduce the present invention to cancer cells, the composition of the present invention may further comprise a nucleic acid transfection agent. Examples of the nucleic acid transfection agent that may be employed for the present invention include a lipid-based transfection agent, a polymer-based transfection agent, a magnetic particle-based transfection agent, an exosome for nucleic acid delivery, or a viral protein for nucleic acid delivery.

An example of the lipid-based transfection agent includes a cationic lipid. With a cationic lipid, nucleic acid-cationic lipid complexes are incorporated into cells via endocytosis and released into the cytoplasm, thus introducing the nucleic acid into cells (lipofection). Specifically, e.g. various commercially available reagents for lipofection may be employed.

An example of the polymer-based transfection agent includes e.g. a cationic polymer. When a cationic polymer comes in contact with a nucleic acid, a nucleic acid-polymer complex is formed, and the complex attaches to the cell membrane via electrostatic interaction and is incorporated into the cell via endocytosis. Specifically, a cationic peptide and a derivative thereof (such as polylysine and polyornithine), a linear or branched-chain synthetic polymer (such as polybrene and polyethyleneimine), a polysaccharide-based introduction molecule (such as cyclodextrin and chitosan), a natural polymer (such as histone and collagen), as well as active and inactive dendrimers, and the like may be employed. Moreover, transfection agents employed in so-called nanoDDS, such as a transfection agent that employs a block copolymer that forms micellar nanoparticles and a transfection agent that employs carbon nanohorns can also be used for the present invention.

An example of the magnetic particle-based transfection agent includes a transfection agent that employs magnetic particles coated with cation molecules. A magnetic particle-based transfection agent carries out transfection by adhering the nucleic acid on the surface of magnetic particles, and then magnetically introducing the aforementioned magnetic particles into cells. Specifically, for example various commercially available magnetic particles for transfection may be employed.

Moreover, nucleic acid transfection agent that employs a generally available exosome or a transfection agent that utilizes viral proteins such as adenovirus can also be used for the present invention.

Further, in the present invention, a transfection agent comprising a peptide represented by amino acid sequences GGGGDD (G4D2) (SEQ ID NO. 14), GGGGGGDD (G6D2) (SEQ ID NO. 15), GGGGGGGGDD (G8D2) (SEQ ID NO. 16), GGGGGGGGGGDD (G10D2) (SEQ ID NO. 17), AAAAAAD (A6D) (SEQ ID NO. 18), AAAAAADD (A6D2) (SEQ ID NO. 19), AAAAAAK (A6K) (SEQ ID NO. 20), AAAAAAKK (A6K2) (SEQ ID NO. 21), VVVVVVD (V6D) (SEQ ID NO. 22), VVVVVVDD (V6D2) (SEQ ID NO. 23), VVVVVVK (V6K) (SEQ ID NO. 24), VVVVVVKK (V6K2) (SEQ ID NO. 25), LLLLLLD (L6D) (SEQ ID NO. 26), LLLLLLDD (L6D2) (SEQ ID NO. 27), LLLLLLK (L6K) (SEQ ID NO. 28), or LLLLLLKK (L6K2) (SEQ ID NO. 29) may be employed, and in particular AAAAAAD (A6D) or AAAAAAK (A6K) can be favorably employed. The effects of these peptides as transfection agents are disclosed in e.g. WO2010/024262.

The pharmaceutical composition for cancer therapy of the present invention can be used in combination with other anticancer agents well-known in the art. Other anticancer agents used in combination are not limited, and e.g. one or more anticancer agents selected from the group consisting of an alkylating agent, a platinum preparation, a metabolism antagonist, a topoisomerase inhibitor, a microtubular inhibitor, an anti-cancerous antibiotic, a molecular target drug, a hormone preparation, an immunomodulation drug, an interferon, an interleukin, a plant-derived anticancer agent, and a BRM preparation can be employed.

The aspects of combination use of the pharmaceutical composition for cancer therapy of the present invention and the other anticancer agents well-known in the art are not limited, and can be carried out by those skilled in the art (such as a physician) in various aspects according to the type of cancer to be the subject or therapeutic stage and the like. The pharmaceutical composition for cancer therapy of the present invention and the other anticancer agents may be administered to the subject at the same or different times. The pharmaceutical composition for cancer therapy of the present invention and the other anticancer agents may also be prepared as formulations comprising each and administered to a subject. The pharmaceutical composition for cancer therapy of the present invention and the other anticancer agents may also be prepared as a kit that separately comprises each.

An aspect of administering the pharmaceutical composition for cancer therapy of the present invention and the other anticancer agents at the same time may be e.g. an aspect of administering to a subject a formulation comprising the pharmaceutical composition for cancer therapy of the present invention and the other anticancer agents.

In the present invention, an aspect of administering the pharmaceutical composition for cancer therapy of the present invention and the other anticancer agents at different times may be e.g. an aspect of administering each of the pharmaceutical composition for cancer therapy of the present invention and the other anticancer agents with staggered time, and e.g. an aspect of administering the pharmaceutical composition for cancer therapy of the present invention and the other anticancer agents from different administration routes.

The administration route of the pharmaceutical composition for cancer therapy of the present invention is not limited, and may be systemic administration or topical administration. Administration routes can include e.g. oral administration including sublingual administration, parenteral administration such as inhalation administration, direct administration to target tissue by catheter or injection, intravenous administration including infusion, transdermal administration by patches and the like, suppositories, or administration by forced enteral nutrition employing a nasogastric tube, a nasointestinal tube, a gastrostomy tube, or enterostomy tube, and the like.

The dosage form of the pharmaceutical composition for cancer therapy of the present invention may be appropriately determined according to said administration route, and can include, but is not limited to, injections, infusions, tablets, capsules, fine granules, powders, liquids, solutions dissolved in syrups etc., patches, suppositories, and the like.

The subject for administering the pharmaceutical composition of the present invention is not limited, and e.g. the present invention can be employed for mammals (humans, pigs, cows, monkeys, baboons, dogs, cats, rats, mice, and the like). However, when it is unfavorable, humans can be removed from subjects.

The administration method of the pharmaceutical composition of the present invention to a subject (administration route, dosage, administration frequency per day, administration timing, and the like) is not limited, and can be appropriately determined by those skilled in the art (such as a physician) according to the health state of the subject, the extent of disease, the type of agent used in combination, and the like.

The terms used herein, except for those that are particularly defined, are employed for describing particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

The present invention will now be described in further detail with reference to Examples. However, the present invention can be embodied by various aspects, shall not be construed as being limited to the Examples described herein.

EXAMPLES

Experiment 1: Screening of miRNA with High Cell Aging Inducibility (1) Transfection of all miRNAs into TIG-3 Cells (FIG. 1)

A total of 2028 types of miRNAs (mirVana; Ambion) were transfected into TIG-3 cells (human fibroblasts) with an auto dispenser Bravo (Agilent). Transfection was carried out by the following protocol.

1: To 70 μL of serum free medium (SFM) was added 0.35 μL of RNAiMAX (Invitrogen).

2: The solution from 1 was added to a 96-well plate (μ-plate; ibidi) with Bravo.

3: To 2 was added 0.7 μL of miRNA (Stock Conc. 2 μM) with Bravo, and this was mixed by pipetting.

4: This was incubated at room temperature for 20 minutes.

5: A cell suspension diluted to $3.5\times10^4$ cells/mL was dispensed at 70 μL each with Bravo.

6: This was incubated at 37° C. under 5% $CO_2$ condition.

(2-1) Staining of Transfected Cells

Setting the day of transfection as Day 0, staining was performed five days later in order to evaluate the number of cells and cell size. The protocol therefor is shown below.

1: Washing twice with PBS (−) was carried out.

2: 3.7% formalin solution was added, and this was incubated at room temperature for 10 minutes to fix the cells.

3: Washing twice with PBS (−) was carried out.

4: Staining solution was added, and this was incubated at room temperature for 30 minutes for staining.

5: Washing three times with PBS (−) was carried out.

6: The plate after completion of staining was subjected to full visual field photographing with an automatic photographing equipment Operetta (Perkin Elmer).

7: The photographs taken were subjected to quantitative analysis with an image analysis software Columbus (Perkin Elmer).

TABLE 5

Composition of the staining solution

| Reagent name | 1 mL | final Conc. |
|---|---|---|
| PBS (—) | 1 mL | |
| Triton X-100 (NACALAI TESQUE) | 1 μL | 0.1% |
| BSA (Sigma-Aldrich) | 10 mg | 1% |
| Alexa Fluor ® 488 Phalloidin (Thermo Fisher Scientific) | 4 μL | 0.8 Unit |
| DAPI (1 mg/mL) (DOJINDO) | 0.1 μL | 0.1 μg/mL |

(2-2) SA-β-Galactosidase Assay of Transfected Cells

Setting the day of transfection as Day 0, SA-β-galactosidase assay was performed on Day 7. The operating protocol is shown below.

1: Washing twice with PBS (−) was carried out.

2: 2% formalin solution was added, and this was incubated at room temperature for 5 minutes to fix the cells.

3: Washing twice with PBS (−) was carried out.

4: β-Gal staining solution was prepared at the time of use and added to the wells.

5: This was incubated at 37° C. for 12-16 hours.

6: The plate after completion of staining was photographed with an automatic photographing equipment Opera (Perkin Elmer).

TABLE 6

Composition of β-Gal staining solution

| Reagent name | stock conc. | final conc. |
|---|---|---|
| citric acid/Na phosphate buffer *[1] | 0.2M | 40 mM |
| $K_4\{e(CN)_6\}H_2O$ | 100 mM | 5 mM |
| $K_3\{Fe(CN)_6\}$ | 100 mM | 5 mM |
| NaCl | 5M | 150 mM |
| $MgCl_2$•$6H_2O$ | 1M | 2 mM |
| $H_2O$ | | |
| X-gal *[2] | 20 mg/mL | 1 mg/mL |

*[1] Prepared so that pH is 6.0.

*[2] X-gal (5-Bromo-4-chloro-3-indoyl-β-D-Galactopyranoside: Wako) was prepared at the time of use with N.N-dimethyl formamide.

Figure 2:
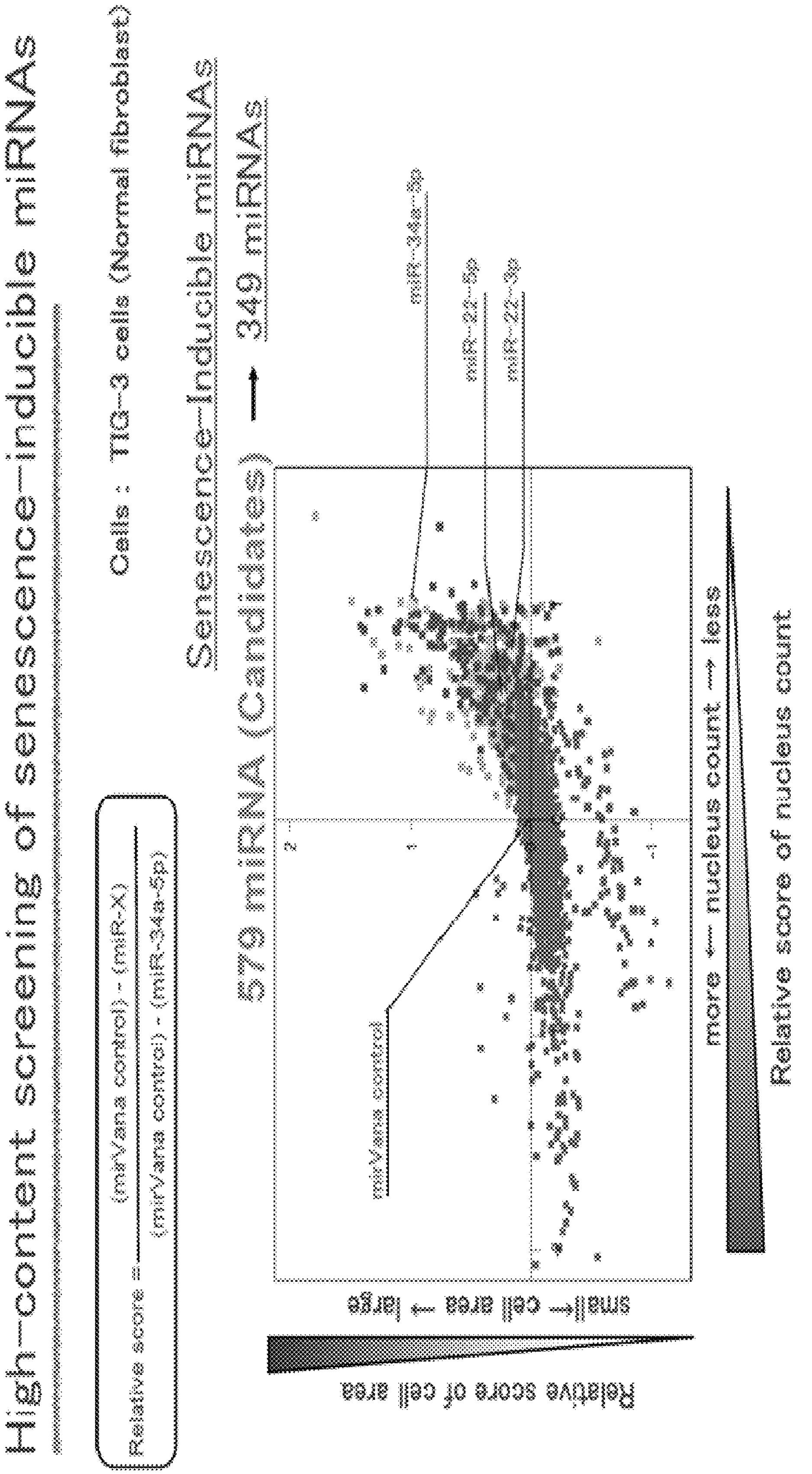
FIG. 2 describes the flow of miRNA screening in the Examples.

(3) Analysis of the Screening Result (FIG. 2)

Each of the values of the number of cells and cell size obtained were scored with the numeric values of random sequence miRNA which is the negative control and the numeric values of miR-34a-Sp which is the positive control. The scoring method is shown below.

Within Each Plate

1: The value of the positive control was subtracted from the value of the negative control.

2: The value of each miRNA was subtracted from the value of the negative control.

3: The value from 2 was divided by the value from 1 to obtain a score value.

4: A scatter diagram was drawn by taking the score value of the number of cells on the horizontal axis and the score value of the cell size on the vertical axis.

5: 579 types of miRNAs where at least one of the two showed a score value higher than the score values of miR-22-3p and miR-22-5p were identified as aging induction miRNA candidates.

6: Out of the 579 types of candidates, 349 types of miRNAs that induced activation of β-galactosidase which is a cell aging marker were identified as aging induction miRNAs.

Experiment 2: Further Screening Employing Cancer Cell Strains

The 349 types of aging induction miRNA (mirVana; Ambion) obtained from screening were transfected into various cancer cell strains (large intestine cancer cell strain HCT116 (p53 wildtype and p53 deletion), pancreatic cancer cell strains BxPC-3 and CFPAC-1, and tongue cancer cell strain HSC-4) with an auto dispenser Bravo (Agilent).

Transfection was carried out with the following protocol.

1: To 70 μL of serum free medium (SFM) was added 0.35 μL of RNAiMAX (Invitrogen).

2: The solution from 1 was added to a 96-well plate (μ-plate; ibidi) with Bravo.

3: To 2 was added 0.7 μL of miRNA (Stock Conc. 200 nM) with Bravo, and this was mixed by pipetting.

4: This was incubated at room temperature for 20 minutes.

5: A cell suspension diluted to $3.5\times10^4$ cells/mL was dispensed at 70 μL each with Bravo.

6: This was incubated at 37° C. under 5% $CO_2$ condition.

Setting the day of transfection as Day 0, on Day 5 the cell survival rate was evaluated with PrestoBlue (Invitrogen). The operating protocol is shown below.

1. The medium was exchanged to a medium comprising PrestoBlue diluted 20-folds, and this was incubated at 37° C. for 1 hour.

2. The fluorescence value (Ex/Em=560 nm/590 nm) was measured with Enspire (Perkin Elmer).
3. The cell survival rate was determined by setting the fluorescence value obtained from the well with only the reagent as the background.

The above protocol was carried out for each cancer cell strain (large intestine cancer cell strain HCT116 (p53 wild-type and p53 deletion), pancreatic cancer cell strains BxPC-3 and CFPAC-1, and tongue cancer cell strain HSC-4), and the miRNAs that suppress cell proliferation more significantly than miR-34a-5p were sorted.

Figure 3:
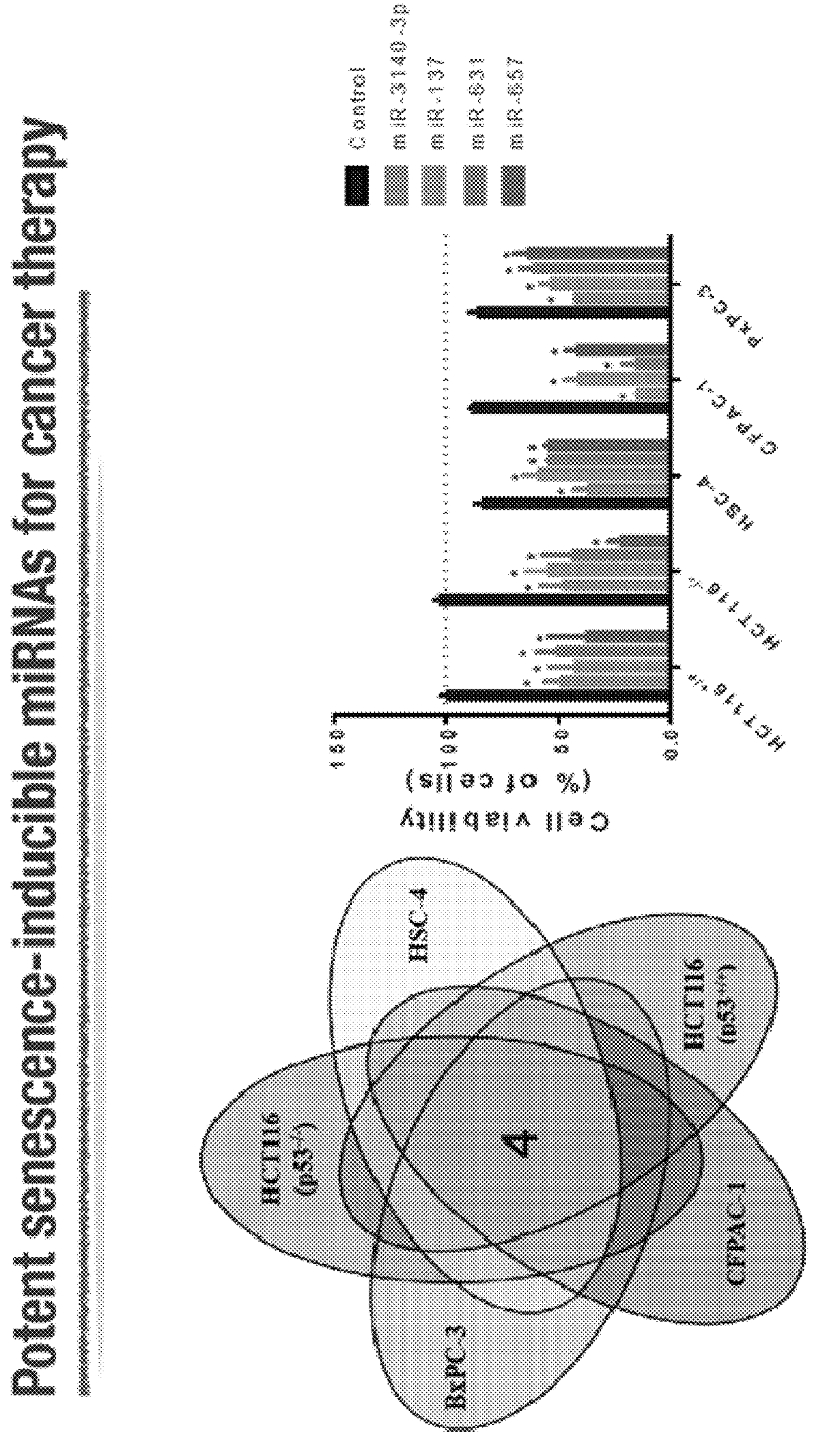
FIG. 3 shows four miRNAs that show growth inhibition effect against numerous types of cancer cells sorted in miRNA screening.

As a result of sorting the miRNAs that suppress cell proliferation more significantly than miR-34-5p commonly in all cell strains, four miRNAs (miR-137-3p, miR-631-5p, miR-657-3p, and miR-3140-3p) were found (FIG. 3).

Experiment 3. Confirmation of Cell Growth Inhibition Effect Employing Various Cancer Cell Strains (1) Tongue Cancer Cell Strain (HSC-4 and OSC-19) (FIG. 4)

Four miRNAs (miR-137-3p, miR-631-5p, miR-657-3p, and miR-3140-3p) were transfected into tongue cancer cell strains (HSC-4 and OSC-19), and cell proliferation was observed. Transfection was carried out with the following protocol.

1: To a 35 mm dish were added 500 μL of serum free medium (SFM) and 5 μL of RNAiMAX (Invitrogen).
2: To the solution from 1 was added 1 μL each of nucleic acids (Control, miR-137-3p, miR-631-5p, miR-657-3p, miR-3140-3p, and a mixture of equal amounts of the four miRNAs (final concentration 10 nM).
3: This was incubated at room temperature for 20 minutes.
4: A cell suspension diluted to $6.7\times10^4$ cells/mL was added to the 35 mm dish at 1.5 mL each.
5: This was incubated at 37° C. under 5% $CO_2$ condition.
6: The cells were counted five days after transfection.

Figure 4:
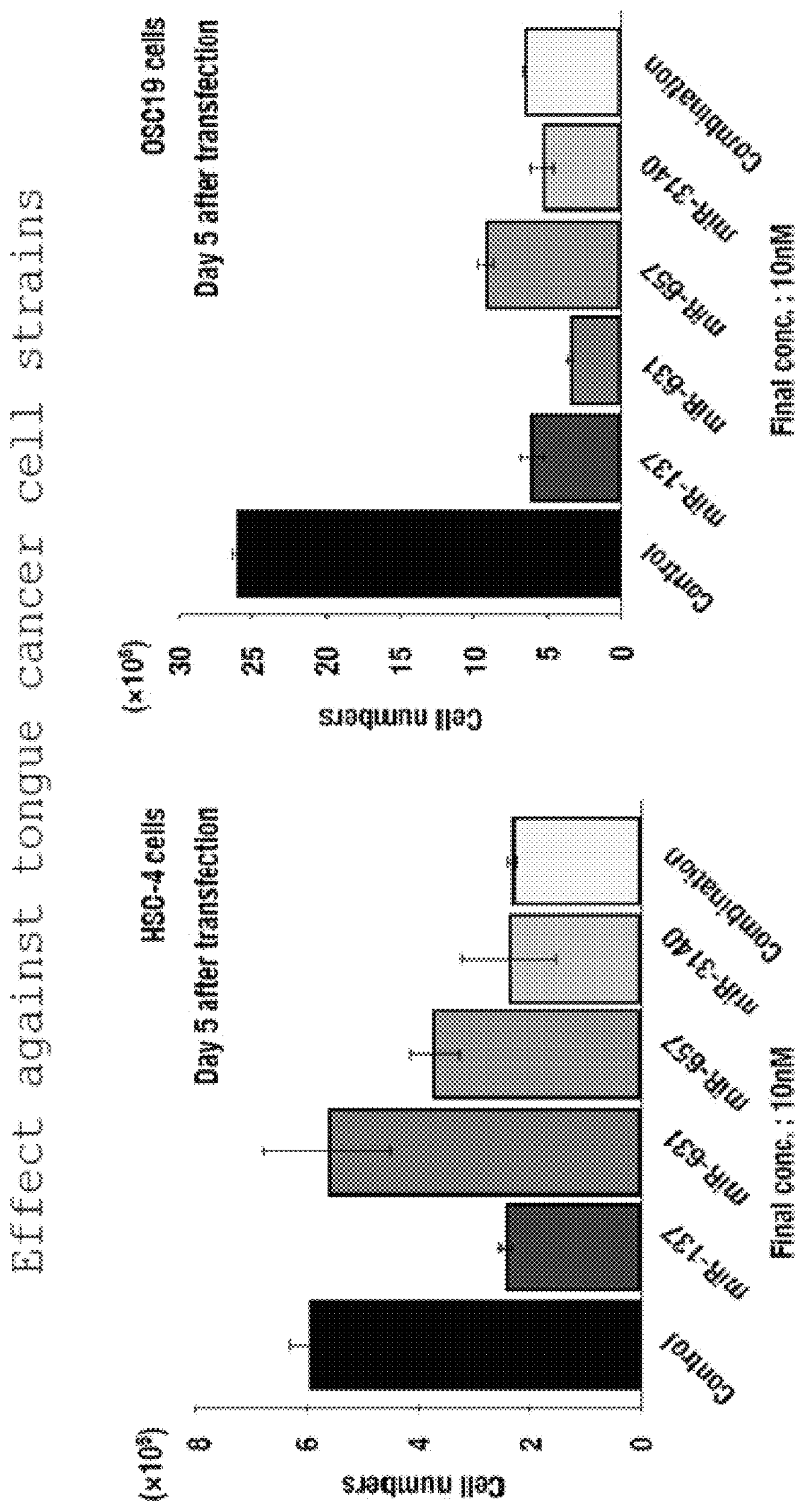
FIG. 4 shows the effect of the miRNA of the present invention on tongue cancer cell strains (HSC-4 cells and OSC19 cells).

As shown in FIG. 4, the four miRNAs showed cell growth inhibition effect in both tongue cancer cell strains.

Figure 5:
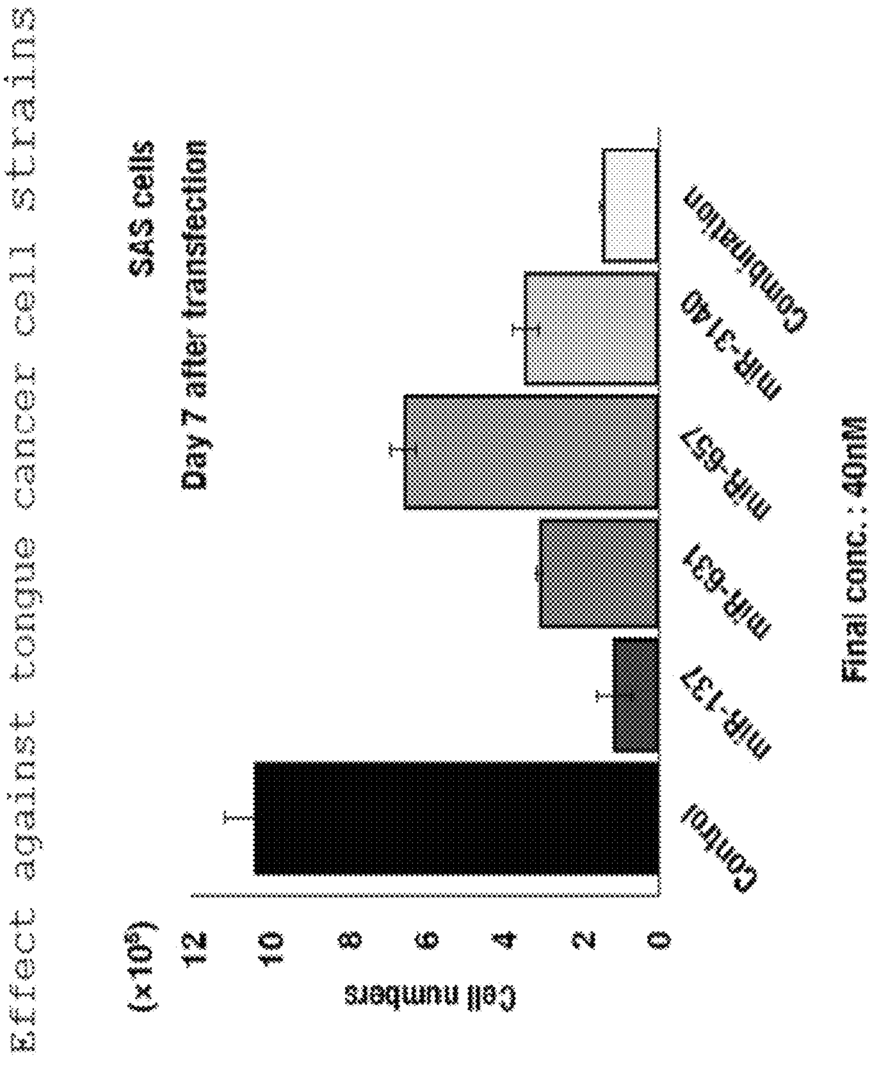
FIG. 5 shows the effect of the miRNA of the present invention on tongue cancer cell strain (SAS cells).
Figure 6:
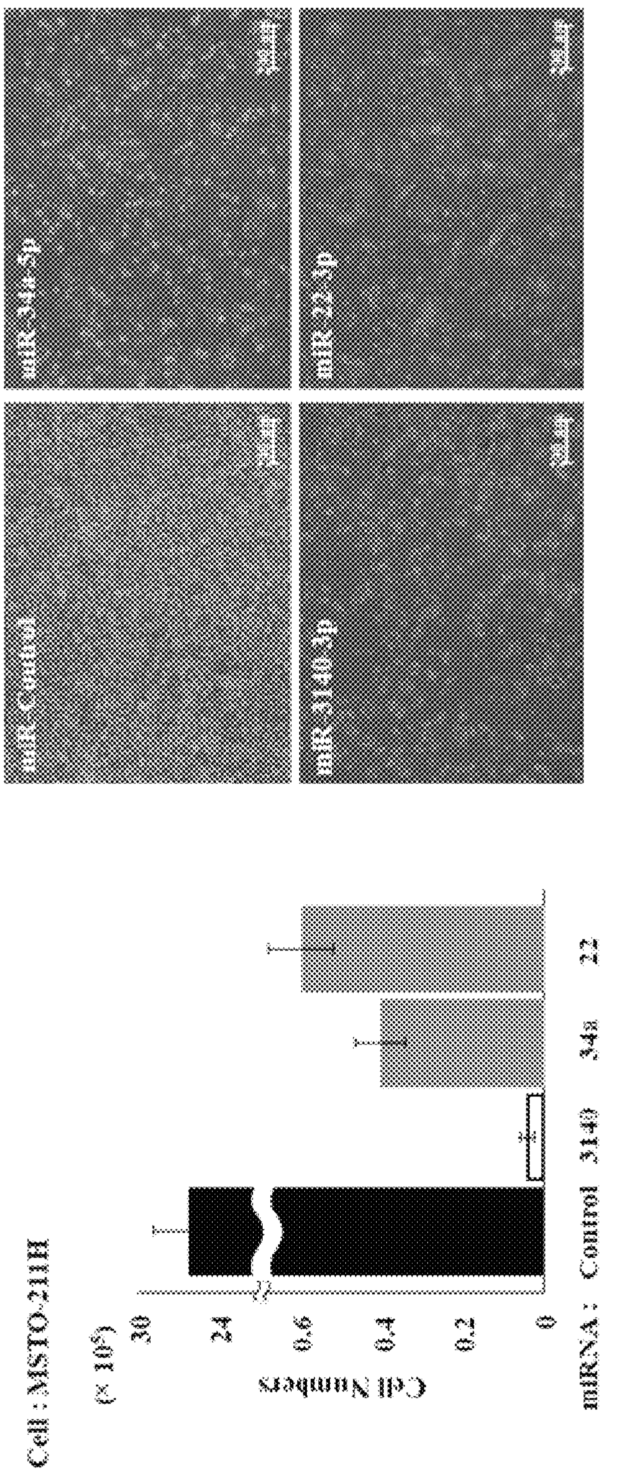
FIG. 6 shows the effect of the miRNA of the present invention on mesothelioma cell strain (MSTO-211H cells).
Figure 7:
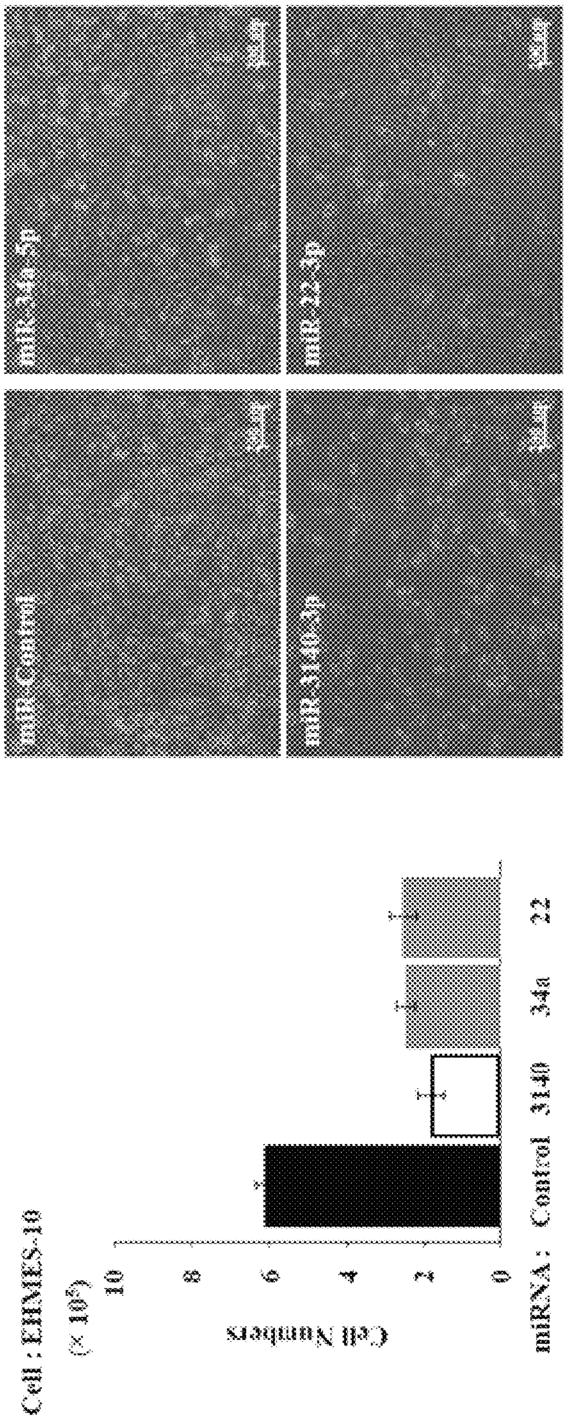
FIG. 7 shows the effect of the miRNA of the present invention on mesothelioma cell strain (EHMES-10 cells).
Figure 8:
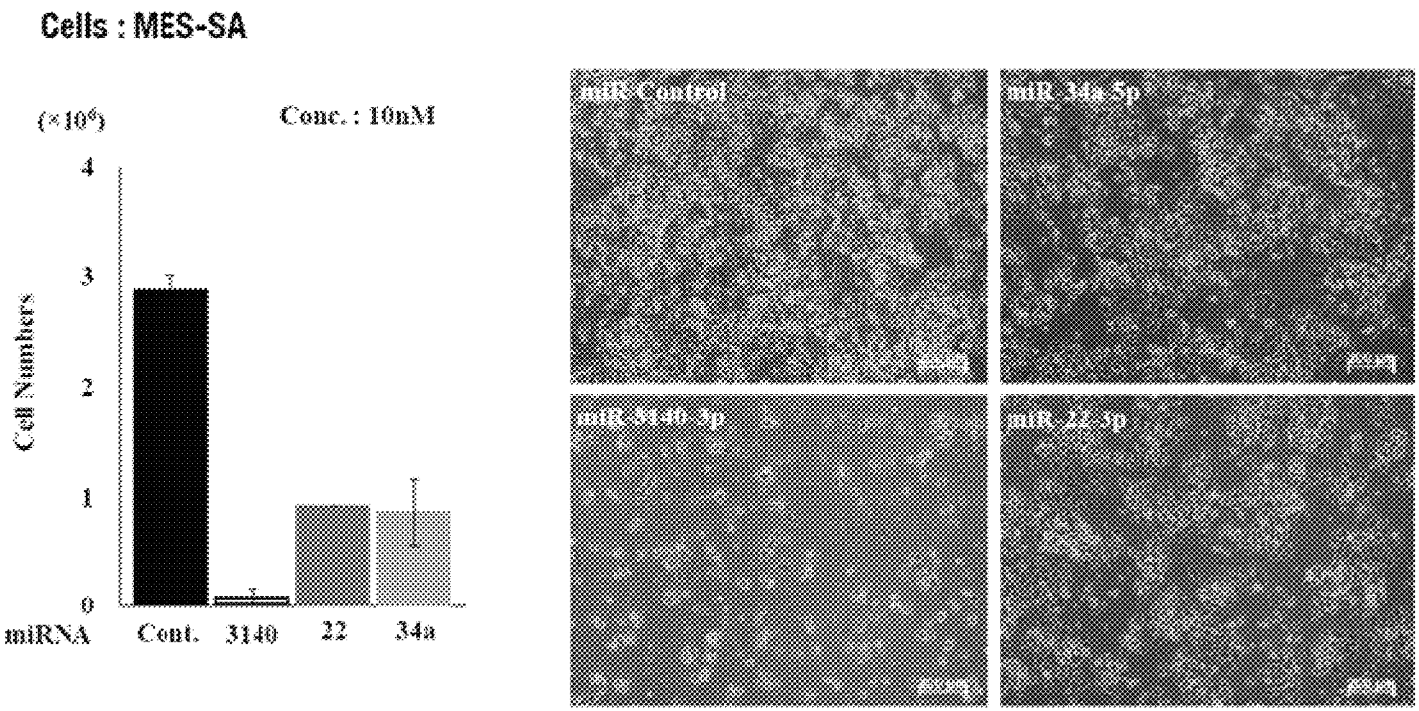
FIG. 8 shows the effect of the miRNA of the present invention on uterine sarcoma cell strain (MES-SA cell).
Figure 9:
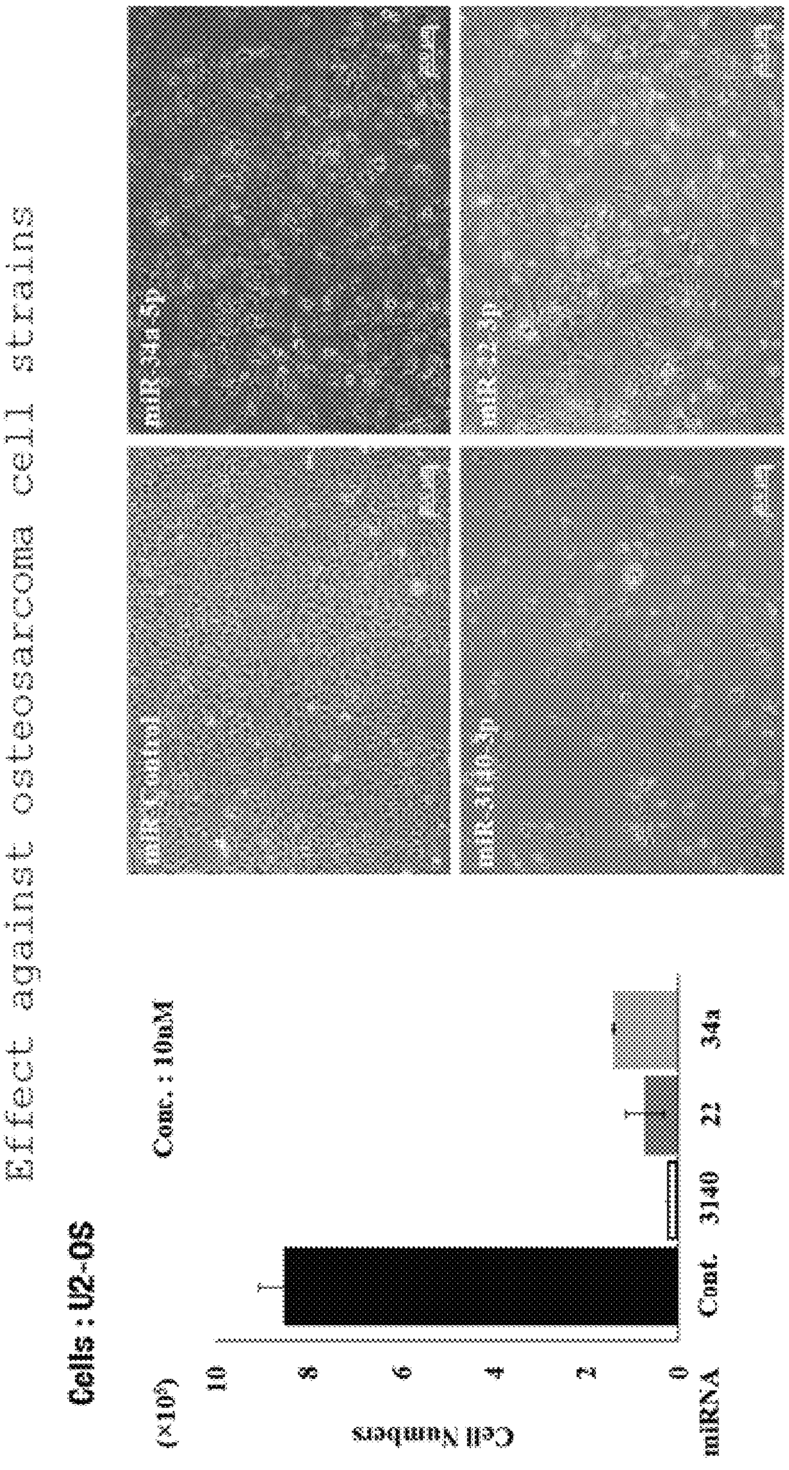
FIG. 9 shows the effect of the miRNA of the present invention on osteosarcoma cell strain (U2-OS cells).

(2) Tongue Cancer Cell Strain (SAS) (FIG. 5)

Four miRNAs (miR-137-3p, miR-631-5p, miR-657-3p, and miR-3140-3p) were transfected into a tongue cancer cell strain (SAS), and cell proliferation was observed. Transfection was carried out with the following protocol.

1: To a 35 mm dish were added 500 μL of serum free medium (SFM) and 5 μL of RNAiMAX (Invitrogen).
2: To the solution from 1 was added 4 μL each of the miRNA solutions (see Table 7) (final concentration 10 nM).
3: This was incubated at room temperature for 20 minutes.
4: 1.5 mL of a cell suspension diluted to $6.7\times10^4$ cells/mL was added to the 35 mm dish.
5: This was incubated at 37° C. under 5% $CO_2$ condition.
6: Operations from 1-3 were repeated two days after transfection.
7: The solutions prepared in 6 were each added to the dish cultured in 5.
8: The cells were counted seven days after the first transfection.

As shown in FIG. 5, any of the four miRNAs showed cell growth inhibition effect against tongue cancer cell strain SAS.

[Table 7]

TABLE 7

| | miRNA dosage | | | | | |
|---|---|---|---|---|---|---|
| Stock(20 μM) | Control | miR-137-3p | miR-631-5p | miR-657-3p | miR-3140-3p | Combination |
| miR Control | 4 μL | 3 μL | 3 μL | 3 μL | 3 μL | — |
| miR-137-3p | — | 1 μL | — | — | — | 1 μL |
| miR-631-5p | — | — | 1 μL | — | — | 1 μL |
| miR-657-3p | — | — | — | 1 μL | — | 1 μL |
| miR-3140-3p | — | — | — | — | 1 μL | 1 μL |
| Total | 4 μL | 4 μL | 4 μL | 4 μL | 4 μL | 4 μL |

(3) Malignant Pleural Mesothelioma Cell Strains, Uterine Sarcoma Cell Strain, and Osteosarcoma Cell Strain (FIGS. 6-9)

Among the above four miRNAs, miR-3140-3p which had particularly high cell growth inhibition effect was transfected in each of malignant pleural mesothelioma cell strains (MSTO-211H and EHMES-10), uterine sarcoma cell strain (MES-SA), and osteosarcoma cell strain (U2-OS), and cell proliferation was observed. As comparison subjects, miR-22-3p and miR-34a-5p which showed cell growth inhibition effect in prior research were employed. Transfection was carried out with the following protocol.

1: To a 35 mm dish were added 500 μL of serum free medium (SFM) and 5 μL of RNAiMAX (Invitrogen).
2: To the solution from 1 was added 1 μL each of miR-Control or miR-3140-3p, miR-22-3p, and miR-34a-Sp (stock conc. 20 μM) (final concentration 10 nM).
3: This was incubated at room temperature for 20 minutes.
4: 1.5 mL of a cell suspension diluted to $6.7\times10^4$ cells/mL was added to the 35 mm dish.
5: This was incubated at 37° C. under 5% $CO_2$ condition.
6: The cells were counted four days after transfection.

As shown in FIGS. 6-9, in any of the cell strains, miR-3140-3p showed extremely high cell growth inhibition effect compared to prior art miR-22-3p and miR-34a-5p.

Figure 10:
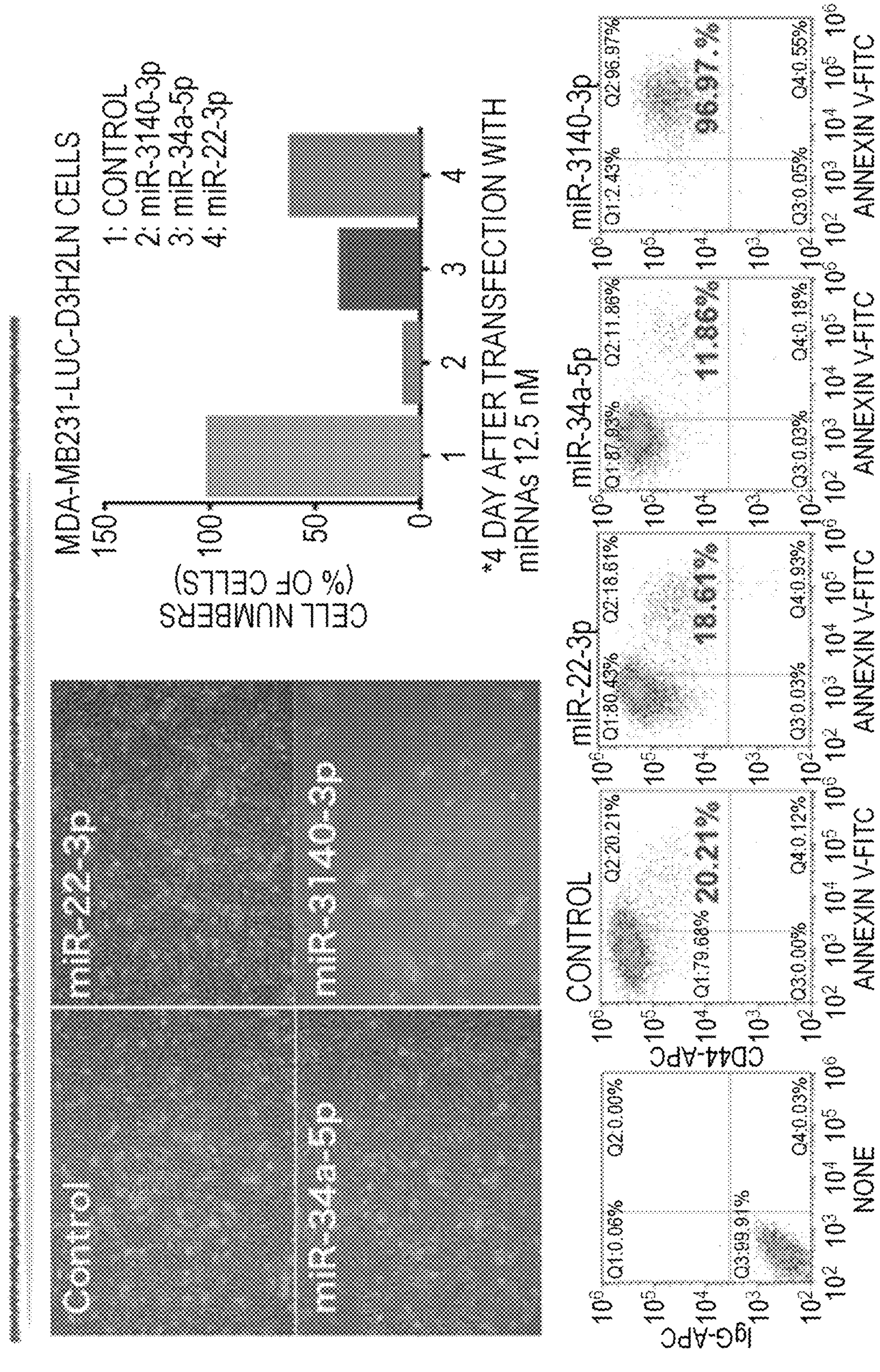
FIG. 10 shows the effect of the miRNA of the present invention on cancer stem cell strains (MDA-MB231-luc-D3H2LN cells).

(4) Breast Cancer Stem Cell Strain (MDA-MB231-Luc-D3H2LN Cells) (FIG. 10)

miR-3140-3p was transfected in a highly metastatic cancer cell strain of breast cancer (MDA-MB231-luc-D3H2LN cells), and cell proliferation was observed. As comparison subjects, miR-22-3p and miR-34a-5p which showed cell growth inhibition effect in prior research were employed. Transfection was carried out with the following protocol.

1: To a 35 mm dish were added 500 μL of serum free medium (SFM) and 5 μL of RNAiMAX (Invitrogen).
2: To the solution from 1 was added 12.5 μL each of miR-Control or miR-3140-3p, miR-22-3p, and miR-34a-5p (stock conc. 2 μM) (final concentration 12.5 nM).

3: This was incubated at room temperature for 20 minutes.

4: 1.5 mL of a cell suspension diluted to $6.7\times10^4$ cells/mL was added to the 35 mm dish.

5: This was incubated at 37° C. under 5% $CO_2$ condition.

6: The cells were counted four days after transfection.

Moreover, by the protocol below, the expression of apoptosis marker Annexin V in breast cancer cells transfected with miR-3140-3p was analyzed.

1: Transfection of miR-3140-3p was performed with a protocol similar to that described above.

2: Six days after transfection, cells were recovered together with the supernatant.

3: Samples for FACS were prepared according to the protocol of the Annexin V assay kit.

4: Cells stained by Annexin V-FITC were stained with an antibody against cancer stem cell marker CD44 (eBioScience).

5: The prepared samples were analyzed with Cell Sorter (SONY).

As shown in FIG. 10 top, miR-3140-3p showed extremely high cell growth inhibition effect against breast cancer stem cell strain (MDA-MB231-luc-D3H2LN cells).

Moreover, as shown in FIG. 10 bottom, in breast cancer stem cells at six days after transfection of miR-3140-3p, apoptosis marker Annexin V was highly positive (96.97%). In other words, it was shown that miR-3140-3p significantly induces apoptosis against cancer stem cells.

Figure 11:
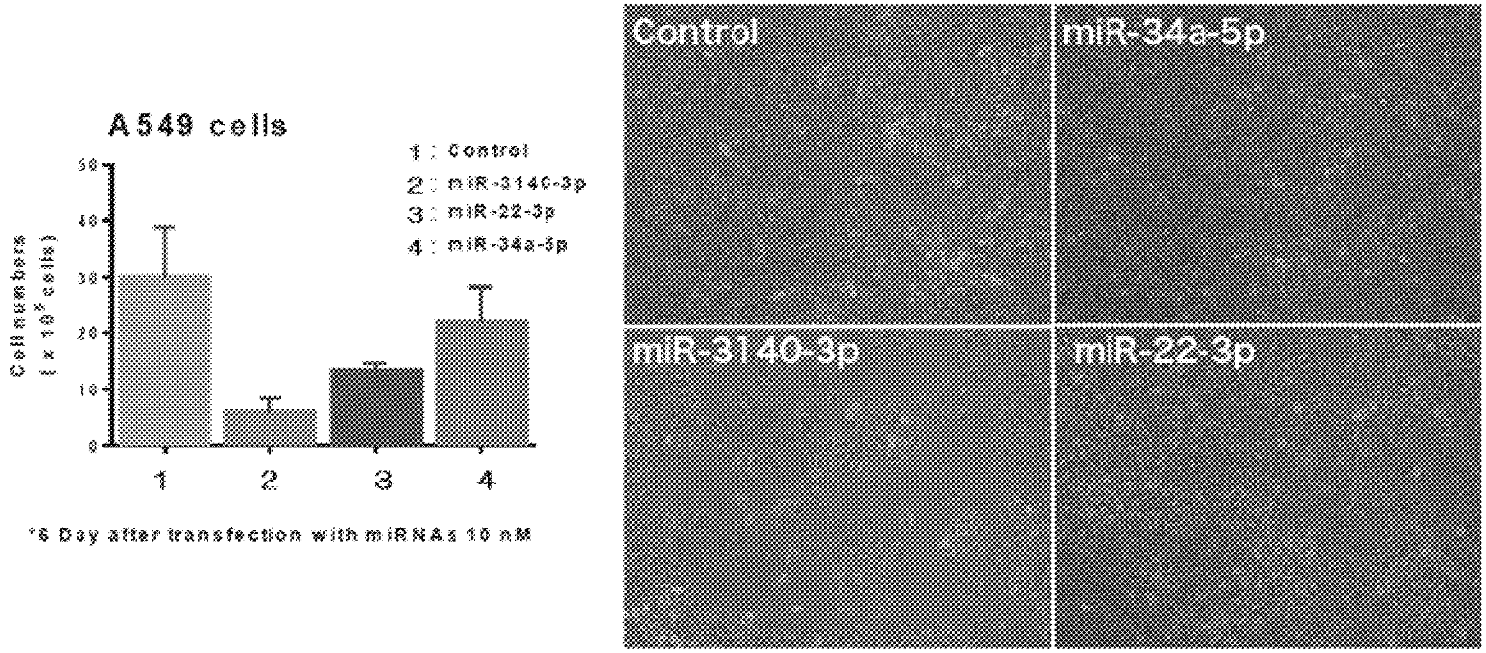
FIG. 11 shows the effect of the miRNA of the present invention on lung cancer cell strain (A549 cells).

(5) Lung Cancer Cell Strain (A549) (FIG. 11)

miR-3140-3p was transfected into lung cancer cell strain (A549), and cell proliferation was observed. As comparison subjects, miR-22-3p and miR-34a-5p which showed cell growth inhibition effect in prior research were employed. Transfection was carried out with the following protocol.

1: To a 35 mm dish were added 500 μL of serum free medium (SFM) and 5 L of RNAiMAX (Invitrogen).

2: To the solution from 1 was added 1 μL each of miR-Control or miR-3140-3p, miR-22-3p, and miR-34a-Sp (stock conc. 20 μM) (final concentration 10.0 nM).

3: This was incubated at room temperature for 20 minutes.

4: 1.5 mL of a cell suspension diluted to $6.7\times10^4$ cells/mL was added to the 35 mm dish.

5: This was incubated at 37° C. under 5% $CO_2$ condition.

6: The cells were counted six days after transfection.

As shown in FIG. 11, miR-3140-3p showed extremely high cell growth inhibition effect against lung cancer cell strain (A549).

Figure 12:
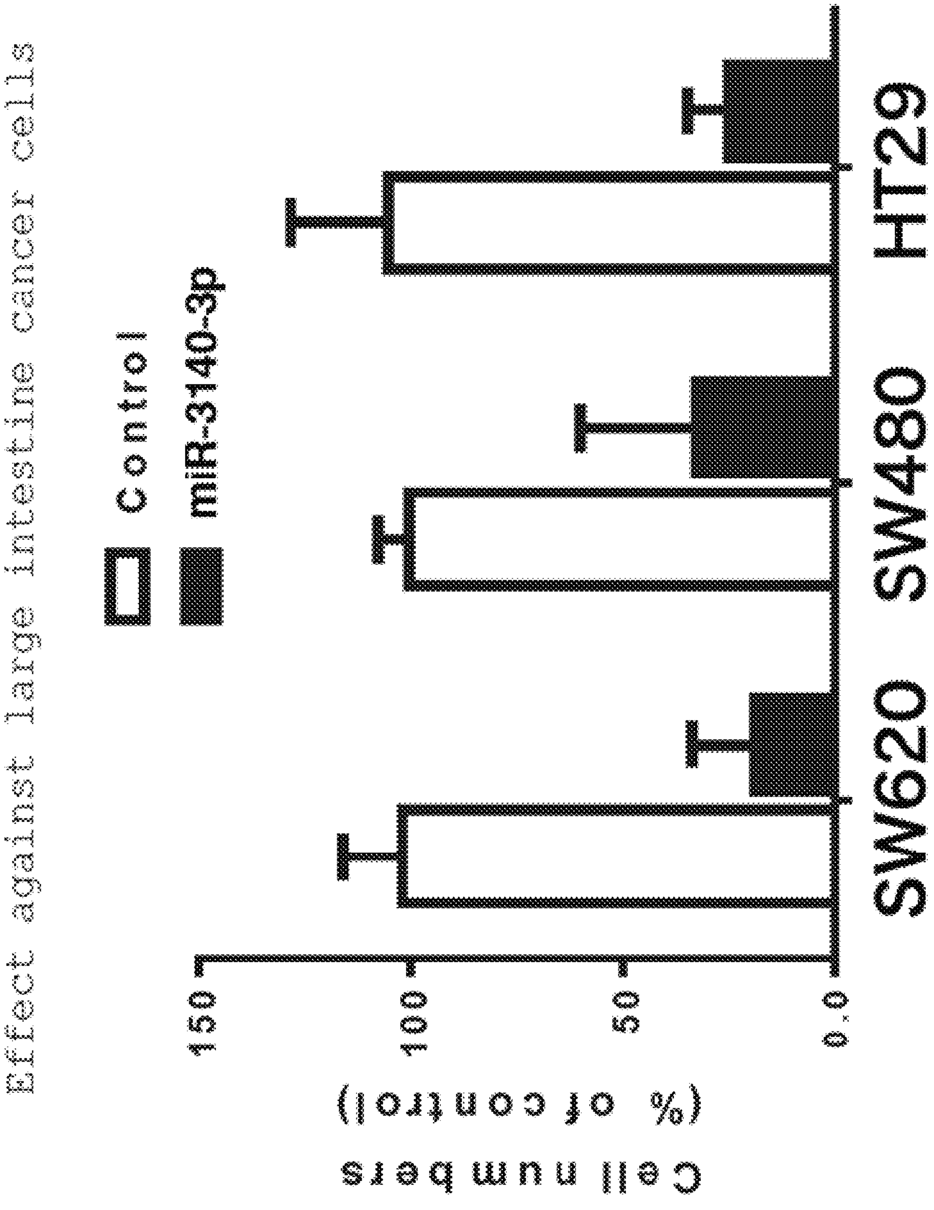
FIG. 12 shows the effect of the miRNA of the present invention on large intestine cancer cell strains (SW620 cells, SW480 cells, and HT29 cells).

(6) Large Intestine Cancer Cell Strains (SW620, SW480, and HT29) (FIG. 12)

miR-3140-3p was transfected into large intestine cancer cell strains (SW620, SW480, and HT29), and cell proliferation was observed. Transfection was carried out with the following protocol.

1: To a 35 mm dish were added 500 μL of serum free medium (SFM) and 5 μL of RNAiMAX (Invitrogen).

2: To the solution from 1 was added 12.5 μL each of miR-Control or miR-3140-3p, miR-22-3p, and miR-34a-Sp (stock conc. 2 μM) (final concentration 10.0 nM).

3: This was incubated at room temperature for 20 minutes.

4: 1.5 mL of a cell suspension diluted to $6.7\times10^4$ cells/mL was added to the 35 mm dish.

5: This was incubated at 37° C. under 5% $CO_2$ condition.

6: The cells were counted seven days after transfection.

Results are shown in FIG. 12. Setting the number of control introduction cells as 100%, the survival rate of cells in which miR-3140-3p was introduced was shown in %. As shown in FIG. 12, miR-3140-3p showed extremely high cell growth inhibition effect against any of the large intestine cancer cell strains.

Figure 13:
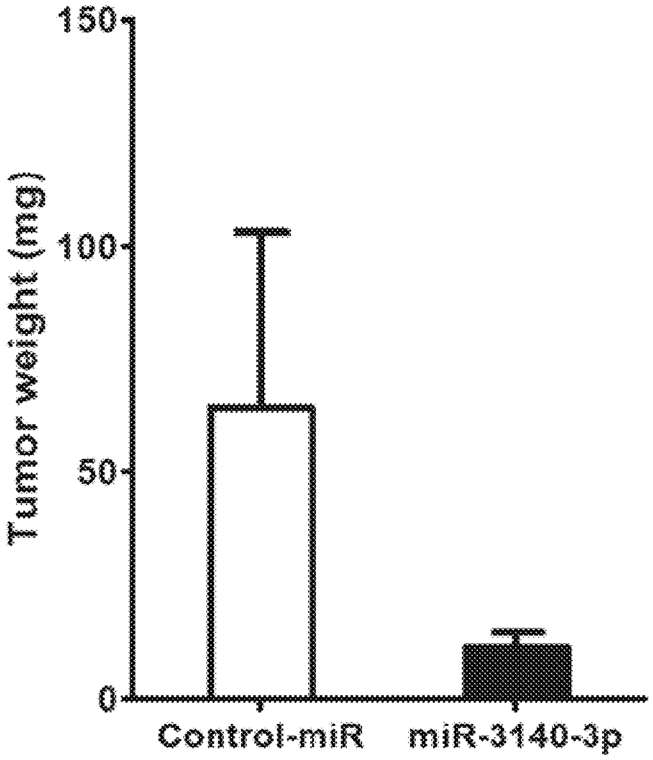
FIG. 13 shows the cancer therapeutic effect of the miRNA of the present invention in vivo.

Experiment 4. Antitumor Effect of the miRNA of the Present Invention In Vivo (Malignant Pleural Mesothelioma Cells) (FIG. 13)

In order to verify the antitumor effect of the miRNA of the present invention in vivo, experiments was performed with laboratory animals transplanted with malignant pleural mesothelioma cells.

(1) Preparation of Cells

Malignant pleural mesothelioma cells MSTO-211H cells were used.

1: The cells on the dish were washed twice with PBS (−).

2: The cells were detached with trypsin.

3: This was suspended in a medium, and cells were counted.

4: Centrifugation at a condition of 1000 rpm for 3 min was performed to pellet down.

5: The cells were resuspended in PBS (−) in order to obtain $2.0\times10^7$ cells/mL.

(2) Cell Transplantation to Mice

Six weeks-old C-B-17/Icr-scid/scid Jel (SCID mouse) were used as mice. SCID mice were subcutaneously administered 100 μL of the prepared cell suspension, and the cells were allowed to settle (3) miRNA Administration Negative control which is the control sequence and miR-3140-3p which is the miRNA of the present invention were employed. A6K (from 3D Matrix) was employed as the nucleic acid delivery reagent. The administration of miRNA to mice was carried out with the following protocol.

1: 100 μM of the nucleic acid (miRNA) was diluted with 10% saline and sterilized water in order to obtain 71.4 μM.

2: 1% A6K solution was sonicated for 5 minutes before use.

3: The diluted nucleic acid and the 1% A6K solution were mixed at a proportion of 1:1 to give the administration nucleic acid.

4: SCID mice were subcutaneously administered (tumor site) 50 μL each of the administration nucleic acid.

(5) Evaluation

The experimental results were evaluated with the following protocol.

1: From four days after transplantation, the nucleic acid was administered every one or two days.

2: A total of 13 administrations were performed, and 34 days after transplantation was set as the endpoint.

3: Mice were dissected, and the subcutaneous tumor was resected and weighed.

Experimental results are shown in FIG. 13 (n=3). As shown in FIG. 13, compared to the control group, the tumor weight was significantly lower in mice in which miR-3140-3p was introduced at the tumor site.

Figure 14:
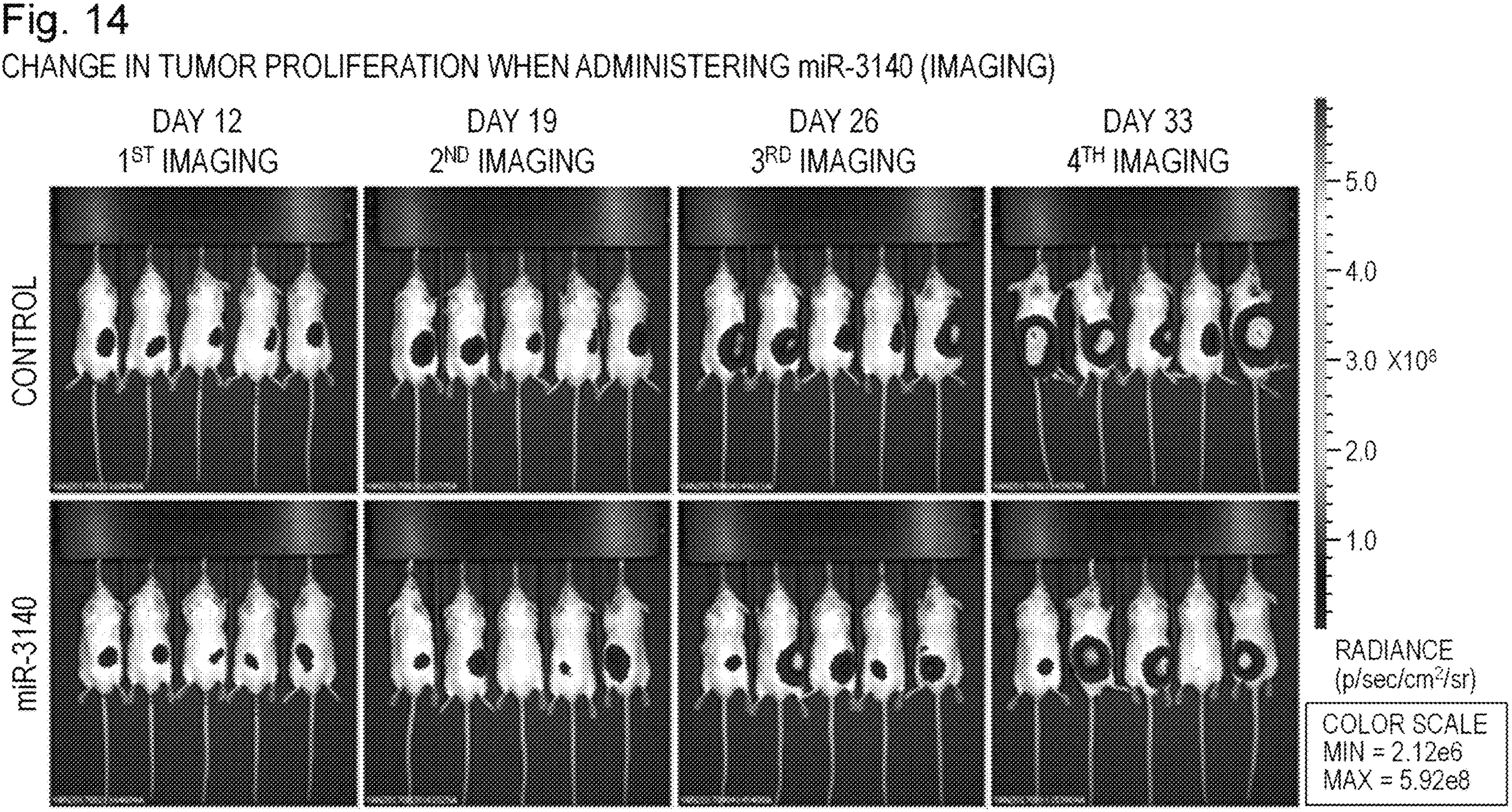
FIG. 14 shows imaging analysis results of tumor tissues at 12, 19, 26, and 33 days after tumor cell transplantation.
Figure 15:
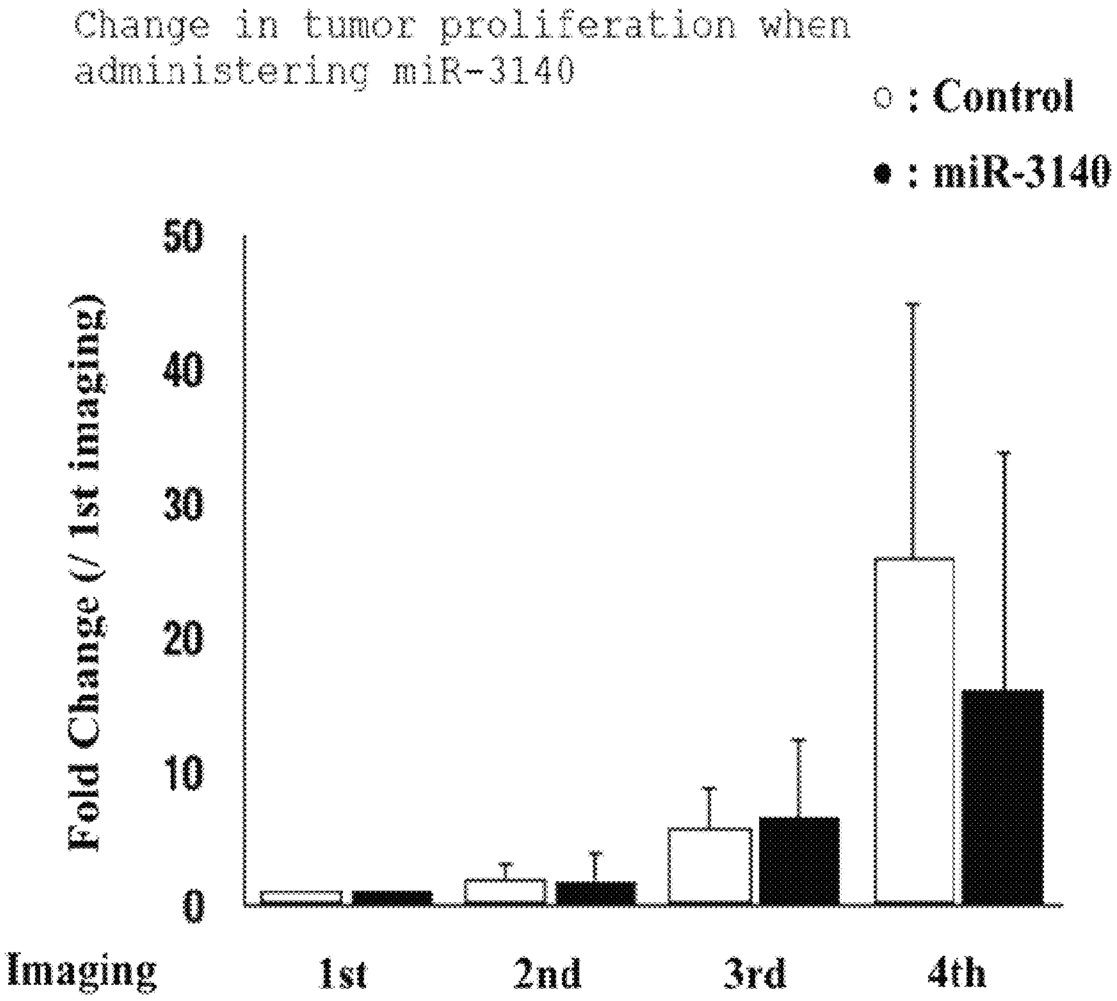
FIG. 15 shows a graph quantifying the imaging analysis results from FIG. 14.
Figure 16:
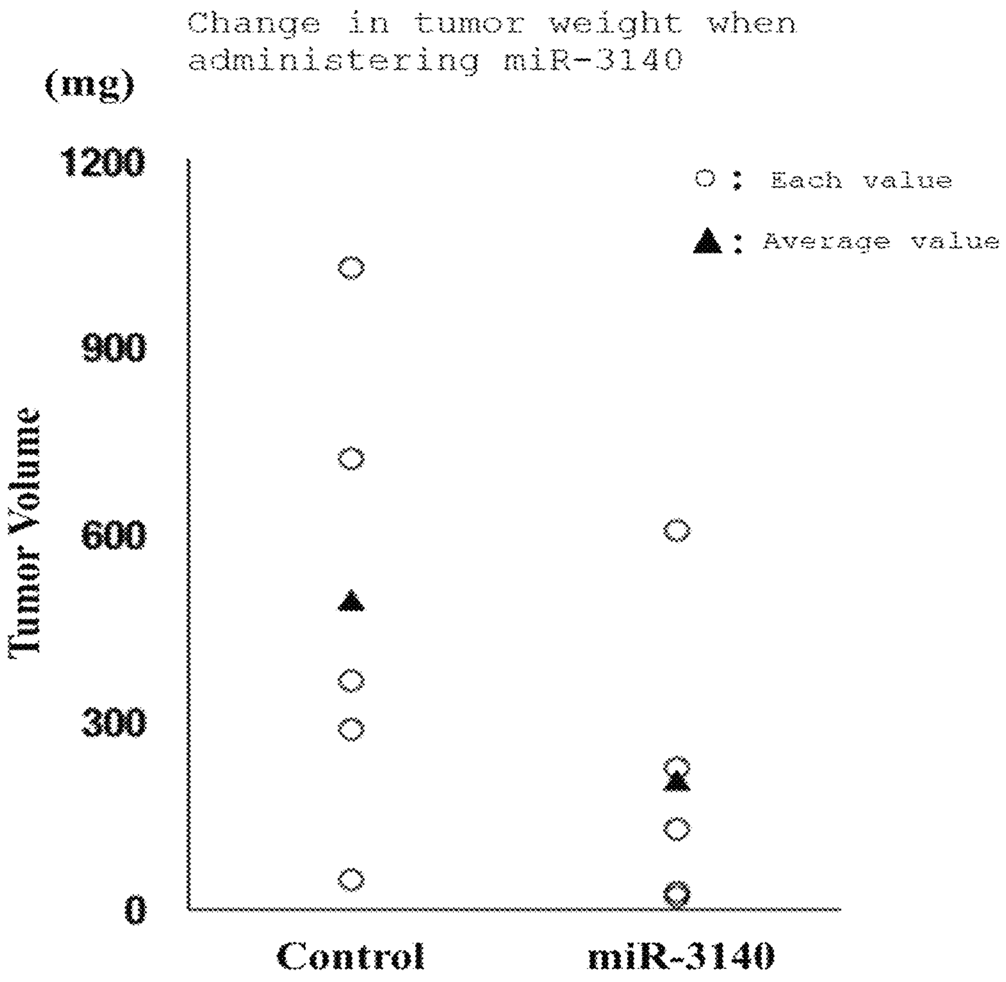
FIG. 16 shows the results of comparing tumor weights at endpoint.

Experiment 5. Antitumor Effect of the miRNA of the Present Invention In Vivo (Malignant Pleural Mesothelioma Cells) (FIG. 14-16)

(1) Preparation of Cells

Malignant pleural mesothelioma cells EHMES-10 cells were used.

1: The cells on the dish were washed twice with PBS (−).

2: The cells were detached with trypsin.

3: This was suspended in a medium, and cells were counted.

4: Centrifugation at a condition of 1000 rpm for 3 min was performed to pellet down.

5: The cells were resuspended in PBS (–) in order to obtain $2.0\times10^7$ cells/mL.

(2) Cell Transplantation to Mice

Six weeks-old C-B-17/Icr-scid/scid Jel (SCID mouse) were used as mice. SCID mice were subcutaneously administered 100 μL of the prepared cell suspension, and the cells were allowed to settle.

(3) miRNA Administration

Negative control which is the control sequence and miR-3140-3p which is the miRNA of the present invention were employed. A6K (from 3D Matrix) was employed as the nucleic acid delivery reagent. The administration of miRNA to mice was carried out with the following protocol.

1: 100 μM of the nucleic acid (miRNA) was diluted with 10% saline and sterilized water in order to obtain 71.4 μM.

2: 1% A6K solution was sonicated for 5 minutes before use.

3: The diluted nucleic acid and the 1% A6K solution were mixed at a proportion of 1:1 to give the administration nucleic acid.

4: SCID mice were subcutaneously administered (tumor site) 50 μL each of the administration nucleic acid.

(5) Evaluation

The experimental results were evaluated with the following protocol.

1: From two days after transplantation, the nucleic acid was administered every one or two days.

2: A total of 13 administrations were performed, and 33 days after transplantation was set as the endpoint.

3: At 12, 19, 26, and 33 days after transplantation, luciferin was intraperitoneally administered for imaging in order to trace the tumor size.

4: Mice were dissected at the endpoint, and the subcutaneous tumor was resected and weighed.

Imaging analysis results of tumor tissues at 12, 19, 26, and 33 days after tumor cell transplantation are shown in FIG. 14 and FIG. 15. As shown in FIG. 14 and FIG. 15, compared to the control group, expansion of the tumor was suppressed in mice in which miR-3140-3p was introduced at the tumor site. Moreover, a similar result was shown in FIG. 16 which compares the tumor weight at endpoint.

Figure 17:
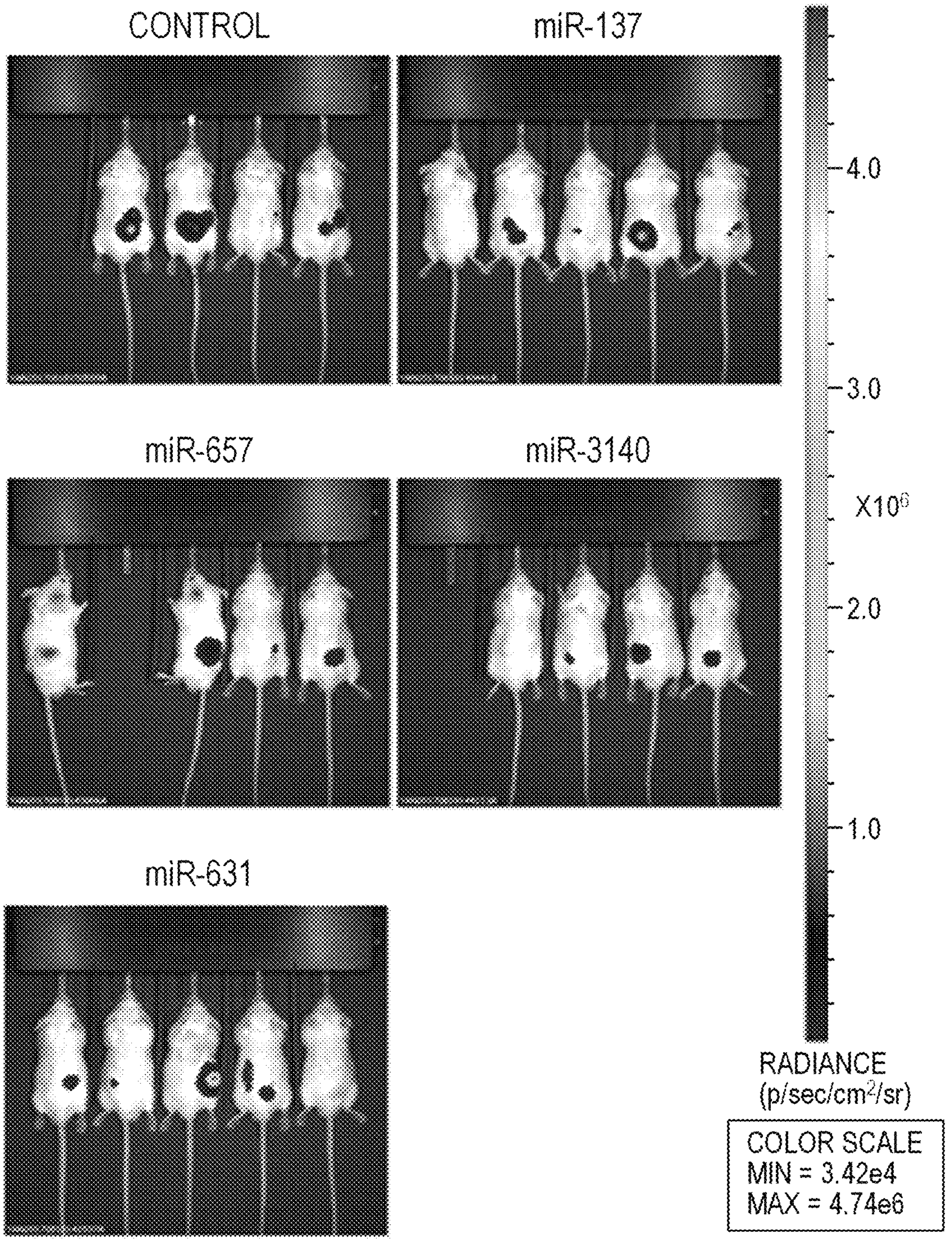
FIG. 17 shows imaging analysis results of tumor tissues after tumor cell transplantation.
Figure 18:
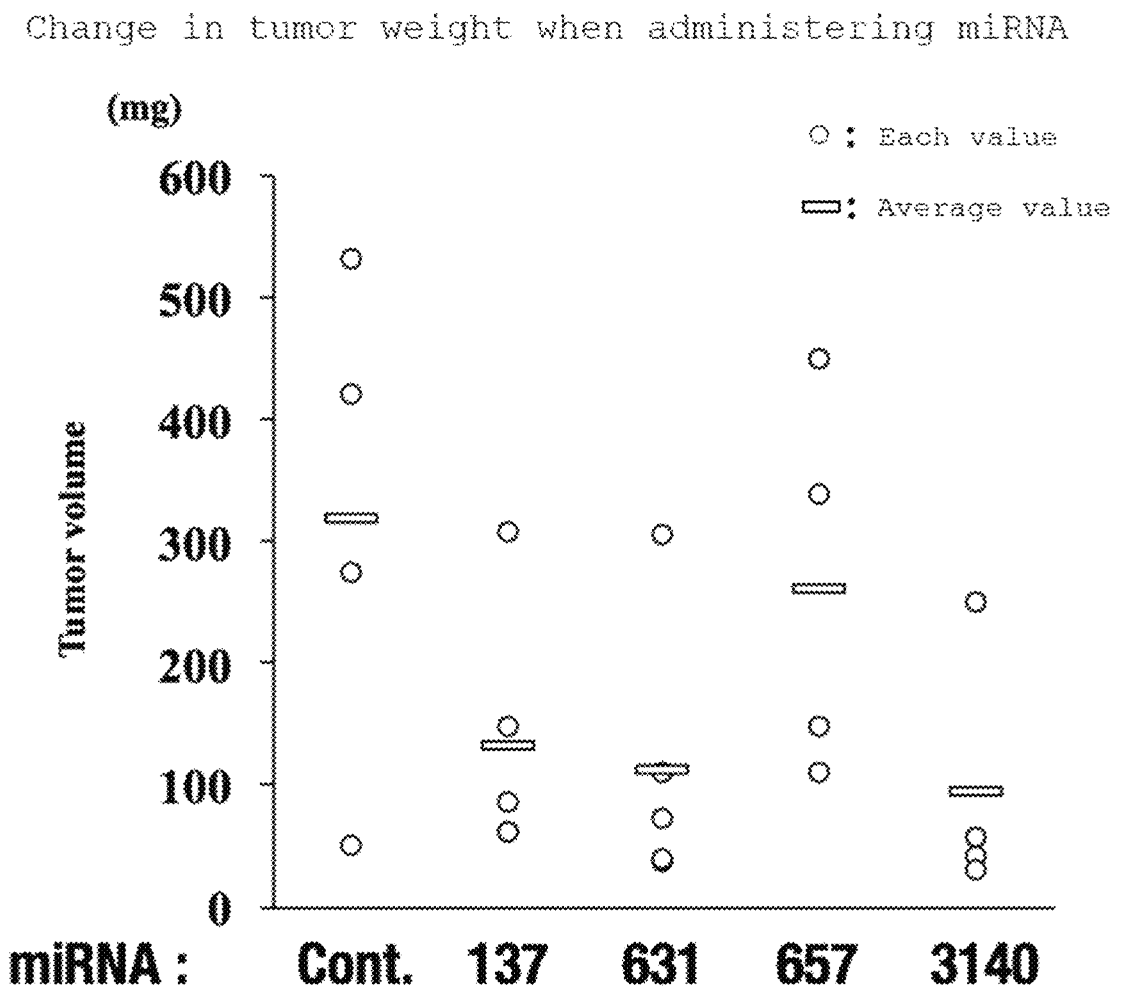
FIG. 18 shows the results of comparing tumor weights at endpoint.

Experiment 6. Antitumor Effect of the miRNA of the Present Invention In Vivo (Tongue Cancer Cell) (FIGS. 17 and 18)

(1) Preparation of Cells

Tongue cancer cell strain HSC-4 cells were used.

1: The cells on the dish were washed twice with PBS (–).

2: The cells were detached with trypsin.

3: This was suspended in a medium, and cells were counted.

4: Centrifugation at a condition of 1000 rpm for 3 min was performed to pellet down.

5: The cells were resuspended in PBS (–) in order to obtain $2.0\times10^7$ cells/mL.

(2) Cell Transplantation to Mice

Six weeks-old C-B-17/Icr-scid/scid Jcl (SCID mouse) were used as mice. SCID mice were subcutaneously administered 100 μL of the prepared cell suspension, and the cells were allowed to settle.

(3) miRNA Administration

Negative control which is the control sequence and miR-3140-3p, miR-137, miR-631 and miR-657 which are the miRNAs of the present invention were employed. A6K (from 3D Matrix) was employed as the nucleic acid delivery reagent. The administration of miRNA to mice was carried out with the following protocol.

1: 100 μM of the nucleic acid (miRNA) was diluted with 10% saline and sterilized water in order to obtain 71.4 μM.

2: 1% A6K solution was sonicated for 5 minutes before use.

3: The diluted nucleic acid and the 1% A6K solution were mixed at a proportion of 1:1 to give the administration nucleic acid.

4: SCID mice were subcutaneously administered (tumor site) 50 μL each of the administration nucleic acid.

(5) Evaluation

The experimental results were evaluated with the following protocol.

1: From three days after transplantation, the nucleic acid was administered every one or two days.

2: A total of 11 administrations were performed, and 28 days after transplantation was set as the endpoint.

3: At 7, 14, 21, and 28 days after transplantation, luciferin was intraperitoneally administered for imaging in order to trace the tumor size.

4: Mice were dissected at the endpoint, and the subcutaneous tumor was resected and weighed.

Imaging analysis results of tumor tissues after tumor cell transplantation are shown in FIG. 17. As shown in FIG. 17, compared to the control group, expansion of the tumor was suppressed in mice in which the miRNA of the present invention was introduced at the tumor site. Moreover, a similar result was shown in FIG. 18 which compares the tumor weight at endpoint.

From the above results, it was shown that the miRNA of the present invention also exerts extremely strong antitumor effect in vivo.

Experiment 7. Antitumor Effect of the miRNA of the Present Invention In Vivo (Malignant Pleural Mesothelioma Cells) (FIGS. 19-28)

The tumor suppression effect of miR-3140-3p in vivo was investigated with intrathoracic orthotopic transplantation model mouse.

Six weeks-old male mice (C-B-17/Icr-scid/scid Jcl) were used as mice. Malignant pleural mesothelioma cell strain EHMES-10 which expresses the luciferase gene was used as the tumor cell.

The experiment protocol is shown below.

1: Mice were intraperitoneally administered 0.1 mL per 10 g of body weight of a mixed anesthetic drug of medetomidine hydrochloride, midazolam, and butorphanol tartrate.

2: After anesthesia, mouse chest hair was shaved, and an incision was made in the epidermis with scissors.

3: In the mouse pleural cavity 100 μL of tumor cells ($3\times10^7$ cells/mL) was transplanted with a 27 G syringe for insulin.

4: Three days after transplantation, imaging of tumor cells was performed with IVIS Spectrum CT In vivo Imaging System.

5: After imaging, grouping was performed with successfully transplanted mice.

6: Mice were intraperitoneally administered 0.1 mL per 10 g of body weight of a mixed anesthetic drug of medetomidine hydrochloride, midazolam, and butorphanol tartrate to anesthetize the mice.

7: After anesthesia, 100 μL of miRNA/A6K mixture was administered in the mouse pleural cavity.

8: Imaging was performed every week from the first imaging, and tumor expansion was observed.

9: The time and date of death of the mice was recorded, and mice survival rate was calculated.

Figure 19:
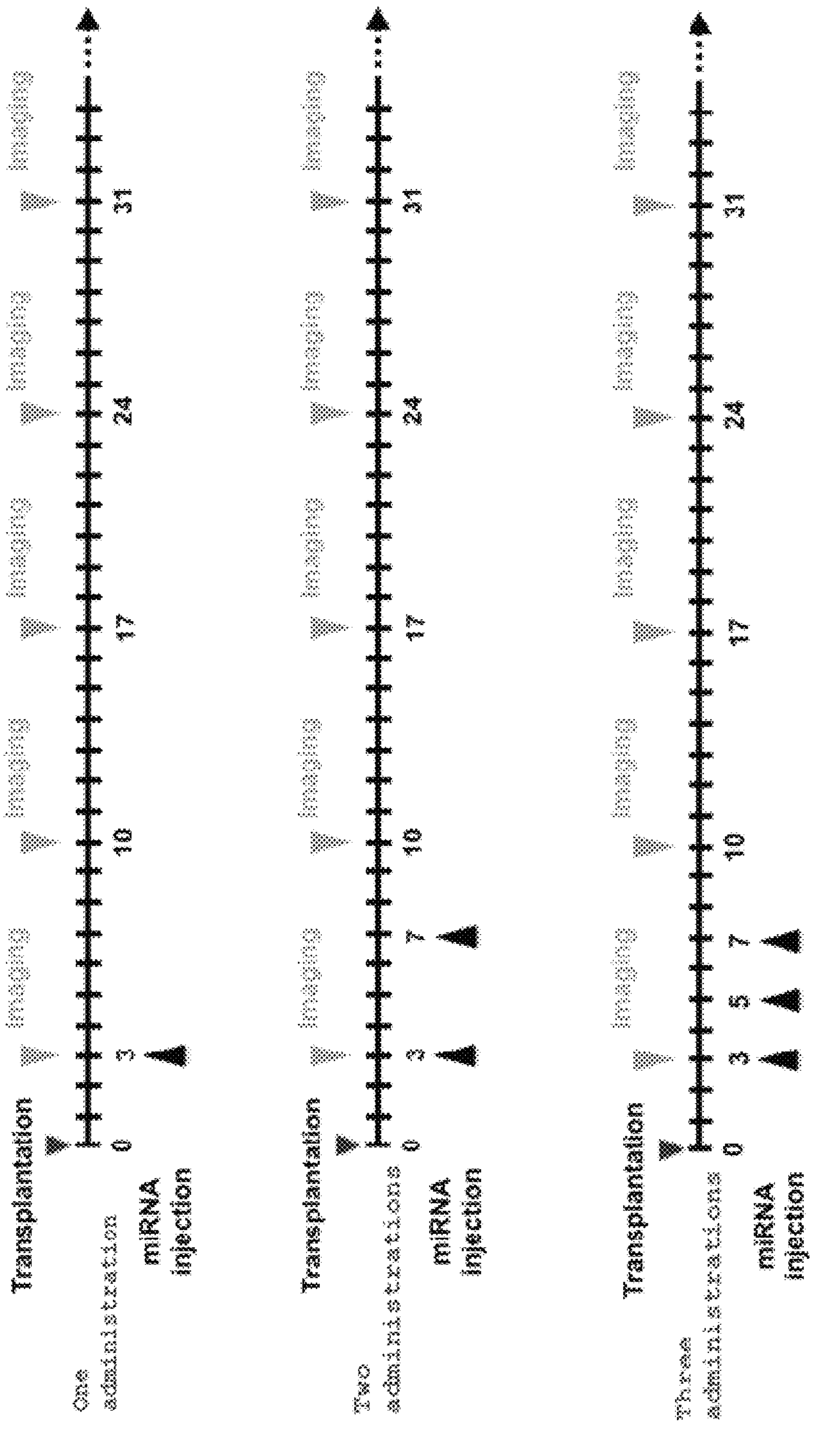
FIG. 19 shows the schedule in Experiment 7.

Administration and imaging schedule is shown in FIG. 19. The mixed anesthetic drug of medetomidine hydrochloride, midazolam, and butorphanol tartrate was prepared as in Table 8 below. The miRNA/A6K mixture was prepared as in Table 9. Moreover, the control group was administered the RNA shown in Table 10 instead of the miRNA of the present invention.

Note that in order to improve expression efficiency, miRNA was administered as a double-strand in combination with a complementary strand comprising partial mismatch.

TABLE 8

Preparation of mixed anesthetic drug

| | Medetomidine hydrochloride (1 mg/mL) | Midazolam (5 mg/mL) | Butorphanol tartrate (0.5 mg/mL) | Water for injection |
|---|---|---|---|---|
| Required amount of stock solution | 0.75 mL | 2 mL | 2.5 mL | 19.75 mL |

TABLE 9

Preparation of miRNA/A6K mixture

| | /120 μL |
|---|---|
| 100 μM miRNA | 40 μL |
| 10% saline | 10.8 μL |
| 1% A6K | 50 μL |
| Water for injection | 9.2 μL |

miRNA is administered at 3.2 nmol (45 μg) per mouse.

TABLE 10

Sequences of control and miR-3140-3p

| | Sequence |
|---|---|
| Control | 5'UUCUCCGAACGUGUCACGU (SEQ ID NO. 30)<br>5'ACGUCACACGUUCGGAGAA (SEQ ID NO. 31) |
| miR-3140-3p | 5'AGCUUUUGGGAAUUCAGGUAGU (SEQ ID NO. 2)<br>5'UACCUGAAUUCCCAAAAGCUUU (SEQ ID NO. 32) |

Experimental results are shown in FIG. 20 to FIG. 28.

Figure 20:
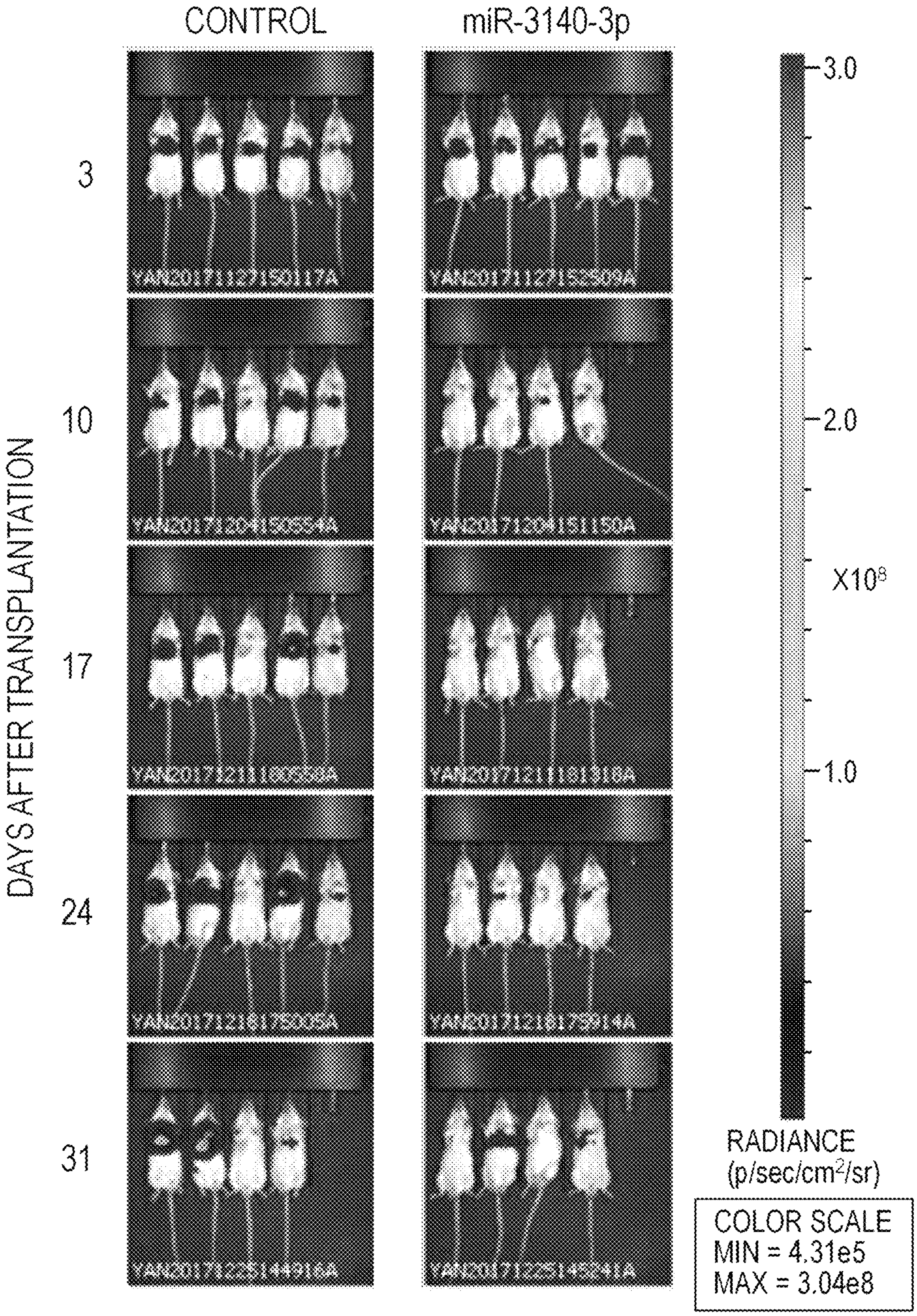
FIG. 20 shows the imaging results when miR-3140-3p is administered once.

In the group with one administration of miR-3140-3p, tumor reduction was seen by the second imaging (Day 10 after transplantation), and the effect had persisted until the fourth imaging (Day 24 after transplantation) (FIG. 20).

Figure 21:
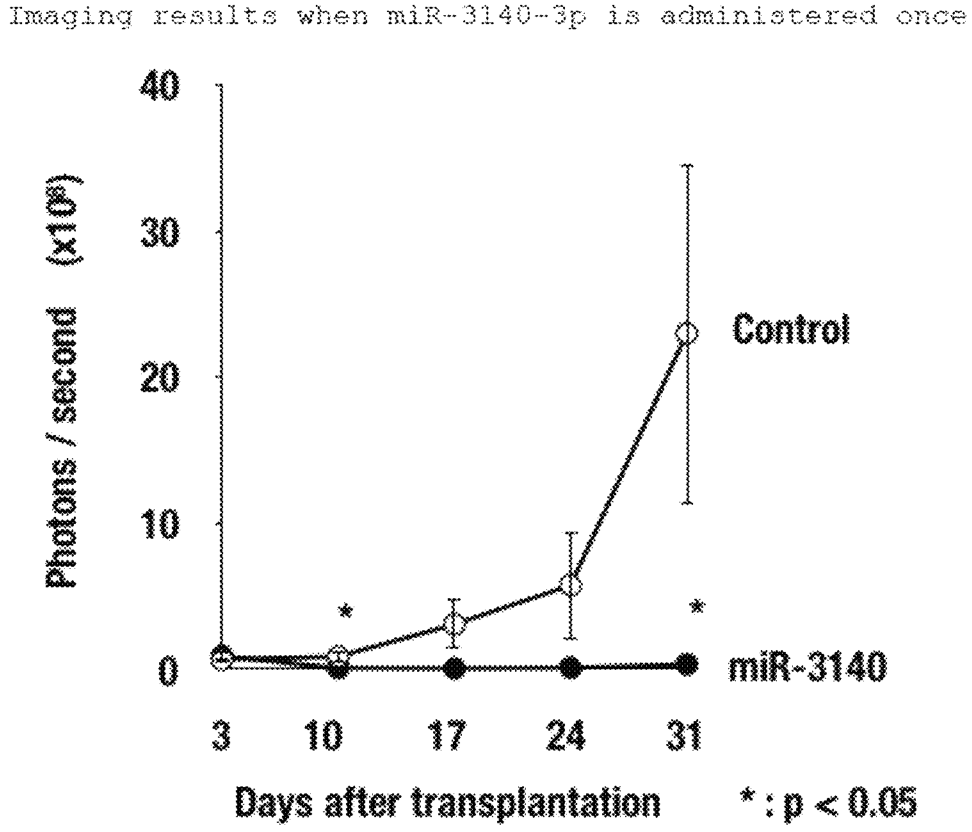
FIG. 21 shows the imaging results when miR-3140-3p is administered once.

The imaging results were digitized and graphed, and it was shown that miR-3140-3p significantly suppressed tumor expansion (FIG. 21).

Figure 22:
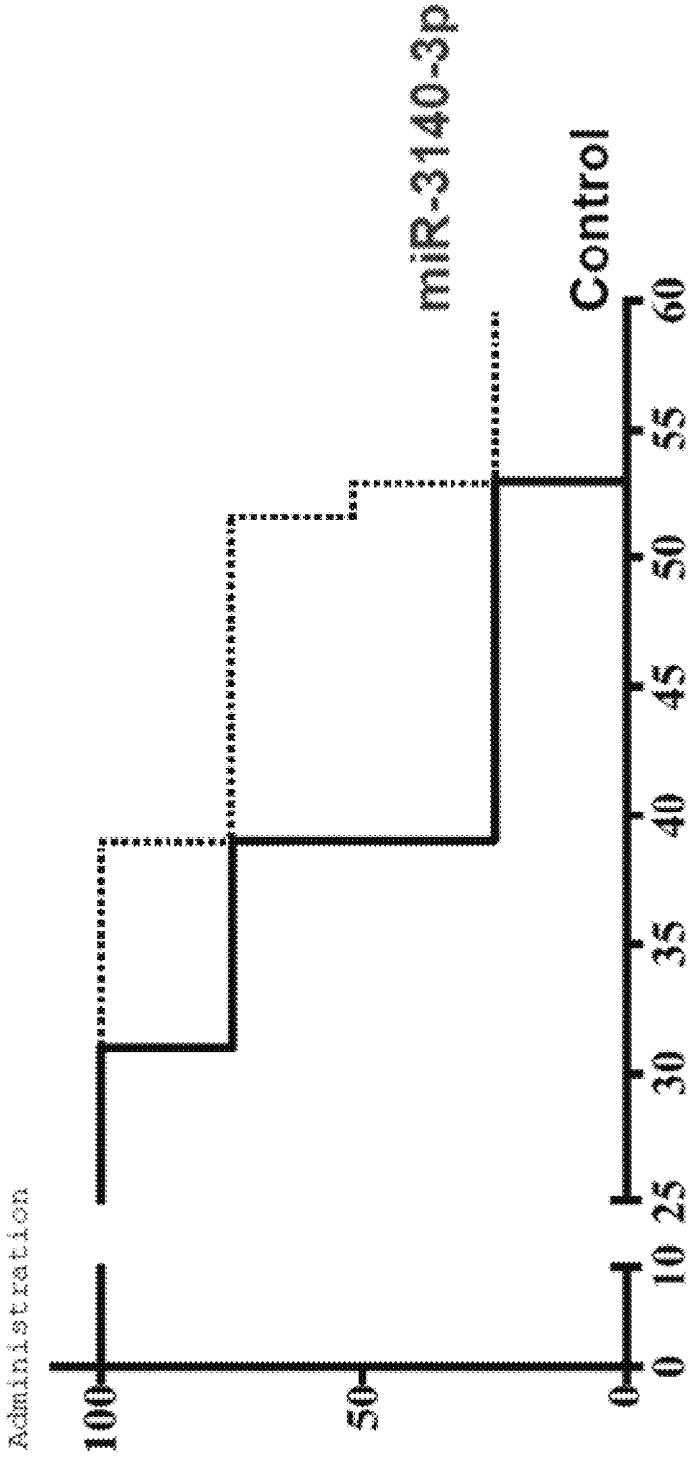
FIG. 22 shows survival rates of mice when miR-3140-3p is administered once.
Figure 23:
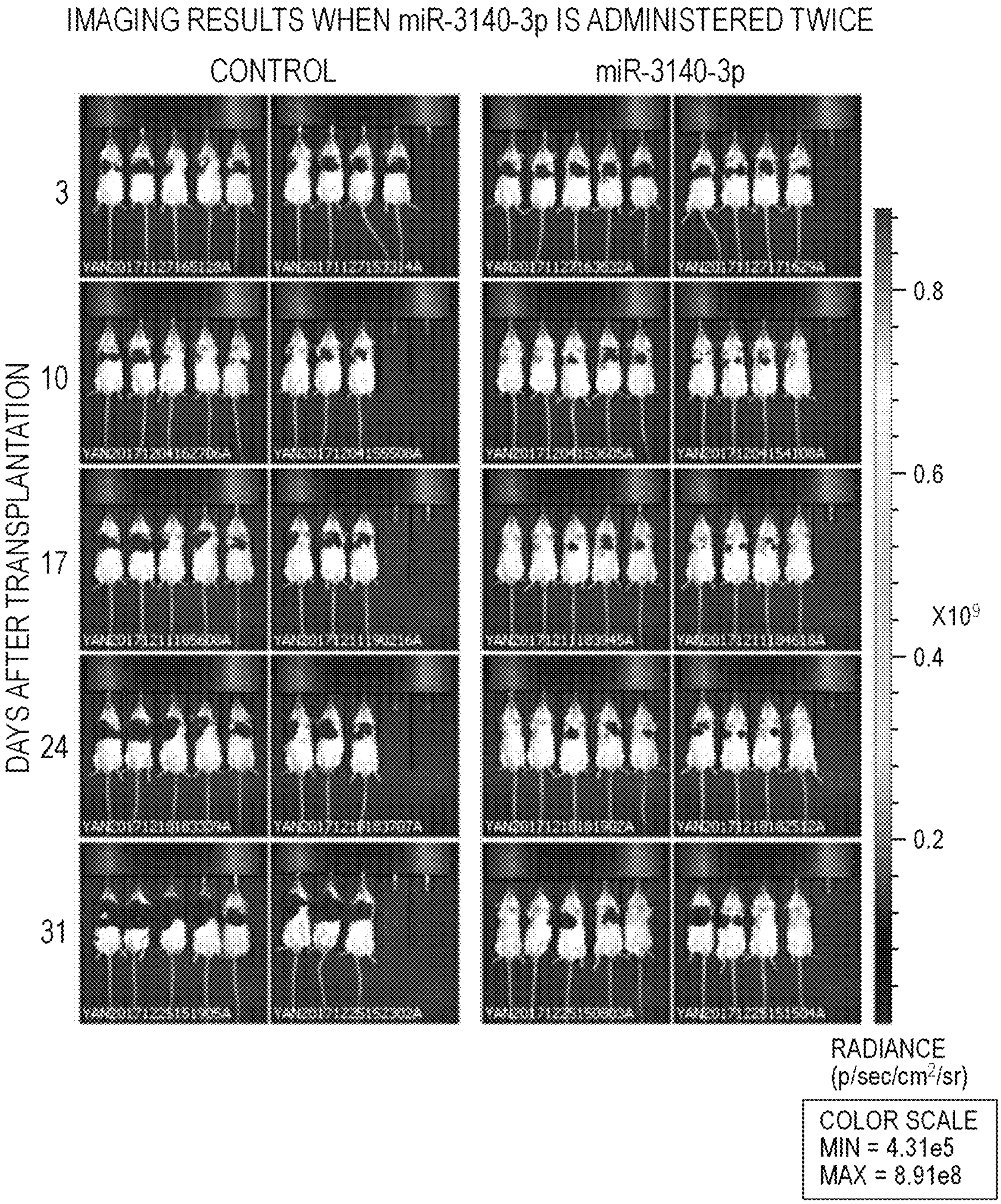
FIG. 23 shows the imaging results when miR-3140-3p is administered twice.
Figure 24:
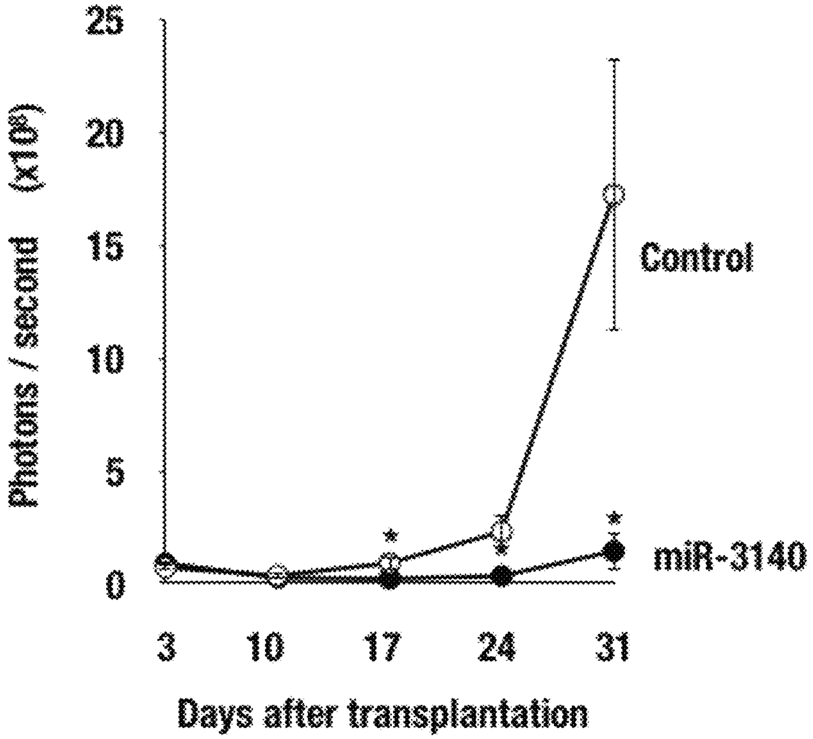
FIG. 24 shows the imaging results when miR-3140-3p is administered twice.
Figure 25:
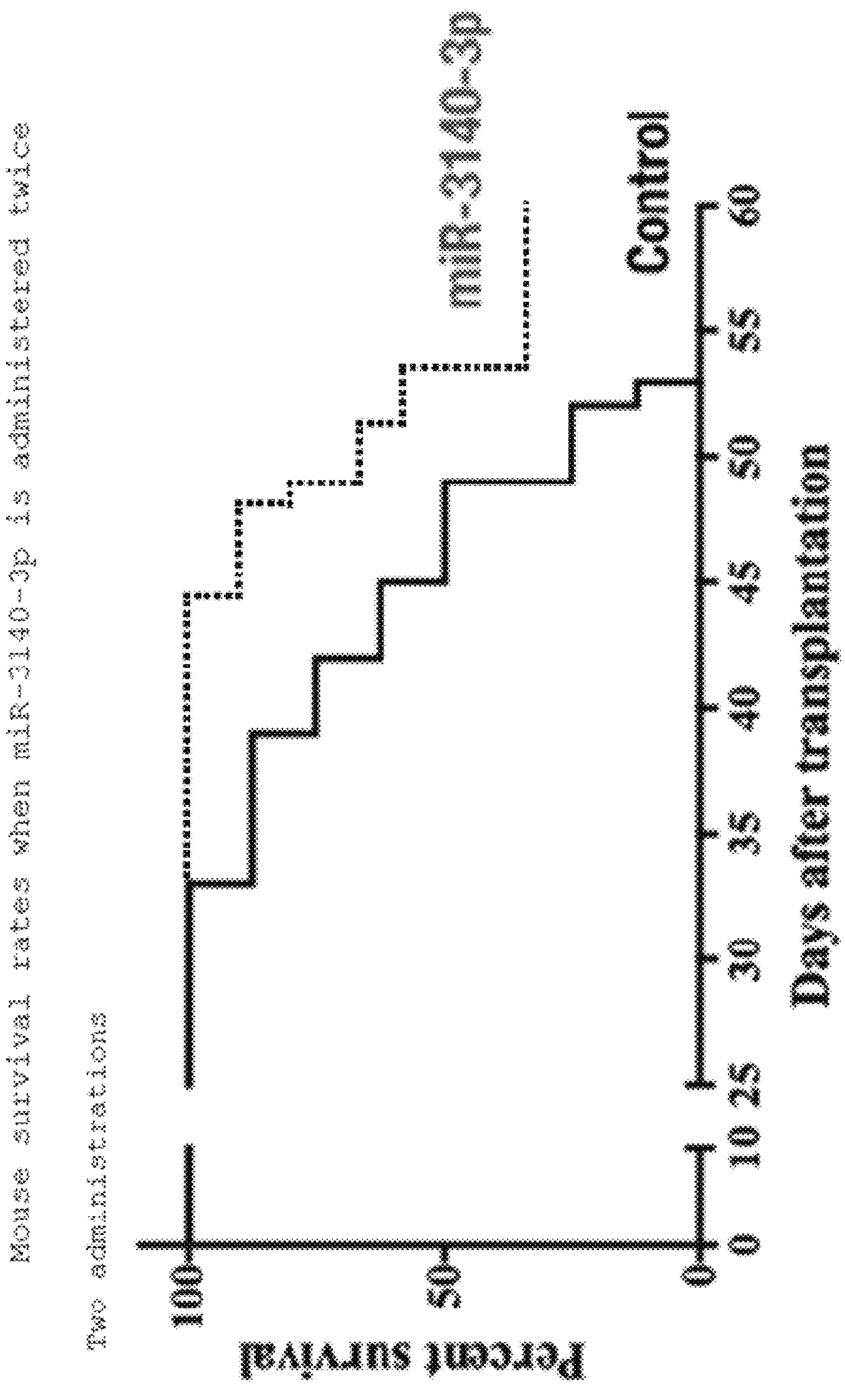
FIG. 25 shows the survival rates of mice when miR-3140-3p is administered twice.
Figure 26:
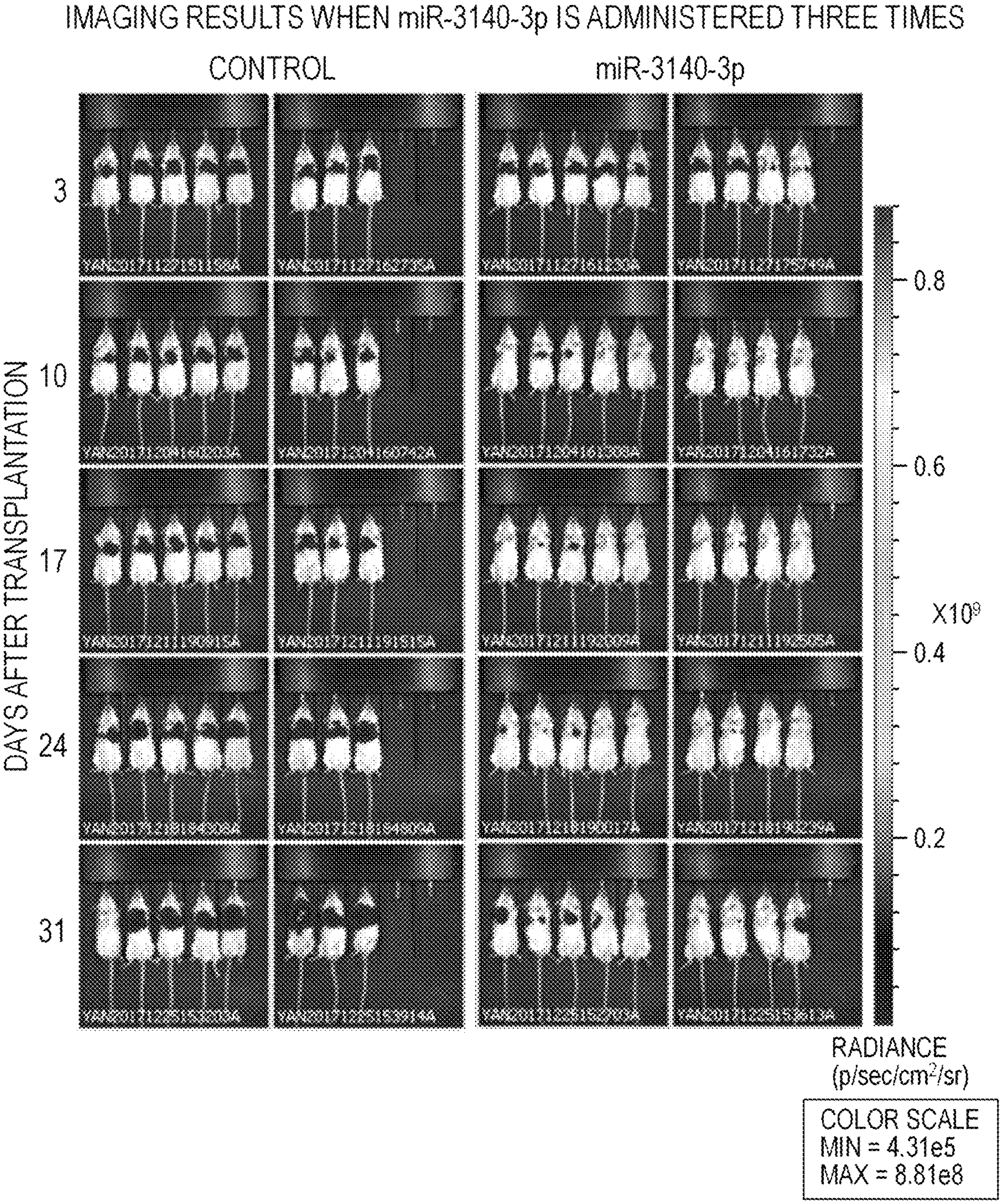
FIG. 26 shows the Imaging results when miR-3140-3p is administered three times.
Figure 27:
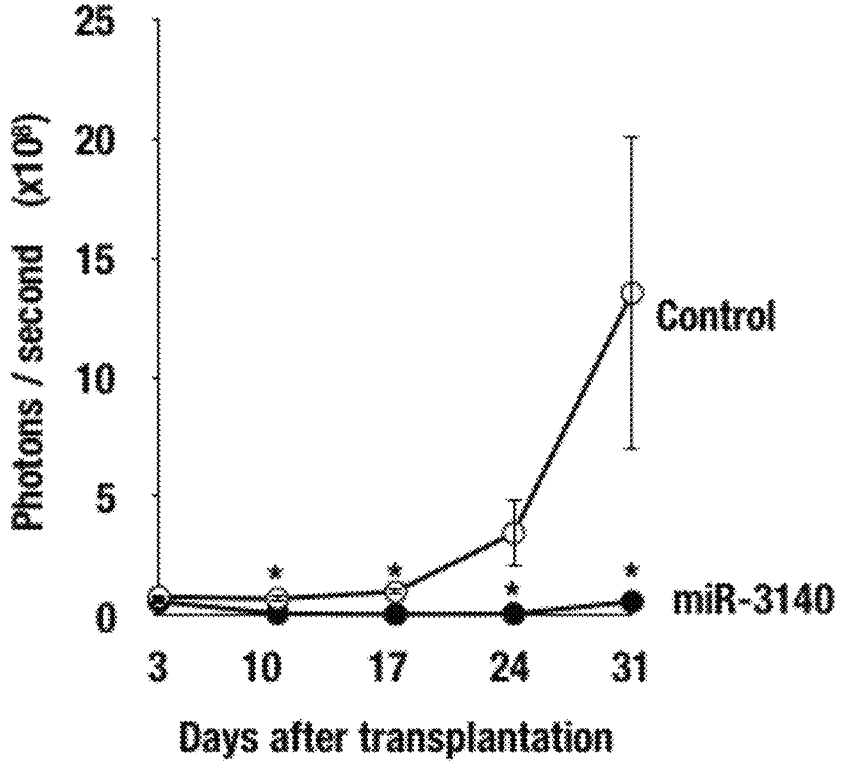
FIG. 27 shows the Imaging results when miR-3140-3p is administered three times.

By comparing the survival rates of mice, it was observed that the survival rates of mice had improved in the miR-3140-3p administration group (FIG. 22).

It was shown that similarly to the group with one administration, miR-3140-3p also significantly suppressed malignant pleural mesothelioma in the groups with two and three administrations of miR-3140-3p (FIGS. 23-28).

Figure 28:
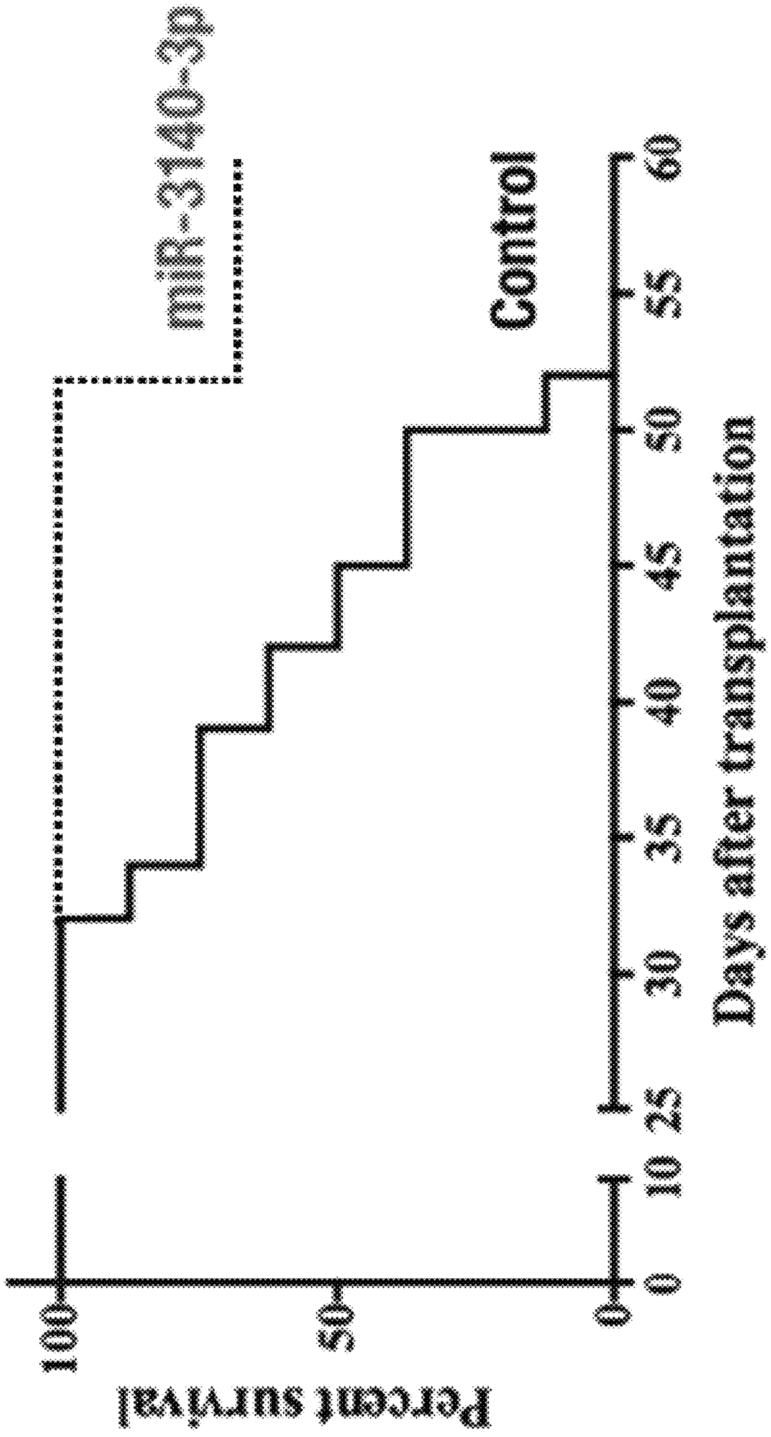
FIG. 28 shows the survival rates of mice when miR-3140-3p is administered three times.

The survival rates of mice were more improved in the group with three administrations of miR-3140-3p (FIG. 28).

Figure 29:
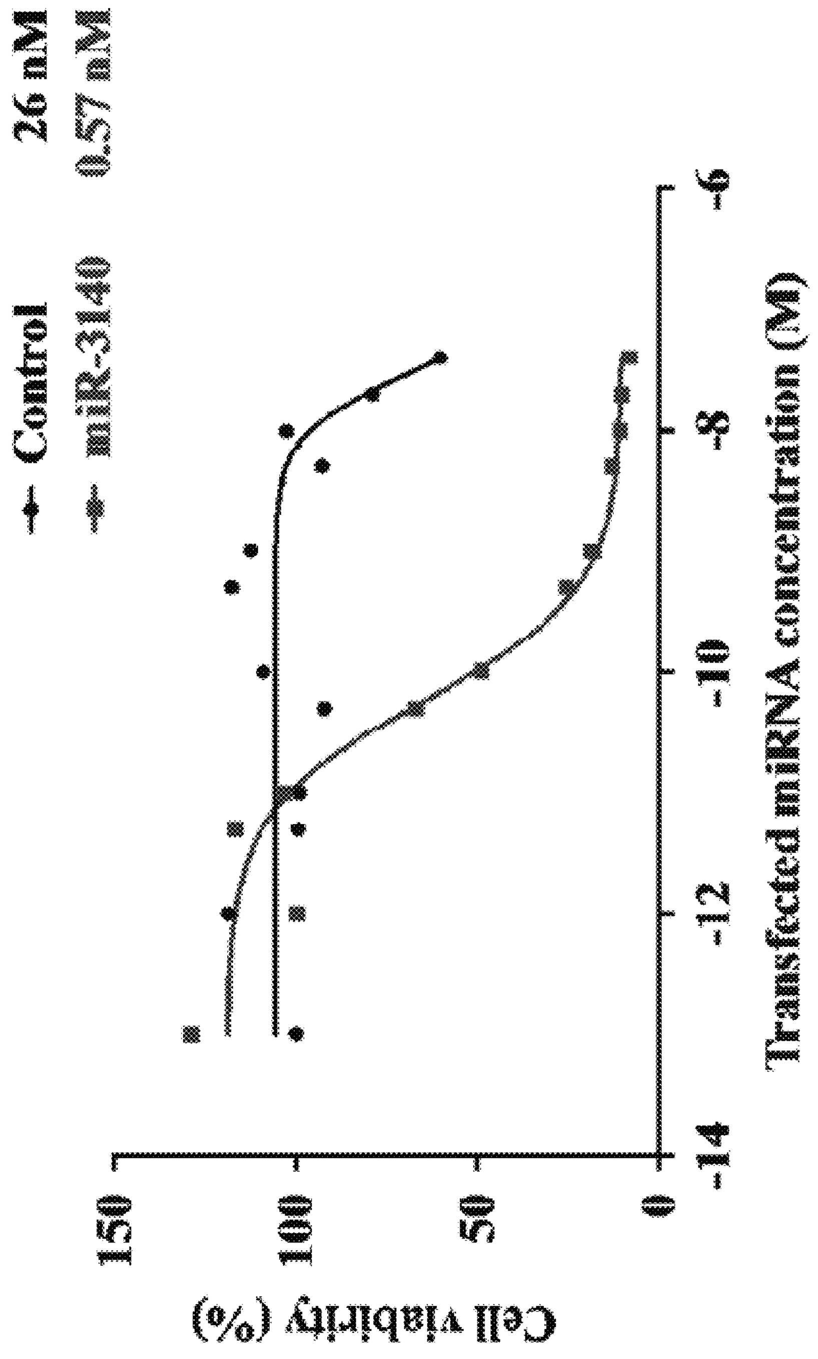
FIG. 29 shows the results of Experiment 8.
Figure 30:
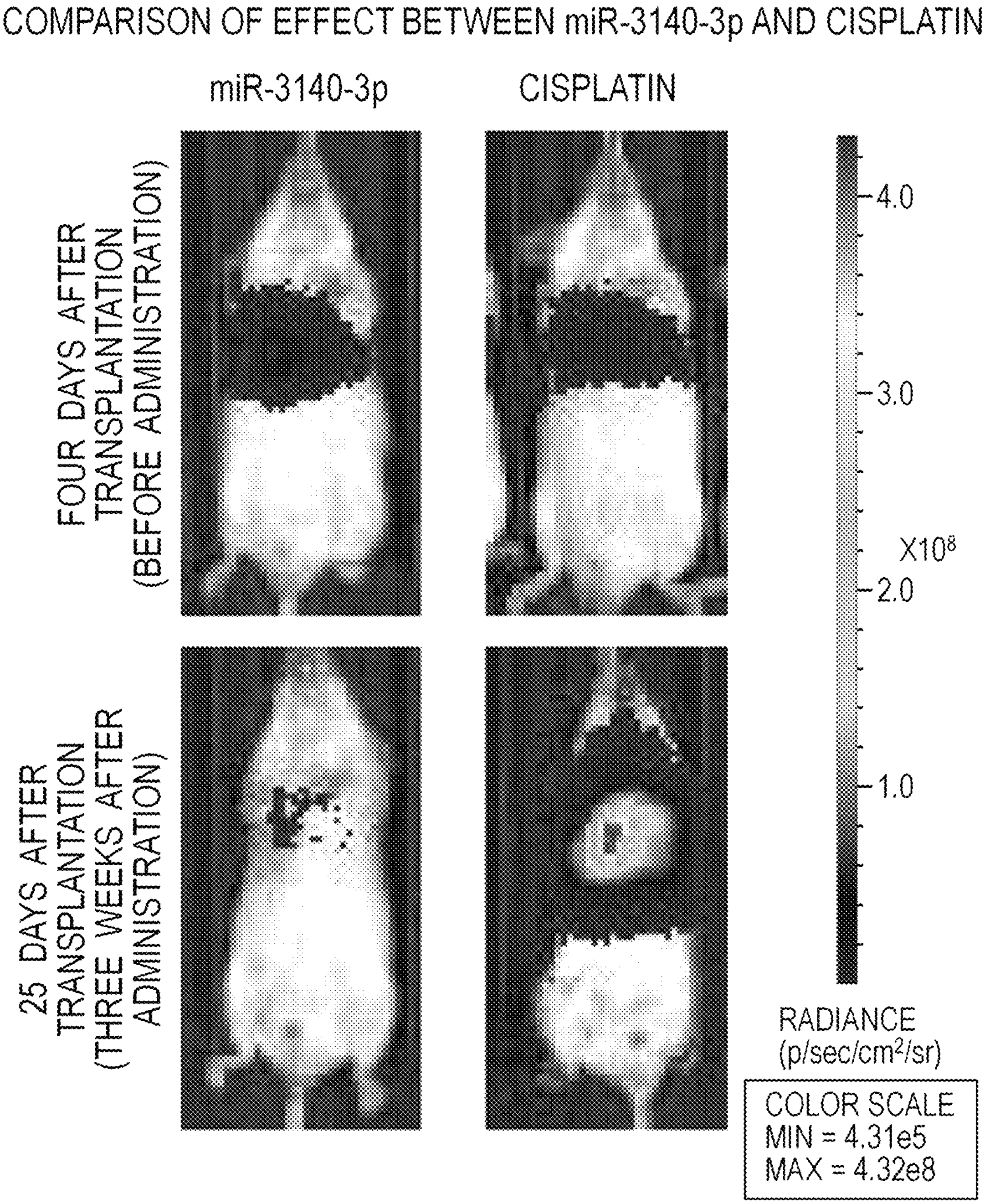
FIG. 30 shows the comparison of tumor suppression effect between miR-3140-3p and cisplatin.
Figure 31:
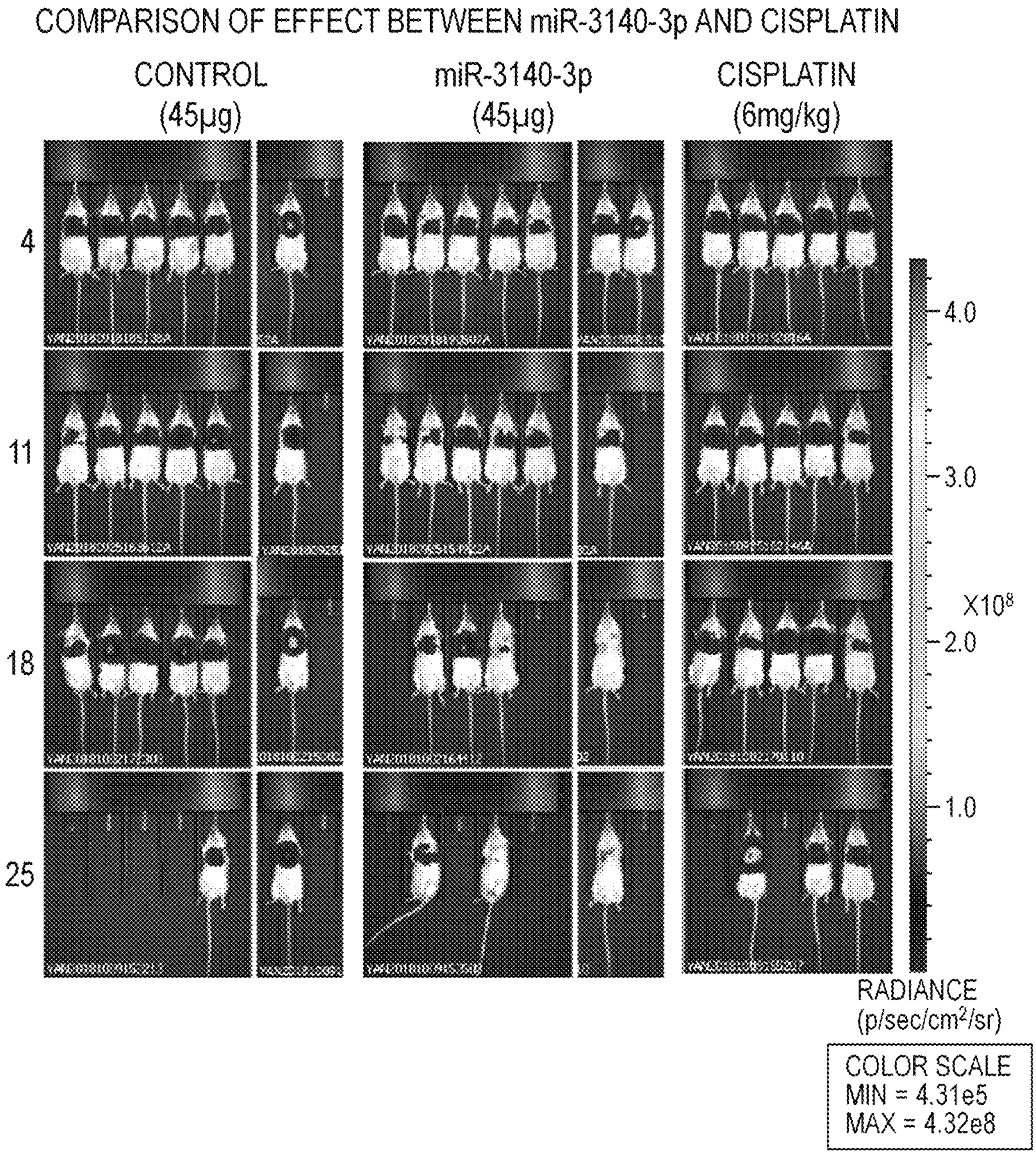
FIG. 31 shows the comparison of tumor suppression effect between miR-3140-3p and cisplatin.
Figure 32:
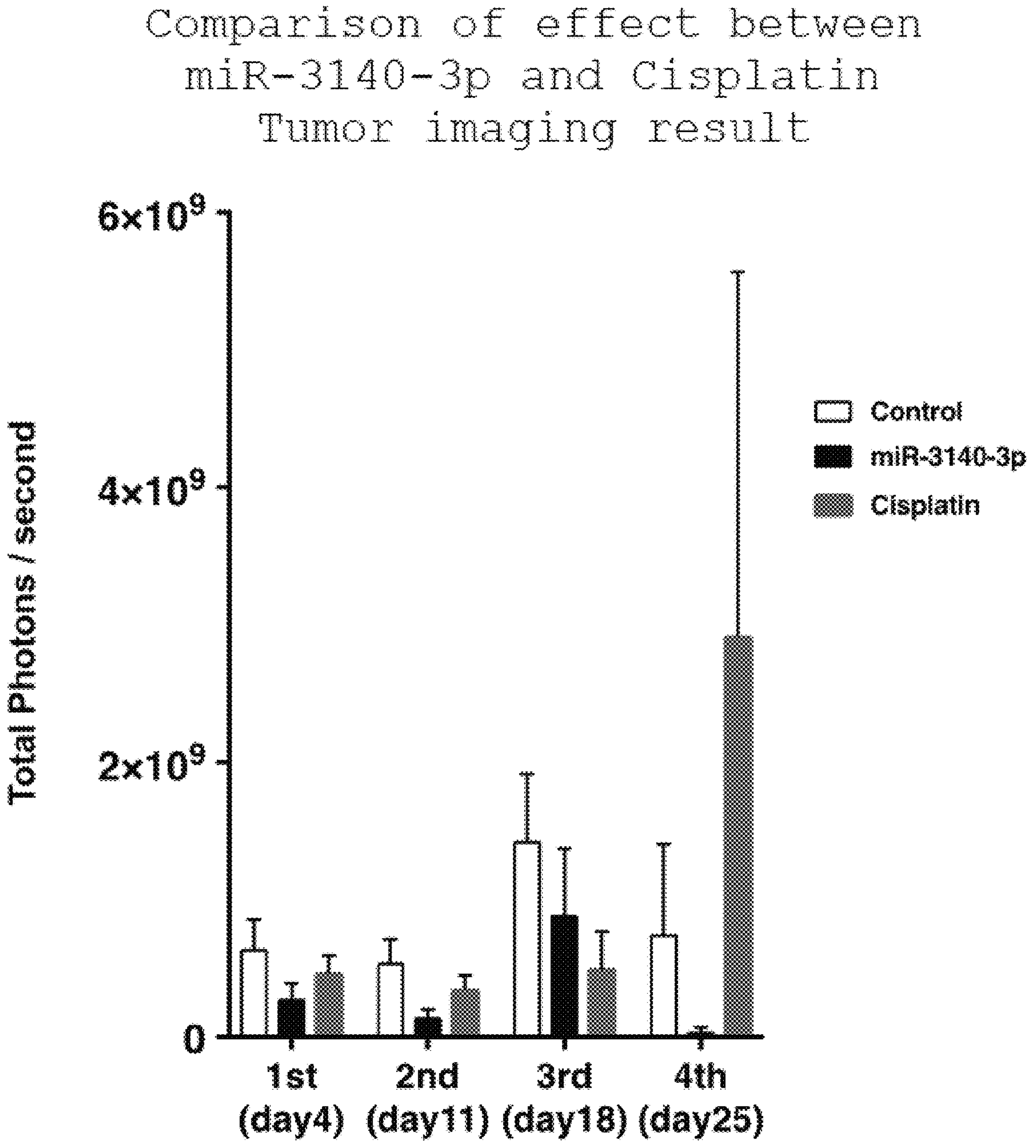
FIG. 32 shows the comparison of tumor suppression effect between miR-3140-3p and cisplatin.
Figure 33:
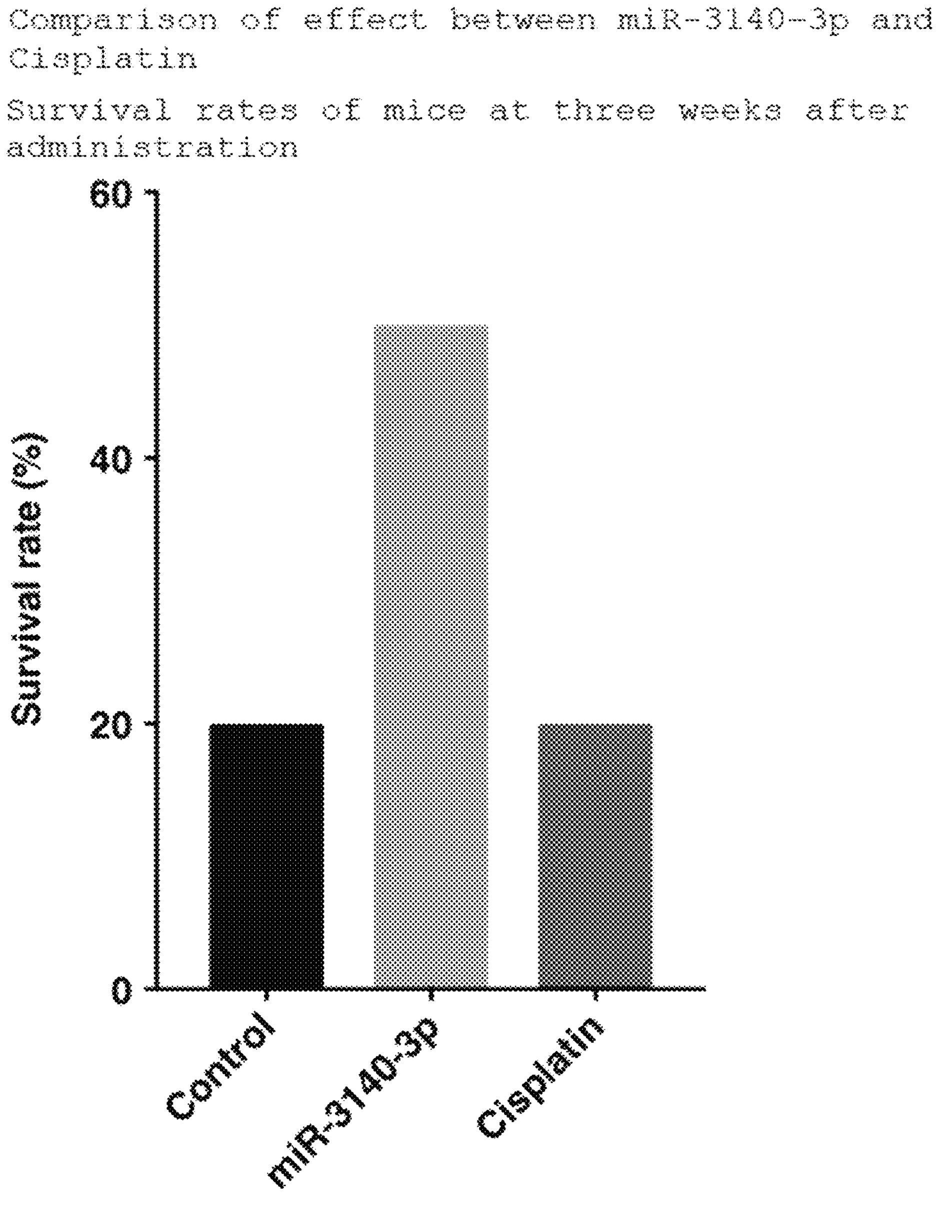
FIG. 33 shows the comparison of survival rates between miR-3140-3p administration group and cisplatin administration group.

Experiment 8. Calculation of $IC_{50}$ Value (FIG. 29)

The $IC_{50}$ value of miR-3140-3p was calculated with malignant pleural mesothelioma cell EHMES-10.

The protocol therefor is shown below.

1: To 25 μL of serum free medium (SFM) was added 0.25 μL of RNAiMAX (Invitrogen).

2: miR-Control and miR-3140-3p were serially diluted so that the final concentrations will be 40 nM, 20 nM, 10 nM, 5 nM, 1 nM, 500 pM, 100 pM, 50 pM, 10 pM, 5 pM, and 1 pM, and mixed with SFM/RNAiMAX complex.

3: This was incubated at room temperature for 20 minutes.

4: 75 μL of each of cells at $6.7\times10^4$ cells/mL were added to each well.

5: This was incubated at 37° C. under 5% $CO_2$ condition.

6: Five days after transfection, the survival rates of cells were investigated with Cell Counting Kit 8 (DOJINDO). The protocol therefor is shown below.

(i) Cell Counting Kit was diluted 10-folds with a medium.

(ii) 200 μL of each of the diluted Cell Counting Kit was added to each well.

(iii) This was incubated at 37° C. under 5% $CO_2$ condition for 1 hour.

(iv) The values at 450 nm/600 nm were measured with a plate reader.

Note that the same control RNA as that used in Experiment 7 was employed as the control.

Results are shown in FIG. 29. As shown in FIG. 29, it was revealed that miR-3140-3p shows growth inhibition effect against malignant pleural mesothelioma cell strain EHMES-10 even at a very low concentration. Calculation of the $IC_{50}$ value gave a final concentration of 0.57 nM.

Experiment 9. Comparison of Antitumor Effect with Chemotherapy Agents (FIGS. 30-33)

In order to investigate the relative superiority of antitumor effect of miR-3140-3p, the tumor suppression effect of cisplatin which is the first-line drug of malignant pleural mesothelioma and the tumor suppression effect of miR-3140-3p were compared in vivo.

Six weeks-old male mice (C-B-17/Icr-scid/scid Jcl) were used as mice. Malignant pleural mesothelioma cell strain EHMES-10 which expresses the luciferase gene was used as the tumor cell.

The protocol is shown below.

1: Mice were intraperitoneally administered 0.1 mL per 10 g of body weight of a mixed anesthetic drug of medetomidine hydrochloride, midazolam, and butorphanol tartrate.

2: After anesthesia, mouse chest hair was shaved, and an incision was made in the epidermis with scissors.

3: In the mouse pleural cavity 100 μL of tumor cells ($3\times10^7$ cells/mL) was transplanted with a 27 G syringe for insulin.

4: Four days after transplantation, imaging of tumor cells was performed with IVIS Spectrum CT In vivo Imaging System.

5: After imaging, grouping was performed with successfully transplanted mice.

6: Mice were intraperitoneally administered 0.1 mL per 10 g of body weight of a mixed anesthetic drug of medetomidine hydrochloride, midazolam, and butorphanol tartrate to anesthetize the mice.

7: After anesthesia, 100 μL of the miRNA/A6K mixture was administered in the pleural cavity for the miRNA administration group, and cisplatin (6 mg/kg) was intraperitoneally administered to cisplatin administration group.

8: Imaging was performed every week from the first imaging, and tumor expansion was observed.

The mixed anesthetic drug was prepared as in Table 8 shown above. The miRNA/A6K mixture was prepared as in Tables 9 and 10 shown above. Cisplatin was prepared as in Table 11 below.

TABLE 11

| Preparation of cisplatin | |
|---|---|
| | /mL |
| Cisplatin (25 mg/50 mL) | 600 μL |
| DW | 400 μL |

Note that the same control RNA as that used in Experiment 7 was employed as the control.

Experimental results are shown in FIGS. 30-33. As shown in each figure, it was shown that miR-3140-3p may exert an antitumor effect that is equivalent or higher compared to cisplatin which is also the first-line drug of malignant pleural mesothelioma.

The invention claimed is:

1. A cancer therapy method, the method comprising administering to a cancer patient a therapeutically effective amount of an anti-cancerous pharmaceutical composition comprising an RNA, which functions as a mature-miRNA, wherein the RNA comprises:

(i) a mature-miRNA consisting of the sequence of SEQ ID NO:8;

(ii) a mature-miRNA consisting of the sequence of SEQ ID NO:8 having a substitution, addition, and/or deletion of 1-2 bases and having a cancer therapeutic effect; or (iii) an RNA consisting of 90% or more sequence identity to a mature-miRNA consisting of the sequence of SEQ ID NO:8 and having a cancer therapeutic effect, wherein said cancer is a solid cancer.

2. The method according to claim 1, wherein said solid cancer is colon cancer, pancreatic cancer, tongue cancer, mesothelioma, uterine sarcoma, osteosarcoma, breast cancer, lung cancer, or head and neck cancer.

3. The method according to claim 1 wherein said RNA is chemically modified.

4. The method according to claim 3, wherein said chemical modification is one or more chemical modifications selected from the group consisting of LNA-tion, BNA-tion, ENA-ation, 2'-OMe modification, phosphorothioation, S-TuD-ation, morpholino modification, peptide addition, glycosylation, aptamer addition, hydrophobic molecule addition, polymer addition, and addition of unmodified DNA.

5. The method according to claim 1, wherein the anti-cancerous pharmaceutical composition further comprises a nucleic acid transfection agent.

6. The method according to claim 5, wherein said transfection agent is a lipid-based transfection agent, a polymer-based transfection agent, a magnetic particle-based transfection agent, an exosome for nucleic acid delivery, or a viral protein for nucleic acid delivery.

7. The method according to claim 6, wherein said transfection agent is a transfection agent comprising a peptide represented by amino acid sequences GGGGDD (G4D2) (SEQ ID NO:14), GGGGGGDD (G6D2) (SEQ ID NO:15), GGGGGGGGDD (G8D2) (SEQ ID NO:16), GGGGGGGGGGDD (G10D2) (SEQ ID NO:17), AAAAAAD (A6D) (SEQ ID NO:18), AAAAAADD (A6D2) (SEQ ID NO:19), AAAAAAK (A6K) (SEQ ID NO:20), AAAAAAKK (A6K2) (SEQ ID NO:21), VVVVVVD (V6D) (SEQ ID NO:22), VVVVVVDD (V6D2) (SEQ ID NO:23), VVVVVVK (V6K) (SEQ ID NO:24), VVVVVVKK (V6K2) (SEQ ID NO:25), LLLLLLD (L6D) (SEQ ID NO:26), LLLLLLDD (L6D2) (SEQ ID NO:27), LLLLLLK (L6K) (SEQ ID NO:28), or LLLLLLKK (L6K2) (SEQ ID NO:29).

8. The method according to claim 1, wherein the composition is for topical administration.

9. The method according to claim 1, wherein the method is used in combination with other anticancer agents.

10. The method according to claim 9, wherein said other anticancer agents are one or more anticancer agents selected from the group consisting of an alkylating agent, a platinum preparation, a metabolism antagonist, a topoisomerase inhibitor, a microtubular inhibitor, an anti-cancerous antibiotic, a molecular target drug, a hormone preparation, an immunomodulation drug, an interferon, an interleukin, a plant-derived anticancer agent, and a BRM preparation.

* * * * *

UNITED STATES PATENT AND TRADEMARK OFFICE

CERTIFICATE OF CORRECTION

PATENT NO. : 12,090,167 B2
APPLICATION NO. : 17/694982
DATED : September 17, 2024
INVENTOR(S) : Tahara et al.

It is certified that error appears in the above-identified patent and that said Letters Patent is hereby corrected as shown below:

In the Specification

Column 10, Line 7, Table 6: Please correct "$K_4\{e(CN)_6\}H_2O$" to read --$K_4\{e(CN)_6\}3H_2O$--

Column 10, Line 20: Please correct "miR-34a-Sp" to read --miR-34a-5p--

Column 12, Lines 43-44: Please correct "miR-34a-Sp" to read --miR-34a-5p--

Column 13, Line 35: Please correct "5 L" to read --5 μL--

Column 13, Lines 37-38: Please correct "miR-34a-Sp" to read --miR-34a-5p--

Column 13, Lines 57-58: Please correct "miR-34a-Sp" to read --miR-34a-5p--

Column 14, Line 25: Please correct "Jel" to read --Jcl--

Column 15, Line 8: Please correct "Jel" to read --Jcl--

Signed and Sealed this
Tenth Day of December, 2024

Katherine Kelly Vidal

Katherine Kelly Vidal
*Director of the United States Patent and Trademark Office*

SEQUENCE LISTING

```
<160> NUMBER OF SEQ ID NOS: 32

<210> SEQ ID NO 1
<211> LENGTH: 21
<212> TYPE: RNA
<213> ORGANISM: Homo sapiens

<400> SEQUENCE: 1

accugaauua ccaaaagcuu u                                         21

<210> SEQ ID NO 2
<211> LENGTH: 22
<212> TYPE: RNA
<213> ORGANISM: Homo sapiens

<400> SEQUENCE: 2

agcuuuuggg aauucaggua gu                                        22

<210> SEQ ID NO 3
<211> LENGTH: 90
<212> TYPE: RNA
<213> ORGANISM: Homo sapiens

<400> SEQUENCE: 3

ccucuugagg uaccugaauu accaaaagcu uuauguauuc ugaaguuauu gaaaauaaga    60

gcuuuuggga auucagguag uucaggagug                                   90

<210> SEQ ID NO 4
<211> LENGTH: 123068
<212> TYPE: DNA
<213> ORGANISM: Homo sapiens

<400> SEQUENCE: 4

gtgagtggcc ccgggagagg gaattgaggg ggagaaagtg ggaggatgcc ggcgcttcct    60

cctggagttt tgctgatgtt ctccagtagt gttgggagtc tatcaatgag ggagtctagc   120

tttattcacg gaggggggaa ggtgttaggg aggcctgtat tttgtaactt tttagctctt   180

tgtacgagta atgcaagtat gcaggtttct gtcggaggag tcttttctcc aaagtgaata   240

ctcgcacctt tctggccagc agttggcaaa gggaaattga ggaagccaga gcatatgtgc   300
```

-continued

```
gcacagaggc catctgtatc tgtaaccttt tcctggtact gtgggtgtgt gcggtgtact    360
ttttgtttcg gggtactctc catataggtt cccgaatgag aactacttaa cctgtggacc    420
cctgaaagta aaattccttt tttaaaaaac aacaacaaac ctgttttgag agaggttcat    480
ttcagtacct attggtacag gagttaacct tctcagttac tgggtccaat ttcatgtgtg    540
tcaggaggac actgtaacag atgtcagtta ctcaggaact tgagttgtta ggaatcacaa    600
cttacttggg gaagagcatt tatcacatta atcattttat aaaagttgtg atttttttccc   660
tttcaccccc cccttttttt ttttagagta acaaattaca gcactttttt atttggtttg    720
aggctttgct tttttgaatt atctttattt ctgtatcaat ttaggataca tctttgatat    780
ttaagtcagg aatgattttt tccttccatt attttaaagc tgaagtttat aaaacctttg    840
acttgtattt taggtatctt gtcagagtac caaattaaag gtttatgaaa gtaattaata    900
tttcatatac agaccttaag ggttaaacat agagcagaat tttatgtaag aagacataga    960
cagtagtata ctgagaattg tggtccgtct agacaactgt gggctcgttc tgtctgaagc   1020
cactgctgag agatactttg tgggaatgaa tgtaagcctg ggttatctc tcttttcgaa    1080
gttctccatt caggatcttg attagattaa tttaaaactt tctcaaactt aacaatgttt   1140
ggtccttttt tttaaagtaa tgagttctgc aagtttatta gcctgtgtat tatgtgacag   1200
ttcatttaca tattccatac ctgtgtccct aaactttcag gacacagtca gagtttgtgt   1260
ttcaagaatt atcaggacaa gcctcagttc atcttttctt aattttatgg actttcatta   1320
tttctaccat cagtttctcc aactgttgtc ttagaataat gtctttcatt tgaccacttt   1380
tccctcctct ggaacttctc ccactgaatt gtttttcttt agttgccttg ttatgctttg   1440
gtaaggaact ttaaattctg tcctttaaat gtgtactgac atgaaaatac tgaatagtgg   1500
atgtaatgtt agaatcagag tcacgtattc tgtttttcac taagatattg caaagagaaa   1560
tgtagtcatt ttctaaaata ctgtacccaa aatacagtag aagctgtatt ttgggaagga   1620
ggggaggaca aactaagaaa caaactatag tttgaatgta ggttgcactc tgtcaaagtt   1680
gcttactaac tttaggacct acttttattg cttatggatt ggttaaaaat tacggtattt   1740
ttttttttt tgagacagag tcttgctctg tcacccaggc tggagtgcaa tggagcgatc    1800
ttggctcact gcaacctccg cctcccaggt tcaagcgatt ctcatgcctc agcctcccaa   1860
atagctggga ctacaggcat gtgctaccac gcctggctaa ttttttttgt atttttagta   1920
gagatggggt ttcaccatgt gggtcaggct ggtctagaac tcctgacctc aaatgatctg   1980
cccacctcgg cctcccaaag tgctgggatt acaggcgttg agacaccgcg tcctgccaaa   2040
aaattatggt aatgttttat tgcacgtttg ggtagaaatg acaaagtttt tggggtccct   2100
gcctttgaga tgcttttact tgtaggtggt ggagacaatc aaacacaaat tgcacaaagc   2160
tataggagag gggggataga ccaatattta tctaagaccg cactggatgt tagatattgt   2220
caacttatag atgtgaatat atttttacat ttttcactag ggaaatgttg cttttggacg   2280
tgtacatata gaactaattg aagtattgaa gccaaatctg ggaaggtttc ttttaggaag   2340
aaaagagcaa gtggagacac aatatttaag acttttggaa ttgaaaggca taagggacag   2400
ataaaattac gaagctggtt tgaagggaat acagatagag gttgttgagt agtgttaggg   2460
tcagttgtgt ttgtgtagac acatgattac agttcaaaga agcaactgag aagagtgttc   2520
ctgagagtaa tttcagatga ctggggagaa attacatttt aggtaaaagc tgtatgcctg   2580
gattaggatt ttgtttttct agggaaccaa catttttatt atatcgtggc tatccagggc   2640
tatacagaag gaggagtgaa aaagaagatg cttagtgtgt tgaaagtggc ttcttacaaa   2700
```

-continued

```
aaagagttta gaaatgggac agtagacttt gctttggatg tgaaatttta gggcaacaat   2760
tggatactgg tgcagtttca aaacagcaaa atagtttagc aggtaatata ctgaaaatgt   2820
aaagttggaa ttattttcaa agtatttagg tttcccagag tactgatgga aagtgaagag   2880
ctgaaaagtg ggtattttta gttaggggga aaatctgaat gaatgagaca ctacctaaaa   2940
tagatgtttt agaagtggat aagagttgaa gttaaaaagg aatgagcagg ctttaaacat   3000
ggccaccagt ttagtcccag ggtatattat tctgtatttt tgaaacaagc taaaattttt   3060
tttttttttt aaatagggta tataggtccc ttgagattaa gttcagaaga gtatacttaa   3120
taataatttc attgttaagg aatttataaa tagaaggaca gatttgtttc ctcaaattca   3180
tgttttaaag ttcactgtgc attattatcc tacgtttggt cttgatatga cgaagtgagg   3240
ccaaaaatag ctgacagaga aggctgcttc ccttgttcac agttggtgtg tgtctttgtg   3300
tcccatacaa tggaggggat atccctgtgt aggcacagta gtgctgaaca tgcttttttt   3360
ttttttttcc ttttaaactt tttattaaaa aaaagcaact tggcatttaa aaaaatgtag   3420
acatttttgc ggcttgcatt tagtattgac tttaacagga ttaaggattg tgaggaagga   3480
aatatatatt cacacttttt tgtgttcctt agttggaatt ctgcaccttc ctagtagctt   3540
ctctgacttc ttaacagtga ttattcaaat ggcagaaact ctggggaaga gatgtttcaa   3600
caaggagata ggtctaaggt gattctaggg tgaaaatata gggattggat tatatgccat   3660
atggaggcct tctcttgtca tcctccactt tccacaacat tttttgtgca gtcgaagcca   3720
tgttcagatg aattttagaa ggcagccact tatagttaat gttatttact agtgaggaca   3780
gtgggaagag tggtaacttc atgtactttg ccttggcaac ttttggattg atagggaatt   3840
agagagcctt gagggtatat gtttgtgtgt gtgtgtgtgt tttagcaccc accagatgac   3900
cccaaaggcc atgcataggc tcatttcatt gtactttgga gatggttctt ggagaagtct   3960
tctggtgctt ctgacatctc attgtgtaga gaaagagttg gcaaactatt tttgtaaagg   4020
gccagttagt aaatatttta ggttttacag gccacatgat ctgtcacaac tttcaattct   4080
gttcttatag tgtgaaagca gctgtagaca acaaggaagt gaatgaatgt tgccgtgctc   4140
caattggccc ataggccgaa gtttttggac tcctggtata gacaactgcc aaatccacca   4200
acaaacagta tgagctttat tacactacaa agccaggact ggctattttt ggtggtcttt   4260
gttttctaga tgagatgttt ttctctgagt tcatttaaaa tgattctgca taaagcacat   4320
actctactgt acaaaatact tttgccttca tggtgatgaa aactatggat tgagggtcgg   4380
ggtgatacca tctttaaagg gatgcagcta aaaagtaggg actacctgca tttcttatct   4440
aaagataacc acagttggca tttagtgata tactggcttt gtatcatggc caaaagtatc   4500
tgtaaagaag cttgtgggca tacttttgaa accttctgaa aataaatgta aagcatttac   4560
ttcgtgtgta aaattagaag tgtctatggt tggtttgaat aatatgagtc aaattataag   4620
agcattaaag tttgatactg ctatctatta aagtcttaat ctcttgcagt ggctaattca   4680
gtgtgtagaa ttacacatcg caatttttgt tttgttaatt tcaagtacta gtgtatatta   4740
acaaatcact taaatcattt aaatgtgtac tttaaaaagc tttgatgtat atacatatat   4800
atacgtatat atatatatgt acacgtatat atatacacgt gtgtgtgtgt gtgtgtgtgt   4860
gtgtgtgtgt attttttttt tttttgtgac ggggtctcat tctgtcaccc aggctggagt   4920
gctgtggtgt gatctcagct cactgcaacc tccacctcct gggctcaagt catcctccta   4980
cctcagcctc tcgagtggct gggatcacag gcatgcgcca ccatgcccga ctaatttttt   5040
```

-continued

```
tgtatttttg atagagatgg gtaacaactt ttggattgat agggaattag agagcctcga   5100
gggtatatgt gtgtgtgttt tagcacccac caggtaaccc caaaggccat gcatcatgtt   5160
gcccaggctg gtctcttaac tcctgagctc aggtaatcca tctacctcga cctccctcag   5220
tgctgggatt gcaggcgtga gccaccacac ctggccagca ttgctatatt tttaagagtg   5280
aatctttctc acatgtgttg ttcagaaagt gtaattcact ttgtgcaatt ttacattaca   5340
gttaatatta aaatatttgt ttcatatgtc agcagatacc aacattggat gatggtatat   5400
ttagtttcat aaatcctatt tattttagga ttcccttgtt tatggcaggg gtggagatta   5460
ctcttgcaat aatgatcact ttttagttag tttgaaacct gcttttagtt tatatgtagt   5520
atttctacat attgttactt aaattgaact aacaatttac tttttaattt ttcttcttcc   5580
ttttaaaaaa agagtatata atctgacaat gttagtacat cttttagaag gtcactataa   5640
agttgctttc cctatttatt tggaaaggat tatttcctta ttattttaaa aaatctttta   5700
atttttgtct tttcaagtaa ttttatcatt gtcccaagcc taaggatgag tggcaattta   5760
aaagacacaa ggtgtgcatc ttctatctgc aaatactcca aacagaaatt attccagttt   5820
gttgatactt tgagtggacc agggaaaaat gtgtatgttt ttagtgtaac tgaattgtca   5880
ttacaaaaag atgagtaaag ttgctgttaa ataatgaatt cttgctgtta atttgtcctg   5940
ttcttagact ttcccccatt aagtataatg ggggaaaatg tacacacaca cacacacaca   6000
caaagtatgt atgtgtagat atacctagcg tattgtgcta gatgttcatt tctgcatgac   6060
tgctctggaa tttaggcaat attaaaagac cttacaaaat atttttaata tcacttaata   6120
tcctgtttta tgtcttaatg tacttttatg tttttgctgc tttctgatga tacctccttg   6180
gtacttcctc atgatacctt tcacagtatg tttaaatgga atgtattttc tcaaagtacg   6240
tgacattttc tgaacactat gggatatata tcttctagta attatatttt tacatgcaag   6300
tatctttaaa aatttcttcc tattacaact taagaattgt gaaacatttg agggagcatc   6360
tgcagtttga gcacttgatc tggatattgg aatgacaaac ttaacattta actaaatttt   6420
tctgaggtgt tcttttacaa tttttgagtt aacacttgat ttctgtaaag cagaaggctt   6480
ataagaagaa aatatgagag ccagtgttcg tcttgtatta tcctgccatg cacgtagttg   6540
aaaatcagaa acaaacagaa atgcacaaga gaccttattg cttgagtatc ttctgctctt   6600
cccccatcag acctaaggga cagctagtgg atcagtcaga tactgtgcag tttctgttgc   6660
tatgctgtgt cacctttgcc ctttctttct atctggaaga tagctactgg aaatctggct   6720
gtaagaaaga gatagcatgt ttttttcctc tctctctctg tgtgtttctg tctgtctgtg   6780
tacctgtacc tagtgtattg tgttagatgt tcatttctgc atgactgctc tggaatttag   6840
gaaatattaa aagactacaa aatattttta atattattta gcctttttctc tgagaggatc   6900
acatcctctg gctttggcgt tttcatctca cagcatctta aacgaacccg tcaatgttta   6960
ttatcagttc caaatgtgaa gtctcaaggc aaattgttgg tttgtttttg gaagaatgta   7020
tgtgtgtgtg tatatatatg tgtgtgtgtg tgtgtgtgtg tgtgtgtgtg tgtgtatata   7080
atttttaaat ttttaacaaa aattcctgat ctagtcaatg cttatgagag tgtgtgtggt   7140
ttgtataaaa ttattttttt tagagacagg gttgcttgtt gtcaccaggc tggagggcag   7200
tggtgtgatc cttgctcact gcagccgtga ccccctgggc tcaagtgatc ttcccacctt   7260
agcctcctga gtagctgagt agctgggact ataggtgtgt actgccacac cctgcaaatt   7320
taaaaaaaaa attctgtaaa gacagggtct cactatattg cccaggctgg ttctcaaact   7380
ccaggactca agcagtcctc ctgaaatggc ctcccaaagt gttgagatta caggctgggg   7440
```

```
ccacagtgcc cggtcagagt gtgtgtattt tttaacagcc ttttaggatt gcatgctttt   7500
tagggggggtg aatgaggggt aatataccctt tgcatgacat tctctaggtc tgagaaggag   7560
ttgcttcact aaaagtgtaa tttataatta ccaaatggtt gaaaacaggt ctacctggag   7620
tcagcaacag gcagctagtt tacttctcat ttacgtaata aaatacattc ataatatgca   7680
ttcagtaatt cataattcaa taatttcttg gcttcatggc cttggacaag ctatttatta   7740
tccttttaat tttggtggca tcacctgttg atggaggaaa acgtgtcctt tacatggtgg   7800
ttgttaggat taaatgagat aatataaagc atgcaaagct cttaatccag tgcctggcat   7860
atagcatttg acccatcagt gttaatttat taagttaaag ttgttttaaa gtgtgttgta   7920
gatagaagat ttaaatcagg ccttatatta agcccaacat ttaaattcaa cacttgagtt   7980
tgacaaataa tactgaagta attctgtgtt ttcagaaaca tctaaaactt cattaacatt   8040
ttattaaaaa ctgaagaaat gacagaactg ttgggctttt ttttaataga aaagaaagac   8100
tgatttgaac ataactggaa tttgaattta gtttcaaaga tctcagtagt gcatggacca   8160
gaaaagaatc cgtttttgaa tagttagtga ttatgatagt gactgtggtt taaattgccc   8220
atttagaaat agcaggatct aattcagtta tcagcctttt tagttgccca tctctttaac   8280
ccctggaaat aaaaagcttt aaaaaatcat taagaagttg aacggaaatt ttatctgtgt   8340
catttacatc tcaaattaag atcgaaataa ttttgtttac atgattctat tttaactact   8400
taattttagt ttttgttttt tcctgaaatt attagtatgt gggttttaaa aattcctttt   8460
tttgtgtgct taatatttgt taaatacaag attggttttc agaaatacct tttcttcgag   8520
tagggcataa tcagtgtttt attggccaat acaataaata aatgcttctt gattgttttt   8580
gtatttggaa agaaattcta tgttgagaac agttttggta tgctttcctt cattggctgt   8640
ttattgaata gaactgtata tttaaggtat atgaaaaaaa tctaagctag aaaaaaagac   8700
tgagatacat tcttggaaga aaatacttgc aaactatgca tctgacaaag gtctattgtc   8760
caacgtctat aagaacttaa atttacaaga gaaaaacgac cccattaaaa agtggacaaa   8820
ggacgtgaat agacacttct cagaagaaga cttacatgtg gccaacaagc aaagaaagct   8880
caatattact cattagagaa acgcaaatca aaaccacaat gagataccat ctcagactat   8940
tcagagtggc tactataaaa agtcaaaaaa taacagatgc tagtgaagtt gtggagaaaa   9000
gggaacactt atatactgtt ggtgggagtg taaattagtt caaccattgt ggaaatcagt   9060
atcgcgattc cttaaagagc taacagcaga actaccattc cacccagcaa tcccattact   9120
aatgggtata tacccagaag aatataattc attctaccat aaagacacat gcacacgcgt   9180
gttccttaca gcactaatca caatagcaaa gatgtggaat caatctaaat gcccatcagt   9240
gacagattgg ataaagaaaa tgtggtacat acacaccatg ggatactgtg cagccataaa   9300
aaagaaggag atcatgtctt ttgtgggagt atggatgaag ctggaggcta ttatccgtag   9360
cacactaatg caggaacaga aaaccaagta ccgcgtgttc tcacttataa gtgggagcta   9420
aatggtaaga acttatgaac aaaatgaata gacactgggg tctacttgag gggggagggtt   9480
ggaggaggga gaagagcaga aaagataact attgggtact gggtttaata cctggttgtt   9540
gaaataataa gtacagcaca ccctcgtgac atgtgtttac ctatgaaacc tttacatgta   9600
ccccgaaacc taaaataaaa gtttaaaaaa tatattcttt agcactgatt atcttgctag   9660
ctgtgacttc tccttttaag gaaagtttgc tttagatttt ggtgtaaatg tagaaattag   9720
atgggtttat ctgctagtgg ctctctagtt agatgattaa tgaatattct agtttaaaaa   9780
```

-continued

```
atttcagcat tttaaatact tttctttatt ggtaacgatt tggattatgc ttctagggat   9840
ctttacattt catagttttt caaaaaagac tttataatga gttcctggat gggaagaaga   9900
gcatgttctc tctagtttat ttgatttctt cctgattatt atgtatgtaa tactggaagg   9960
ttgtgtaaat aaatatttgg gttgtaagtt ttcttttgca tgattggtgg tctcttaatt  10020
gactgctgtg tgaatttgat agtataaact agaatgctta tacagtgagt ggggaagcct  10080
ttttctactg agtgttatgc aggtggattt ttccccccctg cggataaata ctaaactttt  10140
atattaccag atttagacat ttagacagga aacaaaattt cctttttttt aaaataaatg  10200
agcgggagaa gagagtgggg ttgtacagag gtggggagag aggcagtaaa ggagggagga  10260
aagaagaggc agatatcagg gagagtggct ccggaagttt tgagttcagt cttagtcaga  10320
ggtcacaccc tgttatttct ttgggttgtg gacatgaggt gttaccactt gttatctgtc  10380
accctttgaa atgatgatta gattattggt ttttattcat agcttttcaa catttgggtt  10440
ctttaaacca ttgaaggttt agtttgtatg ggataatcag tgttatttta gggtgggaaa  10500
atttccacca tacctgctag gagaagggga tggccaaaga gtttttgact tacagaggag  10560
ttttttgtt ctgttgtttt ttcctcattg actctatttc gctagctttg tctgagaggg  10620
gtgcttataa ttctatatgt gacatagtag ctgagaggca agctttggag ttgatagacc  10680
caggttccag ctctgctgct ttgtgatttc aggcaagtta tttattccat gtgtgtttct  10740
tttaaaactg ggatgataat aatagtacct gtttccctta tagagtaatt aagaggattg  10800
agtgagataa tgcatgtaag cctttagcac agtgtctgcc taagttagca tccagtaaat  10860
gttagctgct gcaataataa gaaatattat agtattaagt tattgttatt tctgtgaggg  10920
tgctggtttt ctgaatgctg agacattggt gatctttgct cctgaacgtg ttactatttg  10980
gaatactgcc tttattcagc agcagattca gttcagattt actgaacacc tactatgcca  11040
ggaattgatc taaataagca aaacaaaaat cctgctctct tgaaacttac tttctggtta  11100
ggagagacaa aatacacaaa acaaaataga tgatgtgtca ctcaggaaat ttggttgttg  11160
gactttgtct aagctttcat taaccaaccc tagcagtctt aacctttaca tactttttga  11220
ttgttcctgt tgctgtgctt gagagtgttt ggaggtaggg gcaccctaaa agcgtatcat  11280
agactagctt tattgtctcc agcttcagct tgatcctaat tttaaggcag ccttaaatga  11340
tagttttcat catttccttg acttactact taaattggct atctcaaaac tttcagtccc  11400
caaaacttgt atttcacatc attcagagag atgttgctcc tccccagctg ctcctctttt  11460
gctcttctat gccattttct taagaggagg ggatactaga agcatctttt tagatttatt  11520
ttctgactag tctaactgta tacttttctt tctcatattt tgtgttttct accctttatt  11580
tattgttaac tgatacattt aatttgctta ttttctttaa aatatgtgtt tttttggtc  11640
tctccaatta aattgtgaaa gtttttaggt cagggaccac ttttctattt tgaccttgag  11700
cttactctct tgaaaaaaag ataataccac ccagggatgt tgtgagacct caaagagata  11760
atgtgtgaaa ggggtcctgg agccagatcc ttaataaatg ttagtttctt ctttgaacca  11820
ctctagttgc tgaaactgct gtgcatataa tcagtgctta aaaaatgctt gttaatttat  11880
cttgaattga gtttgtgaac tttcaattgt cacttggtgg tagttttagt ttttagtgct  11940
agataagatt caaaatacta cttttcaagt gtcagatgat aaatgctggg tcattagtgg  12000
tagagctcaa cagtgattag gagcaggaac ttgagccatc attgtttggg ttcaagtaca  12060
ggctaccaca cttactggtt gtatgacctt tggcaagttg tttaacctcc ctcggtttct  12120
ttatctgtaa ggaggggaaa atgatatcta cccacctcat ggttacttct ttgttagtat  12180
```

-continued taaacgaagt aaatgagaag ctcgaaacag tgcttagtat ataacaatct ataacagggt 12240
ccccagggga catttggcac tatttggtga tgtttctgat ggtcatttgg gggagtgggg 12300
agagggaagg gtgctactgg tatctcgtgg gtagaggtta ggtataaaca aggtatagga 12360
cagcatccac aacaaaaaaa ttacctggtc cagaatgcca gccctgccaa gcaacattgg 12420
gaaacccagc ttagttcctt tgtataaggt actttgccag ttagattctg tatacatgct 12480
gattattgat aaagatgagt cacagacatg gataggcttc atttaacatt cattttaaaa 12540
gacagacatg taagaaggtt agtaggtttc atttcttttt aaggttacag ggaaagtact 12600
ccaaaattaa tctaaaagtc cttacacttt tttcagaaac tgagaaaagg ttccagatga 12660
attttactaa tttaattttt ttatgacgag ctattcatgt aaaagtgtat tatgaataga 12720
gggcttatga gatatgagtg ccgtagtgtg tattcataaa gtcaaacgta cacttaaaaa 12780
acaagtatca aggtaaatgg aatgatctat tgggggaaac cttggagctc tctctctttc 12840
catatgtttt attactcacc aagtcaaggg ctctttaact taggatcttg tttttctgtg 12900
tacacttttc ctgtttactg tttaaaattg gacccttact aaaaatacag aaaattagct 12960
gggcatggtg gcgtgcacct gtaatttcag ctactgggga ggctgaggta gggagaatcg 13020
cttgaaccag ggagacggag gttgcagtga gctgagatcg cgccattgca ctccagcctg 13080
ggtgacaggg cgagactcag tctcaaaaaa aaaaaaaaaa aaaaaaaaaa attggaccct 13140
taccattcct tgtccatttc aggagcctct taattgcctt gcttctgttc tttctctgta 13200
ttcccacttg aattgactct tctttgctgg gatccctttg ggatcccttc tagtccagat 13260
ccaatctacc cttcagagct ccttccaccg tccccttatt tctgggagag aattcagcct 13320
taatacccta aggatggaat ttgaatgtac tgacttttct gctatttaca gggttgtgta 13380
ttatctttgg aagaattggg aagtcatatc attttctgta tgttgtggtt caggtgactt 13440
gtttcacttg tatccaaaca ctggttgtgt gtccatgtat atacagcatg tatgtacttt 13500
aatgtctatt tgtatgtgtg tgtacatgta tattctttca tgtatatttg tctctacacc 13560
ttgctgtttc ctctgcttgg aatattcttt tcttttcatc tgggaaacat ttgtctcttc 13620
agaccctact taaatattga tctcctagga agtgtgtcct gattaatata actagaatta 13680
gttatttttt tccactggtt acccacagta tctctgtggc ttttatagca cttaacatcc 13740
ttatttgtat ttttcttttc tactgatctc tcagttcttt gagggcaaga gtcttgtctt 13800
agtcaacacc tgctccccca agtacctaac attcctgcca cattgtagac atatagtatg 13860
ttaacaaatg aatgggagag acaaaaaact ggaaagcttt taaataagtt ctatgggggt 13920
tggcaggagg ggagaccaca cattatcttg tcacctttgt ttccaagtgc ttagtgttgt 13980
gcttgcccat aggtgttcag caaatatttg ttgaatgaat tagaagcaaa tcccaggagc 14040
tgataaaatt ttcatgtgaa cttttttctt ctgcatttct agaaagcata tcctagaagt 14100
aaagtagctt agatattttg gaacatctta ttcttaaagt cgaccttcct atttttgact 14160
cagtagtgaa actttgatcc aatggatact tcctgaatag tgcttttggc tgattccttt 14220
ttcacaacat aggtccgttc tggtgttgag tttgttggaa agatgaatat gtagtatcat 14280
ttttacatca tggaggagcc atcattaagt aacagtgtta aataaggact ggtccccttt 14340
gcacatttgg gcccaaatta agtgagtatg tactcttaag tatgggtaat gattgaggct 14400
attgaggtgt aggaaagaaa gaggacaact ggaggtgaag aagtgaccta ctagatctct 14460
tttgcttttg gtaatgattg attttttttt tttttttttt tgagacggag tctcgctctg 14520

-continued tcgcccaggc cggactgcgg actgcagtgg cgcaatctcg gctcactgca agctccgctt 14580
cccgggttca cgccattctc ctgcctcagc ctccccagta gctgggacta caggcgcccg 14640
ccaccgcgcc cggctaattt tttgtatttt tagtagagac ggggtttcac cttgttagcc 14700
aggatggtct cgatctcctg acctcatgat ccacccgcct cggcctccca aagtgctggg 14760
attacaggcg tgagccaccg cgcccggccg gtaatgattg atttttttacc cccagttatt 14820 tttaaagaat tggcaaggaa ggagaggggt atgaatctag aagataagaa tgtagatttt 14880
gtaattcatg atcattatta ttaccatgta ttgaatgttt actgtatgtc aggaactgtc 14940
ctaaggattt ttacaaccgt tatttaactt agtcctcaca gcagttcata tgaaatagct 15000
actgatgttt tatggcaaag gaaacaaatt cagagaaatt tccaagaaca catcggaatt 15060
ttgacttgca gaactgggat tcaaatctag atctgtcata ctccatggtc tatgctttta 15120
atcatgcatg ctgtctctta agtttttatt gaaaatggaa agttgtactg acataggagg 15180
ggaaaatgat agaaaatcat cctattggaa ggcagattaa cagactcgtg aagaagcaat 15240
tcccagtttt atgtcattat acaaaataat tgtgaaattg aagtccgtca tttgaattga 15300
tttgcattaa ccctcatttt ttagtcttgc tcttggaatc atcatcagga caggtgtccc 15360
agatatgtta gcagtagaat aaatttatct aggcaaaatc tgtctaagat tatggagaaa 15420
actgatttta tatgtgaaat gtgttgttga gtgagagtta aatcttttga aggagattat 15480
ttcaggatga gcctcaaata cattatttag gatttgaaaa cctatggttt agcagaaaat 15540
ctgagaatca acatttgtta gtctcttggg tataaattgc ttaagtcagt gggtatctga 15600
ttattctttc tttctttctt tatttattta tttatttatt tttgagacag agtctcactc 15660
tgtagcccag gctggagtgc agtggtgtga tcttggctca ctgcaagctc tgcctcccgg 15720
attcacgcca ttctcctccc tcagcctcct gagtagctgg gactacaggc gcccaccgct 15780
acgccctgct aattttttgt atttttagta gagacggggt ttcaccgtgt tagccaggat 15840
ggtctcgatc tcctgacctc gtgatccacc caccttcacc tctcaaaatg ctgggattac 15900
aggcatgagc caccacgcct ggcttccctt atgtaatttc ttaaactatt tttgtttgct 15960
gatttggtgt ttgtaattta aaaaaaattt attttttctt cttttacata ctttgtagaa 16020
ctattcccta cccagtgagt ttatttatag atatttcata tttaattaat actgtgagaa 16080
catagttttt atatctgtat ttttgttttt tcattaggat atttaaaata atttttgtaa 16140
ttctgttacc ttaaaaagag ctaaacttag atgttggcct ttaaaaatgt tttgtgaaag 16200
attttctctt ggttccattt aaaatactgt atttgtaact atagttaaat acatttgaac 16260
tttgcccttt tcagaaattt taattatatg cctttataaa attttatcaa aagttacatg 16320
caaatactaa gtatagagtg ctgaagctga gcgtgatggc ttatgcctat aatcccagtt 16380
actcgagagg ctgaggcaaa aggattgctt taggccggga gttggagacc agcctgggca 16440
tcatggcaaa accttgtctc tacaaaaata aaataaatta gctgggtgtg gtggtgtgca 16500
cctgtagtcc tagttacttg ggaggctgag gtgggaggat ggttttgagc gtagtagttc 16560
aagactgtag tgagccaaga tcctgccact atactttagc ctgggtgaga gagcaagacc 16620
ctgtttcaaa tatataaata aataaaatag taggctgggt gcagtggctc atggctgtaa 16680
tcccagcaca ttgggagtcc aaggcgggtg gatcacttga ggccaggagt tccagaccag 16740
cctggctggc atggtgaaac cctgtctcta ctaaaaatag aaaaattagc tgggtgtggt 16800
ggtgcgtgcc tgtaatccca gctactctgg aggctgaggc aggagaattg cttgaacccg 16860
ggtggtggag gttgcattga gctgagattg caccattgca ctccagcctg ggcgacacag 16920

-continued cgagactttg tcttgaagaa aaaaagaaaa aaataagtat tgagtgctga atgatgttct 16980
ataaaagatt aaaaatgcct aagtggaact aaattctggt aaatagaatt taggggttgg 17040
ggtagaaaga atcagataag tacttcaaga ttttcagact ttaagtctaa ggctcattag 17100
tatcctctga cataatctac tacaggtttc ctttcttaga agtgaatgtt aatatggcac 17160
cactatacaa ataatatcga tatcggtatt tgagtgttta ttatgtgaca ggcactgttc 17220
tgtgtccttc atgtgtatta cctcatccag tcctcacgat agctctatga ggtaagtgtt 17280
gttaatatcc ctattttata gctgaaaatt tggcatagag aagttaaaca tggtcaaggt 17340
cccacctta gttaatagtg gagctgggat tgtttccagg cagtctggct ctagagcctg 17400
ggaccttaat ctttattcta tactgtctgt gtcatctgta aatttatttc ttatatatta 17460
tttatagaac agtgcctggc acacaataag agccatagaa gtactggcta ttttcattgg 17520
catttaatta tatatgaggt tggcagagca tgcattatta ttccatttgt ttatttatac 17580
tattaattag atagtagact ttattcagat ttctgtgttt ccttttttta aatagtcgag 17640
tttaccgaag ttcttagaaa ctggatgatt gcctccaata atgtggccat gctagatctc 17700
aaaattaact tttttaaaaa aaccacccct ccaactttat ttacacttcc ttagaaatgg 17760
ataaagacca agattgggct tctgttttga tatgtcattg gtttagaaag gcagaaacag 17820
cctggcacgg tagctcatgc gtataatcct agcactttgg gaggctgagg cgagtggatc 17880
gcttgagctc aggagttcga gaccagctgg acaacatggc gaaaccatct ctactgaaca 17940
tacaaaaatt agctgggtgt agtggcactt gcctgtagtc ccagctactt gggaggctga 18000
ggcaggagga ttgcttgaac ccaggaggtc gaggctgcag tgagccaaga tggtgctact 18060
gcagtccagc ctgggtgaca aaataagacc ctgtctcaaa aacaaacaaa aaaagcggaa 18120
acaaccatac taagtttaca gtattgtttg tgtgcctact tggtggaaga aataaattct 18180
tagaagttac actttcttta aaaaattaaa aattaaaaac tgtgcagtgt tgagattagt 18240
attaccgctt atcttgctga cttgtgaaat tgaattacat cacttataat aatgtgaagt 18300
tttagaaatt gttttgatga taaagagtag cagcctttaa gagaaataat ataaaccatg 18360
tttcctcaaa tctaaatggt catctgtatg gtattagttt tccatcgctc tacagaagca 18420
gtccccagcc tttttggcac cagggaccat ttttgtggaa gacagttttt ccgtggatgc 18480
ggggaaggag aggcagtggg gaatggtttg ggatgaatca tcaggcatta ggttctctta 18540
aggagcacct aacctagatg ccttgcatgc acagttcaca atagtgtttg tgctcctatg 18600
agactctaat gccacagctg atctgacagg aggcggagct caggcgataa tactccacct 18660
gcagctcacc tcctgctgtg cggccgggtt tctaacaggc cacggaccag taccagttgt 18720
ggacccctgc tctacagcaa attaacacaa atttagcagc ttatcttaca gtttctattg 18780
gtcaggaatt tgggtatggt ttagctgggt ctttcctcag gttctcacta ggctgaaatt 18840
aaggaatcag ccggggctcc tatctcttct gaggctctgg gttctcctcc aggctcaccg 18900
gttgtgggaa gagttcaatt ccttgttctt gtagatctga tgtccctgtt tgcttgctgg 18960
ctgtcagcca gggaccactt tgagctcctt agaggcccac ccccgccacc atgttcttgc 19020
catgtggcca agttattatg ttgtgtatga ctaaggaaga aaaatgctgg attaaaatat 19080
aagacaaatt cttactttat gtatgactaa ggaagaaaaa atgttgaatt aaaacatgat 19140
acaacacatt attgcttgga cagtgccttg caaaaaaaaa aaaaaaagag agttgtggtt 19200
attcttccag ccacaatatc tgcttcagaa atgtcaaatt tattttctac tgttgtgttt 19260

-continued

```
gtgttctttt ttgtaaacaa ctttttttgtt tcaatgctga atcatagtat tttacaggac  19320
atttaaaatt aagaagtaag cgtgacttct tattgtacta ctaaatgtac agaatttagt  19380
aataattatg gtgatataaa ctgccattac ccaatttgca agtgtacagg gaatgacagc  19440
tatgttgtga ctgccatggg caaatggtga tttgtaaagc attgttgctt ttttcccccc  19500
attttaagtt gattttattg agatataatt tatatacagt aaactacaag acatttctgt  19560
caccctcaaa agattcctca tgccccttca cagttaaatc cttccctgca ccctcgcttc  19620
aggcaatcaa tgatctgctt ttttattact acaaattagt ttgcattttt tagtatttta  19680
aacagtgagg aaaaaagagg agatggagac aggctatttt taatttttat attttcttct  19740
ttgttcttag agaaatccta gtttctttat taggcattag gtttattcct tcagtgtggg  19800
ggtaaagtga ttcttcttga agctttctaa gtatgtttcc tagatgttct tgacctctgt  19860
tttgcctaag ataacttttc tccagcatac ccagagttgg ctctcttaaa ccatacgtgc  19920
ttgtgtagct ccctcatcca tatttctact tattgtcttt tcaggaccgt aaacagaggt  19980
atttttgact tgacattctc agctcctaaa taatcttata gtgttactga ggcttttcac  20040
ctgtcacata cccccgtcct agtctctttt tgtgttgctg taaatacccg aggctgggta  20100
atttatgaag agaagaggtt tatttggttc atggttcctg caggttgtat aagaagcatg  20160
atgtcagaac atctgctttc tggtgagggc ttcaggaagc ttccactcat ggcagagagt  20220
gaaggggagc aggtatcaca tggtgaggca ggaaaggaga gaaagaggag agggggtgcc  20280
aagctctttt tatcagttct catgagaact tacagagggg aaactcattc attaccttga  20340
ggatagcaca agctgtttat gtggaatctg ctcctatgac ccaggcacct cccactgtgc  20400
cccaccctca acattgggga tcagatttca acctgagatt tggaggtgtc aaatattcaa  20460
attatatcat cccctagaga acatacctcc ccacccctga gaatctcaga atttcttgtt  20520
gagaattcat attacagtat gagttgtagg aaacatgaag gaaagatttc ccttctagtc  20580
agttcttata tttatcactt gtttcatgct ccttggtgtg tatagtgttt tcaggtgcag  20640
gaaatgctct gggaagaatg ttgcttctta gaacgtaaga gaaagggaac cccaagggaa  20700
gactcaaatg aagtccttaa aaagcccact tagcttcttc tgagacagca ttgtccaatg  20760
gaatgcaagc gagatagtta aatttaaatt ttctggtagc tatgttaata aagcaaaaaa  20820
agaaccagcc aacattaatt ttaataatat attttattta acacaatata tcccaaatgt  20880
tattttaaca tgtaatcaat atgaaaacca tgaagacttt gatatttaaa attcttattt  20940
taatactaaa tctttgaaat cagtgtatat tttatactta caagacatct gaatttggac  21000
ttagtcacat ttcaagtaag tgctcattag ttagtgacta ccttagtgga cagtgtagat  21060
gtagattatg aactttttag gaaaagacaa tagcatgtgg actccacaag aaattgtctt  21120
taacaactgt ttgactctca taggttaggg ctttagtgtt tcagaatggt ttctatggtt  21180
gagatgtaaa gtttttttatt tttataaagg taagtacatt tttatacatt ttcattatac  21240
aagtaatgtc attgttgaag agttggaaaa gtctgggtaa aagacaacaa attgtcctca  21300
cttcctcagt ccagagataa ccaatggtaa actttattga atttcctctt tgggaatgtt  21360
gctttttaaa atcaaagaga aaatagattt cttttttgtc ataattcctt cctgttcaca  21420
ttcagacata cattattatt gacaattctt ttacctcttt gtttaaattt atgtattctt  21480
tttctcgggc tgtatcctcc aatagggtct ctgtgagtgg agtactctgg agcacagtaa  21540
cctgaatggt gcttccctgg attagggtta acaatagaaa cttcaatggc ttttatgtac  21600
tcattgctaa accagtgtag ttgctttcta ttttaactat ctgcgatctc tttgcatatc  21660
```

-continued

```
ctgcagcttt tttagttatt gaggtataat ttgcatacca gaaaattcac tctattaaat  21720
actcaattca ggccggcata atttgcatac cagaaaattc acgctattaa atactcagtt  21780
caggccaggc gcaatggctc atgcctgtaa tcccagtttg ggaggctgag gtgagcggat  21840
cacctgaggt caagggttcg agaccagcct ggccaatatg gtgaaacccc gtctctacta  21900
aaaatacaaa aattagccga gcatggtggt gtgcgcctgt agtcccagct atttgggagg  21960
ccgaggcagg agaatcgctg gaacctggga ggtggaggtt gcggtgagcc gagatggtgc  22020
catttgcact ccagcctggg caacaggagc aaaactccgt ctcaaataaa taaataaata  22080
aatattcggt cgttttcatt gtattcacac agttgtgcag taattatcac tattaatcca  22140
gaacattttc attacctcaa aagaaccctg atgctcatta aggagtcact tcccatttcc  22200
tctttgcgca gtctcctggc aaccactaat ctacttccta tctctatgga tttgcctatt  22260
ttagacattt cttataaatg gagtcataca gtacatggcc ttttgtgttt ggcttctttc  22320
acgtaacacg atgttttcag tgttcttctg tgttgtagca tgcatgagaa cttcattctt  22380
tttaggactg aatagtattc agttgtatgg agggtaccac attttattca tcagttgatg  22440
gactttgggg ttgtttctgc tttttgagat cacattcatt cttcaagaac attaatttct  22500
taatatcgtc ctccattctt atcaaagctt tcagtggttt cctgttgtct ataaacataa  22560
tagaaaaata tttagtttgc attcagtctt acaaagtgta acttcaagtt actttctttt  22620
ccactcttat tttccatctt gttgttgttt actgtgtcta aaatatgtgc tatatatgaa  22680
ttataaaatt atgtagacaa tatagataac cttgtcatct gatctaattt ttaaaaagtg  22740
aatttgaata ctgccaaact aaggagtatg tgtagtatgg agaatttgag aaagacaagt  22800
atcagtaaag aagaaacagt atagtaaaac aaaatttttt tctgccttgg tccattgaaa  22860
gaaatattta gtttcatata atgtgaacaa aaaccttaat tttgaatgaa catttgatac  22920
ataggaactc attcaaatca ttgattttct ggttaacttt gttagtagtt tgttttttc  22980
tgagtctttt gttttaatcc agatagtcag tctttttctc ctttttacat gcttgaaatg  23040
gtaaaaatga aatattttta cttattctta aaaatatttc cagaatgtct tacacacaca  23100
tacacttaga aacaaataca aatatatagt gatattctct cacattttac agagaaaagc  23160
gtagtataca tactttgttt tttaatttca cagtagatct tagaggtctt ttaatattag  23220
catactgaga actttctcat ttttttcata atagtattgt ttattccatt gtgatgaata  23280
tgctattgtt tttgaaacta gtcccatatt ggtggacatt taggttgttt ccaggtccac  23340
tattacagat aatactacag tgaataagtt tgtacatgta tcatttcata tgtatgccaa  23400
tatttctgca ggataatttc ccaaaagtga aattgctgaa tcaaaagata tatccacctg  23460
aaatttgatt acccatattt ttaagcataa aggaagagat aaagggaaat aaatagaaaa  23520
aaaagaaact atagattttc aaaaactttg tttatagatg aaaaaatgga ggattagaac  23580
ttttaagtaa ttgtccatgg tcatgcactc cacagaggac tgggcatggt gggattcggt  23640
gggggggcg gggggctgtg tcaggatgct aacccaggtg ttcctgattt taaataagct  23700
gctatccttc ctgttatatt catactgcat gttatgagca aaaggggaga gaagtcgcca  23760
actttttgga gaaaaagaat aaaatcccag actttatttt tgggatcatc tgaggtggga  23820
agatggcttg ggcccaggag tttgagacca gcctgggcaa catgaagaga ccccctgtct  23880
ctacaaaaaa aaaaaaaaaa aattaaccgt ggtgtttgag gcttcagtga gctgtgatca  23940
ctgcactcta gcctgggtga cagaatgaga tcctagtata tgtaggtatt taatgtatat  24000
```

-continued cgaaggcagc atttcagatt ggtgggggag aagatggatt atttggtaat ttatattgca 24060
gcaactttct attcatttgg ggaaaaagcc ctgtcccttg ctcttactct ttacataaaa 24120
aataatttaa aaatgaaagc aaaaggtaat atcgaaggat gtcgtgaggt tagccttatt 24180
caatagactg acctcagtga gtactgaact catgaaagtt tcattttttt cccagtcact 24240
gtcttttgca ttttccttaa ttgattttta acatcacctt ggattaatct catagctttc 24300
ccaatatgtt tttagttatg aaaagtctat ttctcctctt gccccgtatt aggcttgacc 24360
tgtggctgga gagatctgtg gtactgtttc atatgtaccg ccctcctctt tctctcctcc 24420 ctttttttact tgttctgaaa acaatgagta aggttaaaaa attatttttc acaaacatga 24480
aaaaggttga taatacgtaa gttttgaata tgggggaaag ttactctcat actgttgttg 24540
ggagtataca tttttgtggc ctttttggag agcagtttga cagtatttat caaaataaag 24600
tacacaggca tcttgaatca gcagttgttc ttccaaaatt tagtagtaca gatatactga 24660
cataacttta cttgaaagaa gaatcctttt tataacttag tgtttattga caagagaatt 24720
agcatttaga gtcatttatt attctaactc ttctaccaaa atggtgagat gtgttgtaat 24780
ttactggacg tttaggttgt tcccaatttt tttgtaagta tgaaaaatgc tgcagtgaac 24840
atctttgtct gtgtgctacc cagtcatcac tgttgagaat gtttcttaat ggctatattt 24900
aggtaagtgt tatttccctt tatttcccct cttatacttt aaggagcaca ggagatctca 24960
gttttaatcg cagctcaatt gcctaaatgg atgtgtgact taaaacaagc tctttaacct 25020
tactgagcag gaggttctgc agatatgggc ctctcagact attttatagc agtaataaat 25080
ggactaccta ttgtcacatt cttcatgatc ctgtagggag tatgtgtcag taggacaacc 25140
cattgagtga cagtcctaac tttcttggtt cctctccctc attgtgaggt cattgtttca 25200
caattgtata tacttactga ttcaaaaaac aactccaaca cttattgagg ggtagtactg 25260
ttcccagttg agaattactg ttgtaaaaat tttggcagga attatataag attattcatg 25320
attgttatcg acttatcttt attccttcat ttttttttaa agcaggaagc aataatagtt 25380
tacgttcgtt aacctcaata tctactctaa aacatgttgt ttttcttgtt attaccatga 25440
aagtctgggt taacaggaga cgagactagc ttcttcacag atacatacat taatttgaca 25500
ttatagaaaa atgagactgt atcctgactt gccagtttgg ttttgattgg tggtttcacc 25560
ttttttttta gactcaggaa aacggtggca aaaatagtat aaagggtaaa ttctcatatg 25620
cccttcattc aagttcccaa aatttaacat cttatgcagt gacagaaaaa ttatcaaaat 25680
caggagatta acattcatgt aatactgata gtctacagac tttattcaga tttcacccat 25740
tttctcacca atggcctttc tctggtccag gatcacaata tgaaattatt cacgtgttgt 25800
attttagtta tcatgttttc ttagttttct ttaacctgaa acaattccag tctttctttg 25860
ccttttgtga ctgttatact ttggaagagt actggtcagt aattttgtgg aatattgcac 25920
aatttgtgtt tgtatgtttt cctatgattc aattaatttt aagcattttt gattaagaat 25980
actgcaaaaa tgattttatg aatcttattt agaggcacat gatgctgatt tgtccagtta 26040
tcagtgatac taattttcag ttcctttcgt taaggtggta tcaggtttgt ccactctagt 26100
tgcttttttt cctttgtgat tcataagtag tgttgattca gattctaggt taagaaaagg 26160
aaaaaaaaaa gtatcctatg ggaaggtact taaaaataag tactttggga ccaggtaatt 26220
aacatttctc accatactct accaattttt aacttccttg ctgttttttt tttctttttt 26280
ttttttgcag tggcacgatc atgagtcact gcaagcctca atctcctggg ctcaggtgat 26340
cctcctacct cagcctgtta agtagctggg actgcaggtg cacaccacca tgcctggcta 26400

-continued

```
atttttcata ttgtttgtag aggcgaggtt tcatcatgtt gtccaggcta gtctcgaact  26460
cctggactca agccatcctg tgttggcctc ccaaggtgtt gggattacaa gcgtgagcca  26520
ctgcctggcc ccagacttta acttttattg atgattttgt catggtgatt ttctgtttcc  26580
atcatttctt ctgtatttac attagtggtt tttggtaagg aagaactttc ccttgttatg  26640
tatttattta atgttttatg tatatcagaa tggactcgcg gatttttttt cccctcttat  26700
atcagatgga cttacagatt cttctatgga tttcatctat tatcatcatt atttattttg  26760
gtgctctaat tatcccaggt ttggccccat gaagcctctt caaggaggtt cctggtcctt  26820
ttgacatgtc tccatcattt tgtgagggct taactttttt tttttctttt tgagtcaggg  26880
tcctgctgtg tcactcaggc tggagtgcgc agtggtatga tcatagctca ctgcaacctg  26940
gatttcctgg gctcaagtga tccccctgcc ttagcctccg gagtagctag gactacaggc  27000
caggtatgtg ccaccacacc cagctagttt tcgccttttt ttttttctc caatagagac  27060
agagtcttgc tgtgttgccc aagctagtct taaactcctg gcctcaagca gtcctcccac  27120
cttggtctcc caaagtgctg ggattatagg catggaccac cacacctggt cagaaggctt  27180
aactttctag tagcgcaaaa tgttctagtc tcttcttgtg cttttctctg ccccagccat  27240
gaaatcagcc atttcaccaa ggaatattga ttccttttac tggaaatcgg aattcttcca  27300
ttccccctgc ccccagtact tgtatcttac catcttttta aaagtctttg tgtcttagaa  27360
ccgtgttaga tgatctggac acattaccct gatgtacaga aattagttta tacacggtaa  27420
ttctttttgt agcagactgt ttaatttgta gcagattcat tttgcactga ttaatcctgg  27480
aggatttctt cacaagttac attgtgtcaa atatgttatt tcatgggaac acaattgaat  27540
tttttcctta attttgttcg gtatttgata ataacaattt aaaaaacttt tctaagagct  27600
tccttctaat attatatgat ataggaatgt ttacatttct catttattta tttggtgtag  27660
tgatctcaga agttttttta aaagaaaaat cttgactttg tctcaggtac tctcagttca  27720
cttccatgtg ggagggtcat ttgccatcca tccagattac ctttttgatt aggcttttca  27780
gtgtctataa atatttcggt cttttctgat catttaattt ctaatacatg catatgctcc  27840
tatgtataat aaatagacaa cttcaaattt gcagtttcta gatggttgga aaagggaaac  27900
attgtggtgt gtaatttatc agccatcaga tcctagatat ttgagatttt aactaagcaa  27960
ggtattagat agaccatgtt gttttggctt cacagaattc attcatattg tgcattacac  28020
aatcagtgtg catattgcac attgatttta tctgtaagtt gtctttatca gtggttctca  28080
aagtgtggtc ccctgctagt atagtatcag cctcacattg gaactggtta gaaatgcaga  28140
cttctcagga tccacctaat tgcagtagtt aattttaaca agcccttcgg tgatcctgaa  28200
acatgttaca gtttgagaaa cactgctata atacgtttca tttaaattgt ttcaggttgt  28260
gggggtaggg aataagacta ccaatttatt catcttctgt gcaatattac ctgtttacct  28320
aactcttaga gatattaaga tattttgaag aatgtgtccc atgagattat aatggaactg  28380
acaaattcct attgcttagt gatatcatag ctgtcatgaa gtcttagtgc tgtaccttac  28440
tcatgtgttt gtggtggtga tggtgtacac aaatcttctg cactgccagt cgtctgaaag  28500
tatagcacat ggccgggcgc ggtggctcac gcctataatc ccaacacttt gggaggctga  28560
ggcgggcaga tcacaaggtc aggagattga gaccatcctg gctaacacgg tgaaaccccg  28620
tctctactaa aaatacaaaa aattagctgg gtgtggtggc gggcacctgt agtcccagct  28680
actcaggagg ctgaggcagg agaatgacgg gaacctggga ggcagagctt gcagtgagct  28740
```

-continued gagatcgtgc caccgcactc ccgcctgggt gacagagcaa gactccgtct caaaaaaaaa 28800
gtatagcaca tacaattatg tacagtacct aatacttgat aataaaggac tgtgttactg 28860
gttgatatat ttacaatact gcactttctg ttgttacttt agaatgcact gtttgaactt 28920
taaaaaaata aattcacttt gggaggccga ggcggacgaa ttgcttgagg ccaggaattc 28980
gagactagcc tggccaacat cgcaaaaccc tgtctctact aaaaatacaa aaattagctg 29040
ggtgtggtgg tgcacgtctg taatcctggc tacttggagg ctgaggcacg agaattgctt 29100
gaacctggga ggcagaggta gcagtgagcc agtatagcgc caccacactc cagtcttggt 29160
gacagagtga gactctacct caaaaaaaaa aaaaaaattg caaaacagcc tcaagaaggc 29220
ccttcaggag gtgttccaga aggcagcact gttgttgtag gagattacag ttccatgtgt 29280
gtgattgcct ctgaagacct tccagtggga cattatgtgg agatggaaga cagtgatatt 29340
gatgatccta atcctgtgta ggcttgggtt attgtgtata tttgtgtctt aaaacagttt 29400
tgaaagttaa aaaaattttt tttaaaacag gaaaaaggct tataaaataa ggatataagg 29460
aaagaaaata tttttatata gctttactat gtgttttaag ctaagtgtta ttacaaaaca 29520
ggcaaaaaat taaaacgttc ataaagtaaa aacgttatag taagctgagg ttattacgga 29580
agaaagaaaa aattttaaaa taaacttagt acagcctaag tgcacactgt ttataaagtg 29640
tatggtagta tacaataatg tcctaggcct tcatatgcat ccacccccaac tgactcatct 29700
agagcacctt ccagtcctgc tagcttaatt tatgatacag atgcaccgtt ttacatttta 29760
tataccttat ttttaatata ccttttatat atttagatgt gttaatatca ttgtgctaca 29820
gttgcataca gtattcagta cagtaacatg ctgtacaggt ttgtaacctg ggagcaatag 29880
tttataccat ggagatttgt gtaaaagcac tgtgtaatat tcacacaaag aagaaattgc 29940
ctgacacatt tctctgaatg tatctttgtc atgaggcgat gcgtgactgt ataatttgag 30000
ccacacatgt tattttaaaa attgcaatac ccttattaat gtaaaaagca gttgaattaa 30060
ttttaagata tttagcctga tggagccatg atattaccat ttcaacataa tttataaaaa 30120
aaattgttat tttagattct ctttgtacca agtttttgaa atctggtaga tattttatat 30180
ctcaatttca acactaactt tttaccggaa gtaattgatc ttcctttaga tttcataaag 30240
tttatggttg gaaaagtaga ttcacatatc taaatcgttt cagacacact taagtatttc 30300
gctacctgaa ttaagtacca aaaaataatt tttctgtaat atttgcatct aaattggtaa 30360
aactggttca tgttttttag tagaatgtag tagactttga agcaaaactg tatccatttc 30420
aaaattgagc tactgaagtt aagcaaattc atgaactctt gtgtcaactc cgtattactg 30480
acattatatt caaaaggaga ttggatgtta ggcaaatcta tattaaataa agtgtttttc 30540
aatgattttt ttgtaatttt tgcagccact ttgcaaaaca ctgtcaatta aaatttatat 30600
atgttgattt atgttagaac aaagtgtaaa atcttttttta ttggtttgtg ttatgaaaac 30660
tttaaatttc aatgtaaatt tataagaaag ttcttataaa atttctggca taccttcttc 30720
cagtttcttt ttattttact ttttcttgtg ttagcctggt cataaataaa ctctaccttt 30780
ctttggtgct tcaagttaag cttgttcata ggcattgaga tgtaagtgag gaaacaaaag 30840
aatactgcca tttttgtctt ttattactta atagtgaaaa gcatctcttt ctaaaatcag 30900
agttgacatt agagtagatc tttgtgaagt tattccacta tacccagtga gcaaagaaca 30960
cagatgtttt aaatgtattg ttttttattt ttttaacatt tccatgaact ggctaggatt 31020
catatttttg gcatgtacat actgaacaat tcaactcttt acatagggct tttcatagtc 31080
tgtttcagaa agctgaacac agatattttc aatgtgtatc atacagtgga ataaaggaat 31140
aggagaaaca tcaatttttg cttttaaaat tcctaacata gctggagctg tctgttgtga 31200
tagaaactaa ttgtttaata cctagctgaa attctttgac agaggtaaag gattaaaaaa 31260
tatctatgcc actcttgatt tttttttttt ttttacagct acatagtgac aactttttct 31320
taagtttaga agttctttca aataaatttc acctaaaaga tttaattggg gccgggcacg 31380
gtggctcatg cctgtaattc cagcactttg ggaggccaag gcaagtggat ctcttgaggc 31440
caggagatcg agaccagcct ggccaacatg acaaaacccc atctctacta aaaaatgcaa 31500
aaaattagcc gggcgtggtg gtgtgcatct gtaatgccag ctacttggag gctgaggcag 31560
gagaatcact tgaacctggg aggtggaggt tgcagtgagc cgagattgcg ccactgcact 31620
ccagccaggg caacagagcg agactgtctc aaaaaaaaaa atttaataag gtagtgtctc 31680
ttatatcaca tggctcatct aaagctaaag ggaaatagta atttttcaca ttttgaatct 31740
gttgattttt cgtattatta gaaaggtctt ccatatgatg gatggtgtct taattgaata 31800
tcttccacgt gttgtaaagt atctatttta gtattcctca taattttcta acaaaatttc 31860
tataattgaa ataatttctt taccatctct ttatgtaaat gtgattttct ttcttttggc 31920
gcaagaattt aagccagttt atagctgacc agagttacaa gcccagattt gttaaaaagc 31980
ttttaaacac gtttgttgta catttacttc tgacattgtt tggctaattt tgttgctttt 32040
cttctgattg tagagcagaa agttcttata aaattcactg tgtatttgtt gaaaatgtct 32100
cctaatattg tctactttac ttgtaaaact ttaaaaccca agaaatagct tttaattttg 32160
ctctgtcaca gctaattgta attgtcattc attagaaaat ttctagcata ccttcttcca 32220
gtttcttttt actttactgt tctggtggta gcattagctt ctgtatctct acttgattgt 32280
gtattgctgt aatgccttct ttttactttt aaaaatgtgt cctcctcttg tccattcatt 32340
tttaaagtaa gaaaattaat tatattcaaa atattaaaat taaaaaaaat aaaaagtatt 32400
gcgattgagt taccagttgt gatttacata ggcatcactg caacttgtgt tatttgtgaa 32460
aaacgtattt aagtaaacgc agtacggtgt tagattgatg agtagaaaaa tactcattct 32520
aactgtaaat tagttaattt ttactgacta gatcagtatt tttatgtgta atactagaaa 32580
tgactcactg tatcctgaga tgtggagtat aatatgcagt acagtggtca cagtgaaatg 32640
tagtactgcc aaaagaataa aactttcttt agtagaagga cattttacac agcttcagct 32700
tttaaattta aattaagtac aactaaataa agctaaaaac tcaattccct ggtaacacta 32760
gccacatttc aagtgcttag tagtcacatg tggctaatag ctaatatatt agaaattaaa 32820
ccttttgaga gttggttatg tatgtgatta aagtattttg gttacttggg actagagatt 32880
acagtcattt ttgatcaggc tgatgtcata ggaacagtac caaggggact tctgaatcaa 32940
gcaccctaga aagagctact tagaactact tgcattttct ttgtggcatc tcttataggc 33000
atgaaaaaat ttcaaacatt tttcatggat aaaaggattt aatcagaaaa gcatttggat 33060
atacatattt gaaatcatag cttgcctgta tgttactaga gtagttggag agtggaaaag 33120
tatctatatt ctaaagactg tttcatcatt tgggtgaaaa accaaaaaaa gagagtaatt 33180
ttgtttaata gctctttcac aaataaaaaa aagaatgttc atctgtagag acctatcgag 33240
atctcatcag gtttacaaca aactttagat tagcaagctc aatttcagtt gacatggatt 33300
gtggaaagat tttcagtgga gctcagatat ttaatatcct gaatttggat gaatatacaa 33360
tttctaaaat taagtacttc aactcctctg tggttttaaa accagtagtg gccatatctt 33420
gactagttat taaagcacca accttttttt ctttattact ttgcttttat cctttgagca 33480

-continued

```
agttaggcaa taagttctcc atgtttttga tttctacaga agtaaatgaa tgttattgct  33540
gatgtttatt tcattctgtc ttgatctcat gatatgagaa tataaggaga tgtctgaaaa  33600
cttgttttaa aaatcctatg aagcataagt tcatgaataa agaaggaagt ggaacttgtc  33660
ttgagagaat ttgcctattt agatggtttc caaagtgcat tctgctagtc actagagatg  33720
gtccttgaaa gagttctgta attaagtttg aagaaacact gtgtaccata ataatggcct  33780
attgaatatt ttaccatgca cattaatata tcaaaggctt tgagatatct tacaagaaag  33840
aaacttgcta aagcttgtct tcctgcatgt cttaagcttc ttccacagtg actttaagtc  33900
ggacttgtct atcctgtgag aaatgctgcc ctctagaggc acaaattcaa ttgctcttaa  33960
atttgagtac cataatgctg cctgatctta gtgtgaagtt gtgataatta atattaatca  34020
aatgcatggt aacaaaacca aatagaagaa atcttatgtt gcttaatttt aagaaaatat  34080
gaggaaacag aattgcaatt tataaatacc cactttttaa attgtacatg tgatattttt  34140
ggctgctaat aatcttttga atacatttct gtatatgggg aattgcggac acatagtact  34200
tcaagtctcc aaactctgag tctctcctgc tagcagaagc catccttccc tgtgttaaca  34260
accttgctta agacagttac catccatggg gaagctagtt tcctcatacc ccttcccacg  34320
atactcatgt ttccatacct gtaactggag tcagactata tcatgctgca cctttgcagt  34380
cacaatggga agaaaaggat tatatgtaat ttttttaaag ttttttttt ttttttttt  34440
ttttgctgac aaagcagcaa aacccttcagg aatatgtaca gaaatgggtg atgatgatga  34500
tgtgagagag aaagaaacat gcttttgcat ttggctgaat gtattggtat ggtgcagtta  34560
tcagagattc tgaattcatt gttctcgttc aagtagccag gagtggttct aattgtttgc  34620
tcctttggtc tcagcattga cttatactaa atgaagttga atgcctaaaa actcatagca  34680
taatatagag gaagaagtca aaagattaaa ggaaatagaa ctgatggagt ggatttatca  34740
ctgtgaccat tcacttacct cccctattcc ctctccagta ttctctacta agaggtctgg  34800
aagacacttc attcaccaac ctaatgagaa atactttgag ggcagtgcca gcatatatga  34860
aaagtaattc aattgctttt gtctgtaggc tggaggagat actttcattg aaattgtctt  34920
ttttacttca gggggtgtgg ccagattcta ggtaaggtcc aggcatcatt ttcataaggt  34980
agcttgacag gcatgatgat cagagatgca ctgacttgaa ttctttttgg ctgtgactaa  35040
atgatcatgg atccctacgt ctaaaataga gaggaagcct attaagatcc tactttatct  35100
gtatgagcaa aaaattttag gtctcatagg agaaggcctt acttgaacta ccataagagt  35160
gagttggcca gcctgggcaa catggtgaaa ccctgtctct acaaaaaaca caaaagttaa  35220
cttttgtgtt ttgggcatgg ctgcgtgagc ctgtggtcct ggctgctcag gaggctgccc  35280
ccttttttgca gtttacttca tgggttatat gagaaaacag gaaggagggg gatatcaccg  35340
agagattctg atattggagc tgtgtgcaat aactgataag tctctggttc ttacctccat  35400
atgaggaaca gagagagtct tgtttgtaca aggcttagtt ataatctgtc aggtttgagg  35460
atcttgattg gaagcataga cttgatctgt atttgtggtt tctcatttca aatagcctct  35520
caatgttgga taaatttgca tgttcatgtt ttatagagtc agaactcaat ttcctagtat  35580
tccttgcagc tagggcacaa gcatatgacc taggctttat tgatcagatg catctgtgta  35640
agacatgaat tcagggtcag agaaatgcag ggtaacagct cttgcctgga attgctttct  35700
aatgtgcatg ttgagtgaca agatattgag ctgtttagag gtagcagtga cagagatact  35760
agtgagcctt gttgtcctag gctcagcttt catggtacta gggctgaagg atgggaacaa  35820
tttggtgggg agacttaggt atttttcctg gcatcatatc tccaagtgga ttcttcagtt  35880
```

-continued

```
ctctgataat tcttggaatc ccctaatata ttaataaatt tattttctct tgaaaccacc  35940
tcaaatagat tctgtttata gcttagagcc ctgattgatc gtctaacttt aaagatttta  36000
tttatcgtca aaatatttta tttttctaat tgagatctaa aaattgtcaa gcacttatac  36060
tctatttttt cccttcctag agctctgcaa tcctttgctg tcattttttc ttaccaggaa  36120
tgccaatttt tgtacctttt gaattgcttt ttcttctttg ctacttggct tgagctccac  36180
tattgttatg aaacctttct tataccatcc cagcagcctg atggattttt ttcttcctct  36240
gaattccagt agcacttgtt tagacattaa gtgcaaggtg tttttttgtt ttgttttgtt  36300
tttctgtatg catcttagct tccgcactaa atgataagct ccctgaaaac tagtactatg  36360
cctctttata tcgcttgcat tgtccaacag aatgtcttgc acctattaga ttcaaggttc  36420
agcacagtca ccctcataat atatagtgat gagagttgct gagaatcaca gtgatgccag  36480
gctgaatgag ctgagataat aaactagtta gatgcatagt ctggccatga ggcccaattt  36540
ccatcttcct caaggagtct gagacttgcc tctcagtagt tttcgttagt aggtgatcat  36600
atcttctgaa ttactgtctt cttaatgttt tatgagtttt tttttgcctt gacaaaagcc  36660
ttctatttct ctcatgcttc ctagttcctt ccattgtgcc ctctgcaatt tcttttcact  36720
aagcttacta tttgcagtct cttaaaattt gtgtaaatta tgaaatcaaa gatacaaaga  36780
aaggacagaa agtagtataa caaacacctg tgtatctaac ctcagggtca agcagatatt  36840
aaccttttgc ctcgtttgat ttccttttaa agttcttccc tccccatact tttctccctt  36900
ctttggaggt actcattatc ctaaagtcct tacgattatt tccctgctgt ttttgtacac  36960
ataaaacatt tacacaaaag atgacctgtg tttttttcta gatgtgttca tattgacatg  37020
tgtagattta gttcattcat tgtaactact gtttagtttt ccaggttgaa taatgctaag  37080
ttttatagag ataatgcagt tctacctttt ggcaaataat attgtaatgc tcgtacatag  37140
gtacttactg taattttatc taggatagat acctgaaagt agaattgctg aatcacaggg  37200
ttcaggtgcc actttatcaa gtattgccga gtccagtcca aagtggagct accattttat  37260
acccattaac atgtttccac acttttttttt atcaacattt aattttatct agctatgatt  37320
tttttgccta tttgaaagat gagaaatgga gtttgatgat tttcattttc attactttga  37380
tttatagtaa agttgaatgt ctttgcatag tttttgatca ttctagtttc ctattctgtg  37440
aatcttttat gttctttgct gattttttttc ctattgggta ttgaacctta aattgatttg  37500
tggtgattct ttttataatc tggatattaa tggttttggt aatatgcatt gcaagtatct  37560
catagtgtgt gtgtgtgtgt gtgtgtgtgt gtgtgtggtt tttttttttt tttttttttg  37620
agatggagtc tcactctgtc tcccaggctg gagtgcagtg gtgcgatctt ggctcacaca  37680
aattctgcct cccgggttca agtgattctc ctgtctcagc ctcctgagta gctgggatta  37740
taggtgcccg ccaccacacc tggctaattt ttgtattttt agtagagatg ggatttcact  37800
gtgttgtcca ggctggtctc caactcctga cctcgggtga tctgcccgcc ttggcctccc  37860
agagtgttgg gatgacaggc gtgagccatt gtgcccggcc ttcgtgtcgg tttttaacat  37920
tgtttaaaag tttcagattt actacatgag ttcatttgta gaatctctct tctgtatcat  37980
agcttctttg gtctgctttc atgtctttac aatattgtgt taattttaat agttttgata  38040
taaatcttgt tatctgataa ggtgaatctt ctctcaatga aaattttggg tcagctaatc  38100
atatttcacc ctgaccctaa tgaaaattta acagaaaaca aaccctgttg gaaatgtgat  38160
tggaatctca ttgaatttac aggttacagt ggggatagtt gtcaccttta cattggttga  38220
```

-continued

```
ctgtcattga tatttctgtt caatacagtt ctattttttt cttttttctt tttcttttttt  38280
ttttgagatg gagtcttgct tttgttgtga tctcggctca ctgcaacctc cgcctccctg  38340
tttcgagtga ttttgctgcg tcagcctccc cagtagctgg gattacaggc gcctgccacc  38400
atgcctggct gatttttgta tttttagtag agacagggtt tcgccatgtt ggccatcctg  38460
accttaggtg atctacccac ctcagcttct cgaagtgctg ggattatagg cgtgagccac  38520
tgcgcctggc ccagttccat ttttttcttg atagaagtct tcattagatt tttttttttt  38580
aggtttttat gatttttgtt accatcgtga atggcaaatt tttataaaaa tactttttgt  38640
tactggtagc tacaaaccaa ttagtataag agacaaattg ctaagaagca agttgctgtt  38700
tgtatcttga ttttgtatct ctcaatcttg ctgaattctt agttgttttt gtttgtttgt  38760
ttgaggtggt gtgtcttact ctgacaccta ggctggagtg cagtggtgtg gtcactgctc  38820
accacagcct tgactgcctg ggttcaagca attctcccac ctcagcttcc caagtagctg  38880
ggaccacagg tgcatgtcac cacacccaac caattttaaa attatttgta gagatgaggt  38940
cttgctatgt tgcccaggct gctctcgaac tcctgggatt aagcgatcct cttgccttgg  39000
cttcccagag tgctgagatt acaggcatga gccattgcac ctggcctaaa ctcttacttc  39060
taatgataga ttctcttgga tacctcatgc agataatcat ataagtagtg aataaagatg  39120
gtttttgttg ctttctaagc ctatgtcttt atatttttct tctgttattg acctatgtag  39180
gaccacttta ctaaaattgc agcttttcct gggccttggc tttatgtgtg tgttaatgta  39240
tggagtagaa aggggtatct cagaactgaa gtctcccact aagggccaaa agtctcattt  39300
ctagtcccta catatgagtc aaaggataaa tataggttaa gactagcaac ccattgtagg  39360
gaagaaacat tgccaacttg tagcctaata tatatatttt taatatgtta ctgtttttttc  39420
catgttactg gcacacactt aaagatttct gtttcatggt ggctaaagga ttaatttaaa  39480
ataatttttt ttttcctttt tgagttgagt ttcactctgt tgcccaggct gaagtggagt  39540
ggggtgatct cagctcactg caacctctgt ctcccggttt caagcgattc ttctgcctca  39600
gcctcctgag tagttgggac tacaggtgtg tgccaccata cccagctaat ttgttttttt  39660
ttaaattttt agtagagacg gggtttcacc atgtaggaca gggtgatctc gaactcctga  39720
cctcaggtga tctgcctgtc ttggcctccc aaagtgctag gattacagac gtgagtcacc  39780
acacccagcc taaaagaatt attttgatat atcctttctg catgaaattt ctgtgggaag  39840
gcttttcagg tgatctgatc tgatacagtg ttaggactgg aagtatagct tatactatat  39900
aaatttcctt aattgaaatt tcacattatt taggaactct gtaccctgaa gctgtctcac  39960
tctggtattt aatgtcctac aattagttta agagagcaag cttgggtaag tttcttaaaa  40020
cttccttata tttgtttctt catcaatatt agtagtatag tatcatctcc tatcttatag  40080
attattataa gaaataagtt aataatgtaa agcatttaga acagtattag ttattggtct  40140
caacctcctt ttagctgtta tctacagcct ttctggtaga ttttacttat tctgggaaga  40200
tagtggtgta ttcctcataa tctccttgta cattccaggt cctacaataa ttctcaaaca  40260
ttttagcatc cttacataga ctctccaata tcctggtctt atttccctga tctcctcaaa  40320
tctactgatt tttctcttcc tcagacaagt gatttttcac ttatttggta aaatcctaat  40380
tctggattaa ctcggttatc agattctttc attcctatac cacctgaatg ctgcagtaaa  40440
aagttacctc aaaggacatt taaaaaaaat tataaattca tgattgttga tcacagaccc  40500
taatactgca tgggaatcca ctgcattatc cttgtcagct agtttcctca tctttaccat  40560
gactgtttca atcatctgtt ctcctcagac ctccaacatg ccctttctct ttctacagaa  40620
```

-continued aacttttcct gttactttcc agtgaaaacc ggagtacttg gtgcaaccct tagttgccca 40680
ctatcttttc tatattttct ttcttcttaa tgttaaaata gaggtagtct tgctttctat 40740
ctaaggcttt ctccctttct ctgcagtacc ttatgctgtt gatgatttcc cttttttttg 40800
tatgtttaac ttttctttac acttgattct tctcgtcagt atttaaacac gcttaattcc 40860
tgctattaaa aaaataaaaa caataagcat taatgggtac cacattactg acctttctgt 40920
tctctttcct agccaaatgc tagaaattat tgtttccatt tctcaccttt gactcacctg 40980
tttagtttat tcattccact gtaatagtat ttgcttatga taccaacaac ctctctgtta 41040
gtaaattaag tgaatatttt taaacttggt cttatttgat ctctcacttg gtgtgctagg 41100
gcttctataa aataccacag actgggtggc ttaaacaaca gaaattaatt ttctcactat 41160
gtggaggctg gatgtcaaag atcaaggtgt tggcaggttt gttttcttct gaggcctctc 41220
tccttggctt gcagagggtg ccttcttgct gtgtcctcac ttggtttttc ctctgtttgc 41280
atgcatttct ggtgtctgtg tccagattgg attagggcct ggaagatgaa tttactcacc 41340
tctctaaagg ccctatatcc aaatacagtc gtgttctgac gtactggggg ttagggcttc 41400
aacacgtgaa ttttgggggga gacagtttgg cacataatct cctagcaggt ttaaacagtt 41460
ttgaaaaact atccttggct ggacgcattg gcttacacct gtaatcccaa cactttggga 41520
ggccgaggcg ggtggatcac ctgaggtcag gagttcgaga ccagcctgac caacatggtg 41580
aaaccctgtc tctgctaaag atacaaaaat aagccaggtt tggtggcaca tgtctgtaat 41640
cgcagctact cgggaggctg aggcacgaga atcgcttgaa cctgggaggc agagtttgca 41700
gtgagccaag attgcgccac tgcactccag cctgggcaac aaagcgagag tctgtctctg 41760
gaaaaaaaaa caaaaaacaa aaaaactatc ctttaaactc tttggttttc attttgcctc 41820
tctgatctat tgctcttcag ccttttttta acaggcttct cttctgcttg gttattaaaa 41880
gtagaaattt cttgagtctt ggtcctttgg tattttctgc ttctcttact tctgttattt 41940
ctccccaggc agtcttacca ctttgatttc catttatgaa ggaactgcat acctgttgtt 42000
ccagcactta atttgcctga gtttcagacc tatttaataa tgccatttag cttatcctag 42060
aggtacctta aaaaaacgag ttcaaatctg aactcataat aatccccatc catgtgattt 42120
gaccctaatc tacctcctta gccttactat tctttgttac tctttgccat agctgcacta 42180
tagcaaagca cggcctcttg gtccaggcgt aatatacctt ttcctccaga gtctttgctc 42240
ttatttccta tgttaatatg ctcctcattt ttcatttaca acattaccca gttttcaata 42300
catacaaaag ataaaaacat tagttattag ggaaatgcag acttaaacca taaaataatc 42360
actaaaacca actagaaggg gtaaaattaa aaagactgtc aactacaaat attctaggaa 42420
gccatccaga acactcgtaa attgctggtg tgagtataaa atgggagagc cactttggaa 42480
taccactggc aatttcttat aaatttaagc atacaccttt ggatccagca attctacttc 42540
taggtgtttt cggaaaagga atgaaaacat gtccacaaaa aacttttaaa aattatattt 42600
acagtcgatt tactccttac agctgacaac tagaagcagc ccaaatgtca ataggattaa 42660
tgactaaaaa ttttttggta tattcataca atggaatgcc actcagtaat aaaagaacta 42720
cagaatggca aatgtacaca acatgacatg gatgaatctg acatacttgg caaaggaagc 42780
tggacatgat actgtattat tccatttata ttaagttcta gaagaggcaa agctactctg 42840
gagtgaaaaa ataaaaacag aacaaaggtt gccttttgct tctggaaaat ggtgatattc 42900
aactgggagg gtgcataagg ggccttcttg aagtgatgaa aatgttccat atctcataga 42960

-continued

```
ggtgtgtgtt acatgggctt atctattaaa gttgtacagc taagaagtat gtatttcaat  43020
ggcatacatg tatcttagat aaaataaaca agttttatct aaaaattata gaaataattg  43080
agttaggtga cagggagtgg gaggtgtaga tgaaagaaga attgcagaac gttggtggtt  43140
gctgaagttg agtaatggat gtggggaagt ttagtatact attttgtttg ttttttgtgt  43200
gttcaaagtt ttccatataa agatcttttt aaatcaaagt tacgaagaca cttaaacagc  43260
acctgtggtc tgactgccag cttaataaag aatgcttact aatgtaattt tcttctctgt  43320
gaatcgtacc ctgattcagc actcctttct ccccaccagc cactatcctg aattcctctt  43380
gactttttaa gacatcttcc aaatatcatt ctaaacgtca cgtccatggg ggaaagcctt  43440
ttctgattca gaacactcac tagttttaag tgcccctgtt aagtcctttc atagctttta  43500
tcttaattat gatttatttg cttaactatt atcaacctct acactagact aagcctaagt  43560
ttttggaggg aaagatatat ctattcttgc tgttttaatg tctagaataa taatacattt  43620
attgaatgat tatgttggtg tagtttttta aaaaaattga aggataccca aattgaagag  43680
ctattctatt actgcttatg ttgtaaggtc agtatgttat aaaatgtatg aatgtgagag  43740
aatgactgag aaatgataat ggtttctttc tgattttatt ggcatctgat aaaaacaagg  43800
ggcaataaaa ctgtgttatt agatctggaa ctatatccgg aaagtcctgt cagttggttc  43860
tcaaatgccc ttgagcttta ttatgcttct tccttattaa tgtattaagc cgtgtgagtg  43920
aaagacccct ttcctcttta caaagaatat tctaaatcac ctcttttttc tctcttctct  43980
aatgtgcttc ttcctttgac tattagtttt ggtatttatc agggacagcg atctttaaga  44040
gcttgttgtt ttgttatttt ttgtactgct tgctgtatgt tttaaatttt gatatatctt  44100
actgccaaat gaaggtgtga gctcataagt aataaagata gaaaaaatct gctttgctta  44160
taattatacc attaaacatg ttgtccttaa tgcagataca cactattggt attgtaggtg  44220
caggattatg ttttgatttt tgccagttca tatttccatg gagtatttag gcaattttaa  44280
caacatagat ttctgtaatg aatgtttttt taacttatgc tgctgcttga gagacagagt  44340
cagactgcca gggtttgagt cctatgccca atatttccta gctctgtgac ttttgagtta  44400
tctgcttttt gcctgtttct tcctcattaa aacagagata ctaagtgtac cttatagtgt  44460
tgttgggagg gctatttgag gtagtatatg taatgcctgg tacttattaa atgttagatc  44520
tttttactt tcttgggttc tagggagtcc aataagtaac aaatttttcc tctaaggttt  44580
ttttctttat tggtggcaaa atatacatag tataaaattt acatttcaac catttttaaa  44640
tatacaattc agtggcatca agtacattca caatattttg caaccatcca tctctgtcca  44700
tttccagaag tttttcatca tcgcaaataa aaacttgata cccattaaac aataactccc  44760
atctttcctc ccctgatttc ctggtaacgt atgttatact ctgtctttat gattatgact  44820
attctaggta cctcataaat agaatcatac agtgtttgtc ttattgtcct ctcatttcat  44880
ttggcataat attttcaaag ttaattcatg ttgtagcgac ttctagttcc attttttgtg  44940
gttgaagaaa gtacttccct aatagaaatg aaaacatgtt tgcaaggctt tttttaaaga  45000
atgcttatgg atttagtcat aataggtaac aactgaaaac attggtatgg ctgggtcaag  45060
ttggactaat tcactgtagc ccagggtcat gtaagaacat ggagttttca aggtaggcat  45120
gggggtggta ttgaggggag ggtagtaagc ataaaagaca gtgctcagaa gaagataagg  45180
gtgccaggtt tcagttccag ggatgttcac agtaaggatt acagtgggct aaattttaag  45240
attaatttta taaattctaa acacatcctg ttgactttaa ctgcaactct taaaatgtat  45300
caataacatg actttataat tcctggaaac tgatattttc ccaatacttt gaagaggttt  45360
```

aaaaatagtt gactaatatt agaaccaata tttcatgtat tgatttttct ctttaagtga 45420
cagttagttt agaaaatgct aaacttaagt tagcagtata gagtaggtat atagttatac 45480
tgagtatgaa tgtcttggta ggcttggaag cctaccattt atgtcctctt gaggtacctg 45540
aattaccaaa agctttatgt attctgaagt tattgaaaat aagagctttt gggaattcag 45600
gtagttcagg agtgactttt ctaaaaaaca gaactgagca ccatacacta cttcttatag 45660
ccttttaatt actgccaatt gcctagaata aagttcaaat tcgagggcaa cacaaacatg 45720
gccctttgtg aactgacaga catttcctaa taattcctta catacatgat acccttgagc 45780
cttacagaat taagaatttc tgaatttacc ttggtgtttg atgcatctgt gtttctatac 45840
gtgctgttta tttacctaaa atagactatt ctctatttag cctcaaaagt ctcatggaag 45900
gttttaaaaa atcctgtcta agctctgtta attatattct ttatactatt atatttagta 45960
gttaatatta taaactacct tacagtaatt tttacagata cctggcttac tccctaaatt 46020
gagttgcttg agggcaggaa ttgtgtatta atctttgctg tattttcttt gccttgctta 46080
ctgtagttga ttggtgctaa ttgaataaat gaacatttat gcttttcttt ttgagaatat 46140
tatatgggta gttcctttag ttgtttaata gaagatagca cagacttcta tacagattgg 46200
tttttatggg aaaacacaag agaataatta attaaaacat aatttcatct agaaatttct 46260
gcagttggag cgaatatttt ttaagttatt aacttaccta gagtggaaga ttgaattttt 46320
gaatgatagt gttttagtta ttaaagtaaa tggcatgtaa gagaactttt aagttcatgt 46380
ggcaaaacag ggaaaaattg caaagttaga gtctgtaagg tttctgatgt ttcatagact 46440
aacaaaaggt tgctttatta gcagcattaa tgaacgaatc gctttattgg cctaggcata 46500
ctggtagcat tgtcgttcca aagagctgag agttcttatt tcaattcatg attatgttag 46560
acaagtgaag tgaaagccgt tgaccttctc ttaaggagaa aatagaaagt ttttacaaat 46620
agattataga ttaaagcctt ttaaggaaca tgatgaagaa ctaaattact gctaaatcac 46680
ttgaaaaatt tatatttttt tatgcaccag tcttataaca gtaggttttt tatagaccta 46740
ttaattgata tttaaaataa taactttaat aggatgattt tgtagagtta gtcaaagtga 46800
ttgacaaaag caaattatta aaatagtcaa actttcaatt ctccaaagaa tgttcagttt 46860
taaaagcaat atgagataca ggaagtatta aactggagat gtaatgccac ttggatggca 46920
tacttttaac attatttttt atttgtttaa atggaatgca ttttgcttat tagaatcatt 46980
ttggaagtgc caatttgctt ctgttaattt acattaaaga ttaaaatagg aaccactggt 47040
gaccttctaa atcaaagttc ttcaaaacgg ttgttttaaa cagcaagaat tacagaacta 47100
agtattgtat agctattaaa actgaaaatt atgtagcagc agtccatttt aaatttaaca 47160
attttaaatg atacttcaaa atataaaaaa tacaaggaag aatataagat gcttatgtat 47220
ctgtactgcc aaaatttaac aaatgttaac tttttgctat cactgtttca gaacttttta 47280
aaataaatta aaaatataat tgaagattac taatctcatt cttttgcctc tcttctcaga 47340
ggtaattact tttctaaagg tatcctgtaa gttttcaata ctttttacca catatttgta 47400
taaaaagata aacagtactg atttcctttt aaaatgtgaa taataatata ctgttggcat 47460
aactttttaa cttgcttttt tcactcagtg tttatttaca tcaagattta ttcatgttga 47520
tatttgtatg tacttaaagt ttgtttattt tatcctctga attattagtt tggtccatta 47580
tttatgatgt ttagtttgat tacttggtta aggtggtgtg acctgatttc tctattgtaa 47640
aagtatcctt ttccccttga taattaatca ttaatctgtg gggtaatgcc ttgagactga 47700

-continued gtaaacattg tttctcaaca gcctttcacc cagtgttttt aacatccatt attgatttat 47760
gcctgaatta ttggttacat tgatgcttgc aaaatgattt tctacatcta ttattctttc 47820
cacatttatt agctggcatt cttctttctg taaaggagtt tctgtccttt cactaagggc 47880
tcatggtttc ttcattaatt cggtgaacta aaatccatta ttgttatgta gtcatgcact 47940
gcatatacga cattgatccc atgagattat aatggagctg aaaaatttct atcgcatagt 48000
gacgttgtag ctgttataac atgttaggac taacgtcaca accaacatat tacatgtttg 48060
tagtgatgtt agtgtaagtc aaatctactg tgctgccagt ctaaaagtat agcacatata 48120
attgtgtaca gtacataata cttgataata ataataaaca gctatgttaa cggtttatgt 48180
atttactatg ctatactttt tgttgttatt ttgaatgtac ttctacttat taaaaaaaaa 48240
agttaactgc aaaacagcct caggcagttc cttcaggacg tactccagag acattgttat 48300
tataggagat gacagctctg tgcatgttat tgtccctgaa gaccttccag tgagacagta 48360
tgtggaggtg gaagacagtg atactgatga tcctgaccct gtgtagggct agtctaatgt 48420
gtttgtttgt gtcttaggtt ttagcaaaac agttttaaaa gtaaaacagg aattttttaa 48480
aatagaaaag gcttgtaaaa taaagataaa aggaaagaaa atatttttgt gcagctgtac 48540
aatatgttag ttttacgcta aatgttatta caaaagtcag aaaagtttaa aaactaaaaa 48600
gtttatatga gctaaggttt attattgaag aaagaaaatg tttaaaaata gatgtagtgt 48660
ggtttgagtg tatatttaca aagcctacag ccgtgtgcag taacgaccta ggccttcaca 48720
ttcactcttc actcaatcat taactcaccc agagcagctt ccagtcctgt aagctccatt 48780
catagtaagt gccctatata ggcatatgat tttaaaaaat cttttatact gtatttttac 48840
tgtacctttt ctatgtctag atattctcag acgcaccatg ttacagttac caggcagtat 48900
tcagtacagt aatatggtat acaggtttgt agcctaggag caatgggcta taccgtgtag 48960
gcttgtgtaa atacactctg tgatgttagc acagtgaggg aatagcctaa caaacacatt 49020
tctcagaaga tatccctgtg gttatgtgac gcatgactgt gtatcctttg gtgactcaaa 49080
ttgttaaaat ttagccagcg agaactcaat cagtctggtt tctgtttctt tgacatgccc 49140
cctcattttt atagcaccag tttgctttgt ggcacaacaa aacattctct ccttacctta 49200
tggttttctt accccagacc tggacttggc tattttacca aaagttcttg tttctcttag 49260
tggggaatgg tatttggaag ccaacatcat ggatgcatta ctgggtgtca ttgcttctat 49320
tggttctttt cattagacag aataagaaaa tatactttta aaaactagtg atatttgaat 49380
tcctagtgac accaaggttc ttttctttcc ttgtttcata ttcctcttcc ataatgaaga 49440
tccagtttac caataacatc aatatatgtt tattcatttg ctctgtctta tacatgatat 49500
aacattggaa ttactatagc aataccacta ctaataataa tctcaataaa gtttaagatt 49560
tctatgcagt tttttattta tagcgtatag cccagtgaag gtatatagtc agatcgctat 49620
gcttatagtt attttaatta tatttttcac ataggcaatt tgaaactttt tctaatagga 49680
aggttaagcc tatttactta tcttgacata actagtatgt ttaatctaac tgatatgttg 49740
tatttactgt tgttttatgt tatatatgtt tttcttttac tctttttaa aaagttattt 49800 ttactaatac aaaaatcttc ctttctctag atatttagaa tgttggtctt agctcttata 49860
gtttcccagt ctttttggta tttttgttgt cattactatg tttaattttg ttaactagaa 49920
ttcatgtttt cttttcttca tccatttaat tgggctttat acttttttt ttttttttg 49980 agacagagtc tcgctctgtc acccacacta gagtgcagtg gcgcgatctc agctcactgc 50040
agcttctgtc tcccaggttc aagtgattct cctgcctcag cttcccaagt agctgggatt 50100
acaggtgctt gccaccatgg ctggttaatt tttgtatttt tagtagagac agggtttcgc 50160
catgttggcc aggctggtct cgaactcctg acctcaggtg atccacccac cttggcctcc 50220
caaagtgctg ggattacagg catgagctac cgtacccatt ctatatattc ctttgcataa 50280
atgttgtgtt ctgaggaaaa tttgtgtctg agcatttaat aatttaaaaa attaccatgt 50340
gagtggattt attttatatg aataatgtgc cacatgtaag ttgttctgca gttgattttc 50400
ccttttttgtg gagcttttac aatattgtta gtatgtttac ttgtcccttt ttccccttgt 50460
atgtgtagcc aagtaattat aaaaaatggt gcactttgcc atatctgagc ttctcttttt 50520
cccctcaagt agatactgtg catttgaact gcaaaaaggg tcatattctt gctttatcta 50580
taatctcttt taaaggcaaa ggctgatggt tactttttct ttaataagaa tcttgatttt 50640
tcattttgta tatttgatat ttatcatttt aagaaaaaaa aatcctctat acatagttgt 50700
tagaaattta tgtagaatgg atgttggaac ccaatcataa ggctgtaaaa ccataaaata 50760
agtagtaata aattttaaaa aatgaatagg atttgtatga agaaaataac aacacttcat 50820
tctaggatca aacaaatgaa gagagagcta tttttcagaa tgaaaaacca aatagtgttg 50880
catgtagact ctattcaaag ttctagtctg taaaattaat agcaattcta gtcaaaatag 50940
ctgttttatc ttttgagaag ttcgggaagt ttgacaatct gattgtcaaa tatatgttgt 51000
agagtatgtt aatgaaacta tccagtgtaa aatttaaaaa taaagaccag tattgttata 51060
ttgtactgta ttgcttgcta tactgtagtg gtgtagtaat taaaacacca ttctagtgat 51120
acaggaatag ggtccaaata aataaaaact gagaaggaaa ttgtatacac atgcaagtgt 51180
gtgtgtgcac acacacacac aacacagaaa gggttttttt ttgtttttttg tttttgtttt 51240
ttggagacag ggtctcactt tgttgcccag gctggagtgc agtggcatga tcatggctca 51300
ttgcagcctt gacctcccag gctcaagcaa tcttcccacc ttagccttgt gagtagctgg 51360
gactatgtgt gccactgttt ccaactaatt tttgtacttt ttgtagagac tgggtttttc 51420
atgttcccta ggctggtctt ggactcctgg gctcaagtga tccttcacct cagcctccca 51480
aagagctggg attacaggtg ttagccacca cgcccagcct caaaaagctt tttttttttt 51540
tccctataaa gagccatata tctaaaaagg gaaacagatt tgactctatt acaatggaat 51600
tctgtgagag aaaacatttt aacaagatca gactatctag tagaaaaata tttgtaacat 51660
atagcaaagt tttaacaaac ataataaaga ccttctaaaa attaataaaa ttgaaaaaat 51720
gggttatgaa taagtacaaa taattcaaag agtgtacaca aattagtttt catagaaata 51780
tgcataaaga tatatgtaca agtatgttaa ttttagcatt atttataata ccaaataata 51840
atattccaac aaaatagttg gaataatctg aatgttcacc agtagggaaa tggtacatct 51900
gtattttaga atattagcaa gctgattaaa aagaataaga tctttgtgac caggtatggc 51960
aaaatatccc acattattca tgaaactata gaatgatctg tgtagtatga tctcatttac 52020
ttagctcagt aggtctattg tttgtggtaa acttaaaatt attttattta tcttatagga 52080
tagggacttt taagttaacc tattaatatt attaggaact aaaatatatc actgtaagag 52140
aataaagaca aatatagaat aaaaggaact aagaaaaata ttttacatca gattaattgg 52200
aaatattggt atgaatccat gagtaaataa agaaatatct ctccccccac cctgttctgt 52260
ctaccagaaa atataagaag catggacaat ctcagtagca atggttacat gcatcttggt 52320
tgctaaatat ggctccccat tgaaagaatt caagatgtct tagaaaaata gatgatccca 52380
gttcttagga aaacacacag caagccagaa aacaaggaag tggtgaaaaa ctgaggaatt 52440

-continued

```
atgtaaaaaa gaaccaactc aaaggagttc tagtggccac ctccgaaata atgattgcaa  52500
tcacaggcat atcttggaga tgttgtggat tcggttccag accatcacaa taaaacaaat  52560
attacaataa agtgagtcac acacattttt gttttcctag tgcatataag ttatgtttat  52620
acaatattgt agtctgttaa gtgtgtaata acatgtttaa aaaatgtaca tgccttagtt  52680
tagaaatact ttattgctaa aaattgctaa taatgatcaa ctgagttttt agtgagttgt  52740
tctaatcttt ttcctgctgg agggtcttga ctcgatgttg atgactgctc gccagtcagg  52800
gtgatagttg ctgaaggttg gggtggctgt gacaattttt aaaaataaga cagcaatgaa  52860
gtttgttaca tcaattattc tttgatgaaa tatttctctg tagaatgtga tgttgtttaa  52920
tagtgtttta cccacagtag aaattcttca aaattggagg gcagttctct caaaccctgc  52980
tgctgctttg tcaactaagt atgtaatatt gtaaatcctt tgttattatt tcaatgatgt  53040
tcacagcatc ttcaccaaaa gtggattcca tctaaagaaa tcactttctt tgctcttttt  53100
tataagaagc aacacctcag ccattaaaat tttattttga gatttcagca attcaatcat  53160
gttatcaggc tctgcttcta gttctcttgc tatttctatc acatctgcag tgatttcctc  53220
cactgaagtc ttgagctcct cacatccatg agggttggga tcaacttctt ccagagttct  53280
gttaatgctg gtgttttgat ctccactcat gaataatgaa tgtttttgaa ggcgtccaga  53340
ttgatgaatc cttcccagaa ggctttcaat ttactttgcc cacatctatc agaggaattc  53400
ctatctatga cagctatacc tttatgaaat atatttctta aataataaga tttgaaagtc  53460
aaaagggctt ctcaatccat ggcctgctga atggatgtgg tggtagcagg catgaaaaca  53520
acatgagtct tctggtatat ctccatcaga gctcttgggt gaccaggtgc aatgagcaat  53580
gtcagtgagc aatgagtagt attttgaacg gaatctttta ttctgagcta cagtctcaac  53640
agtggactta aaatattcgg caaaccatgt tgttaaatag atgtgctttc atcaaggctc  53700
tgttctgttt gtactgcaca agccagagta gatttagctt atttcttaag ggccctacaa  53760
tttttggaat gataagtgat cattgttcca cttggaagtc accagtagca ttggctccta  53820
acatgctgag tcagcctatc ctttgaagtt tggaagccag gtattgactt atcgtttcta  53880
gctaggaaag tactacatgg cttcttcttc cagtagagag ttatttcatc tcaattgaaa  53940
atctgttgtt tagtgtagcc accttcatca gtgatcttag ttagatcttc tagataactt  54000
gctgtaactt ctccatcagc acttgctgct tcatcttgta cttttatgga gacagcttct  54060
ttccttaaac ctcatgaaat aacctctgct agcttcaaac ttttcttctg aagcttcttc  54120
acctctctca gccttcatag aattgaagag aggactttgc actgaattag gctttggctt  54180
aagggaatat tgtggctggt ttgatcttct gtgcagaaca ccaaaccttt gtccatatta  54240
gcagtaaggc tctttcttgt tcctattatt catgtgttca ctggagtagc acatttaatt  54300
tccttcaaga acttttcttt tcctttttta acttggttaa ctggcacaag aatcctagct  54360
tttggcctat cttggccttc atcattcctt cctcactaag cttaattatt tccaactttt  54420
gatttaaagt gagtaatgtg tgactcttct tttcactcca acacttagag gccattgtgg  54480
ggttattaat tggacaaatt tcaatgttgt tttgtcttag ggaataggga ggtctgagga  54540
gagggagaga gatagggatt ggctggtggt tggagcagtc agaacacatg caacatttat  54600
cagttaagct tgccatcttc tgtgtttgtg atttgtggtg gcccaaagca gttaaaatag  54660
taacatcaaa gatcacagat caccataaca gatacaataa taatgataaa gtttgaaata  54720
ttgtgagaat tactaaaatg tgatactgag acacaaagtg agcacatgct atttgaaaaa  54780
ttgcaccaaa tagacttgcc caatgcaggg ttgcacaaac cattattttg taaaatccac  54840
```

-continued

```
aatatgtttg aagtccaata aaatgaaatg cagtacaagg aggtatacct ataattgtaa  54900
aacctttgat tgaaaaaaat aatccatgag tccagagaga taagaagaaa aggaaggccc  54960
tcctttagag aattgtagta gcagtgttag aactggaaaa ctgtactgta aactccaaag  55020
aaacaatctg tgccaacagc atcaatggat gccaaaacct ttaggtgtaa gagtgctgtg  55080
aacatgatac gtatgcagtg gtgcccaatt attctgtaaa tcttgtacga ctacaaaggg  55140
aaaatgtgcc tttgcaatag atctatagat tgccacttga actaagtggt cacacttata  55200
atgggacagc ctgataccat gttccttttg ttatgatata atgcggaatg atgtaacctt  55260
gggtgtattc ttgcctaatg tttatctaca atccagtcag gtttctagac ttgatcttgt  55320
ttccaagaaa tacaggaagt tgtggagtaa gtcagaatac attctgggaa gcagtcagac  55380
aaatctagga tgtgggacat tctgtaagaa aactggccat gagtcctgac acatcattgt  55440
cttaagaaaa agatatgtgt gtgtgcgaga gactattcta ggacaggcga gaccaaagag  55500
atttaacagg caaatgttat acataaattt tcatttgccc ttggattgct ctctcaaccc  55560
tgaaggctta aaaatagata tctttgagac acttgagaaa acatcaagat actagcttac  55620
cttattttta cttttttttg actagatgtc ttaatggttt tattactttg taagacttgt  55680
tttaaaagat atgtttcact actcagtata gtctatgata aaatcagtaa atataaaata  55740
tttgtcattt gcatctctta ggaggttcgt ctccattgat gaaagctcag cttatgtgta  55800
actgtcttcc aaagtagctt gcttggaagg acattcacta tcatcatatt ctgctttatt  55860
tcatagctgt gtaatcacat ctactacatc cttgtttatc gtttattaga ttactgcttt  55920
taagcctatt ttagttcttt aatctgagaa taacagttga ctcagttaat ttcattaaag  55980
caagattgcc tgtaattttt ttataacctt agaaaagtac tatgcccaac agcaaaacaa  56040
aaacctaatt caaaaatggg taaaggactt gaacagatat ttctccaaag aagatataaa  56100
atggccaata aacacatatg aagagtctca acaccagtag tcattagaga aatgcaaatc  56160
aaaaccacat ttagatacaa tttggctatt agcaaagaca cagaaaatag caaggattgg  56220
gaaggatgtg gagaaaattg gaaccatgcc tgcactactg gtgggaacgt aaaatggtac  56280
agctgctatg aaagacagtt taccagttct tcaaaaagtt tgatgtagaa tgattgtatc  56340
atccaacaat ttcactgtta ggcttatctc caaaagaatt gaaagaaggg acacaaactg  56400
gataacttat acagcagtgt tcatagcagc attactcata ctaaataaaa gatgaaaaag  56460
gccaaatgtc tgtgaacaga tgaatggaca aatgtgttta tacatatagt agaatattat  56520
tcagccataa atacaaatga aattttggta catggtacaa catagataaa ccttgaaaac  56580
attgtgctaa gtgaaataag ctagacagaa aatattgtat gattctactt agatgagata  56640
ccccaagctg gcaaatatat aaagctggca agtataatag aagttactaa ggcctagggt  56700
gagggaggaa tgagaagttt gcttaatgag tatagagttt ctatttggaa tgatgaaaag  56760
ttctggaaat gaatagtggt gataattgta caacattctg aatgtactca atgctactga  56820
attgtccatt taaaaatggc taaaatagta cattttatgt atattttatg atacaaaaat  56880
atttttaaag taaaagtttg tattttgatg ttacttgtga aaaatatttt cactaataaa  56940
attttgttgt ttcattgctg cctctttgaa aatgtattaa aaattatatg cattttgaaa  57000
tattacagct atataaatga aaaagagtat cagtaaagaa ttttagctca atactctcat  57060
atcatgttat ttattgtcct ttctgtttca cattaagata tacagagtca acaatttaaa  57120
tttgcagatt aaaaaacact ttctgctttt ggccctatag aaataaacca aactggaaaa  57180
```

-continued

```
ggtgtcatgt ttcctagatt gtggacacag aaaaagaaga gctcaaaagg acaagtaact  57240
cagcacagta gatggttatt gacctgatca tatttaagaa tatcctaaaa atgcaaaaat  57300
gttaagaagc aaaactggga aatactggga tgatatatga aaaattcaaa tgacaaatat  57360
gcagtggttg agtatttatg ggtttttttg gggtttacta ttttttcccc caaatttaat  57420
gtctcctctt ttaaatactt ctaccggatt ctctttagat gatgctgcaa ttggattgag  57480
acattttcat tgtttggctt tgtaagattt ccaaatgcgt atagttgtta aaatacgtat  57540
tcaatgaggg tggaaggaaa cacacaaaaa tagaagtatg tcactctggt aagagatgat  57600
aggtccgatg actgctaata cttttccaaa tggccttatt tggatccttc ttagaacttt  57660
tatatttttc taatattgac ctacccottt ggaactagag tcccattgtc aagaactgtg  57720
aagaatcttg acattttacc ctacttgcaa gctagcagtt actcagttgt agttttatgg  57780
atggtggtta aagatatgag actcctgagt tggagttgaa ggacagttta ttagtgcagc  57840
aagcagtagc agtgaccaga gtattagctt cctttttttt tttttgccgc ttttccaagc  57900
cctggttccc atatagtagt gtgaagagga gggctacatg atgcttgtac acactgtgga  57960
ttgcataaca gatgcggaat cctcagcttc ttacagaatc tgaatagtag tgtataatag  58020
gaagtaagaa tgcctttctt tgctttggag caagatactg tctttgtctc ccaacactat  58080
tgctgtaaaa gtatcctcaa aaggatagtg cagaccaaaa gggtagttga gtgtcttgct  58140
cctaagaggt gcagaaacat gagagtctca tagaaaattg tctcccaata atattttctg  58200
ctcatttcta tactattttg tcttaaggca aatttttttc atgagtatac cactctgatt  58260
tatctgacag aagatagtga agtatctgtt caaatagtta gctggctttt aaaatcaggt  58320
tatttgcttt cttattgttg agtttgagag ttctttcttg attctgggta cagtcctttg  58380
tcagatgtgt gatttgcaag tattttctct gagtctgtga cctgtctttt catattcttc  58440
aatctctttt acagaacaga agtttctaat tttgattact atcaggtttt tctcttatga  58500
attgtcttag gaactttttg cctagttgaa aatcacagag ttttttttctt tgttttgtcc  58560
agatgtttta ttattttgtg tcttacattt agatctgtga tctgtcttgc attacctttt  58620
gtttgcataa gttatgaggt agagttcagg ttcattgttt ttgcgtatgg atatttactt  58680
gttctagcac tatttgttga agagactatc ttttccttcg gtgaactgcc tttttacctt  58740
tgtcaaaaat caattgccct tatttgtaag tatattttgc tggatttatt attctgtttt  58800
gttgatttct gtgtgtgtcc tcttgctaat acatcattgc cttaaatagt aacagtttta  58860
tggtagttat tgaaattagt gttctcaaat tttgttcttt tgctgaattg ttttggatat  58920
tatagtacct ttgcattttc tttataaatt aggaatcagc ttgttgatag ctacaaagat  58980
actttgagat tttgattggt gttatgttta atgtacatgt cagtctgagg agactgacat  59040
tttgccaata ttgagccttc caatccatga atatagttat ttttccattt tttaggtctt  59100
tgattatttt catcagtgct ttatagtttt cagcatgcag atcctgcaca tattttgtgg  59160
aagtgtatct tttccagatg ctattgtgag tgctactgct ttaaaaattt ttgatgtact  59220
aacttattgc tgatatataa aaatatggtc gatttttaca tattgatttt atattccaca  59280
acttgttaaa atcataatca taaaaccctt tggattttct atatagacaa catgcttttg  59340
aataaaggct gttttacaaa atttcatttt aaatttgtat acctttttatt tcatttcctt  59400
tcttaattgc acttgctaga gctttccagg acaatgctga atagaggtgg taaaaacaca  59460
tctttgcttt gttcctggtg ttttattact cttttattat tagtgttatg tttagagatg  59520
gggtcttgct cagttgcgaa ggctggagtg caccggtatg atcaaagctc actgcagctt  59580
```

caaactgttg ggcccaagtg gtcttcctgc cccgccttcc tgagtagctg ggattacagg 59640
catgtgccat catgcctggc taagtttttt attttttgtg gagatgaggt cttgctgtgt 59700
tcacaggctg gtcttgaact ccagtctcaa gtgatcctcc cacttgtact gggattacag 59760
gcattagcca ccacacttgg cctcttatta tcattattat tattaatata tataaataaa 59820
tatacatata tttatttatt gagacagagt cttgctctgt cagccaggat ggagtgcagt 59880
gccacaatct ctgctcactc aacctctgct tcctgggttc aagtgattct cccacttcag 59940
cctcctgagt agctgggatt actggcgttt gctaccatgc cgggcgtggt ggctcacgcc 60000
tgtaatacca gcactttggg aggccaagac gggcggatca tgaggtcggg agatcgagac 60060
catcctggct aacatggtga aaccccgtct ctactgaaaa tacaaaaatt agctgggagt 60120
ggtggcgtgc gcctgtagtc ccagctactt gagaggctga ggcaggagaa tcacttgaac 60180
ctgggaggtg gaggttgcag tgagccaaga ttatactatt gcactccagc ctggcaacag 60240
tgagactcca tcttaaaaaa atgttatggg atgaaatttt aaaaagacct ttgaaagata 60300
caagataata ggattcaatt ctgtataagg tagagataaa ctgttgattt gtactagttt 60360
gatttgtgaa atattacaat taggctaaat caaataggtg atgggtaatt tgagaattga 60420
tttctaatgc tttgtcctag atcattcaaa atctgatgtt cacataacta cttagaactc 60480
ttgactagtt gtctgtgctt tttaaaaacc tttacctggc tggctacaac ttttctaccg 60540
ccataattaa aattgaaaac aaaataatta gtctcttagg aaaataattt acgaacacta 60600
tctaaacatg ctagatttaa aactaccagt atttacatgg ttagaattca tgagcagtct 60660
tcattagact tactgctgaa tgaccagcat acagtcgctg aattcattgt gcatctttta 60720
agggaagatt gttttgcttg tatctttgca gtcttctctg agatctttaa tgttactaga 60780
agttataaag tttggttaat tttcctaata agcctttatc tgattctgtg ggctatttag 60840
gtttgggatg ggatctgttg tcttaatttg gtcaccattg gctcttggct tcaaagtgga 60900
ccctaaacta tattcctagt ctgtctagta tttgtctttt ttttgctgag atatgtgacc 60960
cctggggagg tttcccttat tttcaataag ttaatctttc tcttttagga agaaaagaca 61020
aatttctcat aagggaggga ttttttcctt ttttgttcta gagtgccttt caaattaaca 61080
attttgttca tatcaaaagt tgcccataat gatcactgta agtctcaagt tattcttggt 61140
gaaaatatgc catttagaaa gataagtatc tgaattggaa gaagcatgtt tcatgcttgg 61200
agaggttgtg gagttagact gacttaaaaa gtcagttttg tgcagcctgg gcaacataac 61260
aagacccagt ttctatggaa aataaaaaaa aaattaggca ggcgtggtgg tgcacacctg 61320
tagtcctagc tactccagaa gctgaggtgg attgcttgag cccaggagtt tgaggctgtg 61380
gtgagctatg gtaatgccac tgcacttcag cctgggcaaa agagtaagac ctcatctttt 61440
aaaatatata tacaggtttt tcttcaaaag attccaaagg tactgcttta aaaaatgtaa 61500
gattttctaa gcaacagggc cgagtacttt gctttaaagt ttttatgaat gcctggcttg 61560
gctatctggt tgcttttgaa atcaacatct tactaaacta ttaatgcttt taaaatgtgt 61620
gcagaattac atatttgtaa atttaacttg agtctgtcta ggaaagcatt agcaagactt 61680
ttgtttttgt ttttgttttt ggagacagtc ttgctctgtc gcccagcctg gagtgcagtg 61740
caggtcactg ctcactgtag ccttcacctc ctgggctcat gctatcttcc cacctcagcc 61800
tcctgagtag ctgggactac aggtgtacat caccacaccc agctaagtaa aaagatgtat 61860
ttttcataga gacggggtct ccctatgttg ccaggctggg cattagcaag attttacggg 61920

-continued

```
aaattttttt tatcattagt agaaaataat aaggaatccc ttgctggtaa aatttatatt  61980
gaaactactc ttaaacatat ttatataaaa tgaccagaga tatttaattt acctttatat  62040
aataaataga aataaattga aatacattat taggagattc agattttttta attagtaaat  62100
tagtgtgatg gcttaaagtt attgagaggt aatttttcat ctttgattag aaaaacttaa  62160
aaattgtata atttacatac acaaagtata tatgagcttt ttatattgat gaactttaca  62220
aaatgaacac acttttgtaa ccacaaccca gatcaagata tcagcttctc aggagcttcc  62280
ctgtatctgt catattcctt tacatgaaag gtaattaata ttctgacttt gtaattagag  62340
attagcttgg cttttttttg aatttttata aatcataaag tatataagac tatatgattt  62400
ataagttttt tcaaactggc ttctttccca cagcagtatg tttttgagat ggatatttgg  62460
cttacagcat ttttcatttt cactgaggct tagggtttca ttgtgtgaat atccttagtt  62520
tatttctccc ttctgctgat ggacattcaa attatatcaa ttttgggttc ttacaaatag  62580
tgctgctgtg ataattctcg tacatatttt tttgtgcata tatgtacaca tttccattga  62640
gtgtatgctc aggggtagta tcacttagtc tttgggttta tcttcagctt agtagacact  62700
tccgaacagt ttcccatact gtttgtatta tattattata catttttacc tgcagtattt  62760
tagaatgtca gttgctacag atttttgctt acacttggta ttgtcttttt ttagataaaa  62820
gttagtcatt ttggagggta gtagtatgtc tttgtgaagt tttgtttggt ctttagccta  62880
tcttaaaaat cggtttgttt tttttgttga gttgaagtat ttttaaagaa tatattttgg  62940
gtatgagtct ttagtggaac atgtgcattg ctgatatttt ctcctacact gtagcttgca  63000
ttttcatttt taatttattt aaattttatt ttatttttta agagacaggg tctcactctg  63060
tcacccaggc tggagtgcag tggccttatc atagcttatt gcggccttga actcttgggc  63120
tcaagcagtc ctcctgcttc agccttctga gtagctggga ctgcaggtat gtgccaccac  63180
acctgggtaa tttttaaatt tttttgtaga gacagaatct cactatgttg cccacactaa  63240
tctcggactc ctggcctcaa gcagtcctcc tgcctgggtc tcccaaaatg ctgggattac  63300
aggtgtgagc cactgcgcca gtcatttcct tctttccttc tttctctctt tccctctttc  63360
cctctctctt tctctcttcc tttctctctc cttccttcct tccatccttc cctccctccc  63420
tccctcccca ttcccttccc cttccctccc cctttccctc cctgcttccc tccttccttc  63480
cctccttcct tctctctttc cttccctcct tccttccctt tttccttcct tccttccctc  63540
cttccctcct tccttctctc cttccttccc tccttccttc cctccctgta attgtaatga  63600
aattgtttgt ttgtaatgaa attcagtttt tttatgtgct gtgtattaaa tctatgccta  63660
aatatcgtga cagtatttat cttgtcacta tataagcttt attatttaaa attttatata  63720
tataggtctc taatatatct tatttttttt cccacctttt ctgtggcttg tggatagatg  63780
ttattcattt tactgatttt gattttaaca gtagtagtca tagaaaatct attgatgtgg  63840
cttactcatg agaaagcatt tttattttta tatgtgatat tataatttct agtatggcaa  63900
cattttctgc tagttatgat atgtgatttt tactctgcag attctttaag aggaatttaa  63960
aaacagcttt attcctgact ttagagaagg cagtcagttt tacttaatat gtcattttat  64020
gtcttatttg ttatgttttg tttttgagga gtcatactgg tagtttaaaa atactgagtt  64080
ttatcatcaa atgcagctac aatgtttaag cagatgactt aatctccgtg aggcatgagg  64140
tgattaaaaa atgtatgtat atgctttttc aaatacagag taaattgcct ggcagacaag  64200
aagagcttca taaatattat ttagtgcttt ttattctaga tttttgaaat aaattggact  64260
cgacttgatg caaaggattt gtactataag tttattataa aattattaac cgctagcttt  64320
```

tgtaaatagt aaaattgatt tgcccattat acatttcttt ttgttatgca taaaatattt 64380
taatttttaa gtaccaacat aggatggatt tttaaatgct tcctcatgtt aatttttttaa 64440
taaacataga atgaatactg tgtgaaatat tttcccactt tattggctct gttttaactc 64500
agtagactct atagttagat tgtctaggtg ccacttaaaa gatggtaact agataccaga 64560
atgtgttaca ttatatgttg attgtcagga agaactgaat gcatgaatgc ttccctaaga 64620
cattgttagc atgccgtggt cttgatctat aattttttgt ctaagttgtg atagagctca 64680
ttctttacat ggtctagtaa attcagccaa tgtctttata attcattagc atctctatat 64740
attacctata aaatttaaat tataaggcta tgaaaaaatt gtttcatatg tataatatac 64800
caaagtttta gcatatggtt tggattttaa actgttttac tgaaacaaat taccgtcatt 64860
aaatggaatt cttaggtaga cattacagag taggtgtaac tctgaagttg aaaatggttt 64920
catcttcttt tttaaaaaat tttattatat agggaatctc aaccaccagc aggattttaa 64980
aaaggctatc taaatatttg gtaagtaaat attctccatg ttaaatattt tgcgtgttac 65040
ttaagtttac acatatgcta catgaatgac atttacaata gtgagtgtaa attatagtta 65100
taattaatat tttaaatttt acttggttac tagaattttt gtctccttaa acctattcca 65160
atccttttct ctcttgttct ttatgttgtg tccagagatt ctttcagtgt acagccttat 65220
tattaagagt tcaaggaaag aaatggtttt agtgagcagg aatgctaata ctttatgaat 65280
aaaacaggat ttcccctact tgagattttg tagtatttct tttttgtgaa aacactaata 65340
cagatttgtt ctttagccat ccattgcttg actcctcctt gtatttaggt cctgtttgct 65400
gcaacatgcc aacatgaacc aaatactgtg gtcagggtct atgcatttcc tgtttagatt 65460
attctttgtt ccaagcttaa aatatgaaaa attttgtagg tgtctgtagt taagaatttc 65520
ataaacttat gatttcatag ataaagcttt tactttttta tttttgagta aaggtaggtg 65580
agtcaatctc agaatgtatt ttacttcaac tacatagtat tttatacctg tgtactatgg 65640
tgattatata gatataaaat gatttggtta atcataatag attttaaagt tattaaatat 65700
gcttcagaat gggaaagaag tgctgagaca ttgcataatg aggtgtcata gtataggctt 65760
ttggttgttt ttaatatagt caatagcaga ttattaagga ggaaatattt agtgataagc 65820
attggcttct tttattatac tttttaatgt gtttgaaaca gcaaatattt gaccaaatta 65880
tttttcttaa attttatagt aactacagta ggtgcctaaa tgttcaacag ttatactgtt 65940
ctgtttactg taaatttgta ataaatataa atacttttag gagcaaatga tgccacagag 66000
atctcttaaa cagattttta ctactttaga aggtggtaac tgatttctgg agttgtatta 66060
agtacaaaag agtaacttat tgtcattttt ttccctattg atgcgtatat ttgagttaga 66120
gggaagcagt cgtctttgtg ttatatgctt atcatgtata tttcatctta gcaaatttat 66180
taattttagt gacagtttta ttgagatgaa atttatatac caggagattt catctctaag 66240
tgtacaattc agtgatattt taatatattc accaagttat gcaactacca gtactttgta 66300
atcttaggtt actttcatca tccttcttct ggacgccctc tatcacccag ccctaggcaa 66360
ccactaatac actttctgtt tgtataggtt tgcctattct gggcatttta taaaaacaga 66420
atcataaaat atttgtcctt ttgtgtctgg cttctttaat ttagcatgat atttaaagct 66480
tcactcatgt tgtagcatgt atcagtgttt cattcatttt tgtggctgaa tatttctttg 66540
tatatcattt gtgtattcat cagttaatga gttgtatcca cttctttttt tggctattag 66600
gagcgctttt ctgtgaacat tcttatataa gttttgtgta gatacgtttt tgagtatata 66660

-continued

```
tggatggggt gggattgctc gataatatag tacctgtgtg taactctttg aggaactctc  66720
aaaatggctg taccatttta caataccacc aacaatgtat gaggattgta atttctccac  66780
gacctcataa acacttattg tcagtctttt gtatttcagc cattctagta ggtatgaagt  66840
tgtatcccat tgtgattttg atttggataa tgactaatga taagcatcat ttcacatgct  66900
tattgaccat atatcttctt tggagaaata tctgttcaac tcctttgccc attaaaaaaa  66960
aaaagattat ctttttaatg ttgaatattg taaacattct ttatatattc tggaaactag  67020
tcccttatca catacatgat ttgcaaatat tttctcctat ggattatctc tttactttta  67080
tgatggtgtc ctttgaagca gaaaagtttt aattttgaag ttcagctgat ctgtttttttg  67140
ttgcttgttc ttttggtgtt atattgcaga tttgttttta aataaatact cactgatagc  67200
ctgggtctat gacaaagttt taatcgtcat aggactacga aaaagcattg gcatttcttg  67260
tgtttgacag tcaaagccca aaggaggcaa ttatccttgt atttgtgctt cagttcctca  67320
gctaattgtt ttaagcaaaa ccttacgttt tgatcccatg tgttactgtg aaaatattag  67380
ctgtgtgtga tatgtttatt gatattagtc ttgtgaattt atgtttagtt tttttggat  67440
tgaagaaggg aggggccatc cttaatagat gttattagtc cgttctcacg ctgctgataa  67500
agacatatac ccaagactgg gtagtttata aaggaaagag gcttaattga ctcacagttc  67560
ctcagggctg gagaggcctc aggaatctta cagttgtggc agaagaggaa ccaaacacat  67620
ggtgacagca aggagaagtg cagagtgaat cgggggaaaa gccccttata aaaccatcag  67680
atcttgtggg aactcagtca ctattatgag aacagcatgg aggtcatcat ccccatgatt  67740
cgattacctt gcactgggtc ccaccacaac acttggggat tgtgagaact gcaattcaag  67800
atgagatttg ggtttggaca cagccaaacc atatcaatag tttattatga caattactgc  67860
atattttatt tcatagttta agaaaccatt gctttttaga ctaaggatta tcaggttctt  67920
atctttcttg tgaagaagga atagattttg ataatctcac tgattttaat cttgtacaga  67980
ttattattat tattattttg agacggaatc tcgctctttc gctcaggcca gagtgcagtg  68040
gcgcgatctc agctcactgc cagctctgcc tcctgggttc acgccattct cctgcctcag  68100
cctcccgagt agctgggact acaggtgccc gccaccgcgc ctggctaatt ttttgtattt  68160
ttagtagaga tggcatgtca ccatgttagc caggatggtc tcgatctcct gacctcgtga  68220
tccgcccacc tcggcctccc aaagtgctgg gattacaggt gtgagccacc acgcccaacc  68280
cagattattt ttaagcaatg atattttggt gtttttgtaa acttatgtat ggaatatgta  68340
agtttttcct ctattaagta aatgtcttta attttttttt ttttttgaaa tggagtctcg  68400
ctctgttgcc caggctggag ggcagtggca caatcttggc tcactgcaac ctctgcctcc  68460
cgggttcaag tgattctcat gcctgagcct cccgagtagc tgcgattaca ggcatgtgcc  68520
accaaacctg actaattttt gtatttttag aagagacggg gtttcaccat gttggtcagg  68580
ctggtctcaa actcctgacc tcaggtgacc acctgcctct gcctcccaaa gtgctgggat  68640
tacaggcttg agccactgcg cccagccagt gtctttaatt tttaaggtac caatttagtt  68700
ccttattttt tatcgttatg tgacgttatg tgatcagttg aaggtgtatt tcatgtattt  68760
tgacctataa tgttgtctag tttagtttct ggagaaatgg tgtgtaacag tggaatgtca  68820
cttgtcttca aagcattagc tttctgtgta aggttgaggt tgtaatataa atgcgctaga  68880
tgtgttttta ttaggggaat tgactattct tacctttcat gttatttgac agtattcttt  68940
gtcaacttca aataacggcc tattttgatg agattttata gtgctaggat cactgatatt  69000
cttgttagtt gatttaaaat catggtgttc attggctaac agtcacttga gtggctatta  69060
```

gatgggtaat attgttctct tttttttttt tttttttgag aaagagtctc actctgtcgc 69120
ccaggctgga gtgcagtggc atgatcttgg ctcactgcaa cctctgcctc ctgggttcaa 69180
gcgattctcc tgtgtcagcc tcctgagtag ctgggattat aggcgcatgc catcatgccc 69240
ggctaatttt tgtattttta gtagagatgg ggtctcacca tgttggacag gctggtctct 69300
aactcctgac ctcaggtatc cacccacttt ggcctcccaa agtgctggga ttgcaggcat 69360
gagccaccgc gcctggccag atgggtaata ttgttctata cattgatatt cttatggttt 69420
atgttatagt attcatggaa atttagcaat ggaaaaggaa atgaaaaact tattaatgat 69480
gttgttaaat tttcaattgt gatgacagta aggaaaagac ataattgaga gctacctcca 69540
attgtttata tcaaatgtgg taattaagag gattttggtg acctatttat ggctgaatta 69600
aggcaaaata gcttttatat ccgattcttt cctcttccct tctcttgttc tgtgtgctta 69660
ctatcataat aattgagtat acattaattt tctttaagta tttatatttt aaataaggtt 69720
ttgatgtcag tagagacttt tttttttcct tgaaggtaag taccctttaa accactaatt 69780
tgtcactaga gtctatagtc gcttccatat ataataggta gcacagcttc tcaggtcatg 69840
tcctgctttg ctgctctgct gaccaataat acaccttgga gatactggtt ctggttatat 69900
gaatagaaca attaaattgt tcttcattag atggatcttt gattactaat cttactcaga 69960
aaggctcaac tggacttgga ttattctaat tgccaatact gtttttgcac aaatgtctgc 70020
aaatcattga acagtaatac tgaccccttt ttcttccaat aaagttattg cagtaatcac 70080
atcattgcag agaatatttc ttaaaagctt ttttcaatat ttacttcttt aatgaaaaac 70140
ttaatccaga ttaagccaca tacatagacg tcttgacttt attattttga atacctgaga 70200
tttccaaaat ctctttaact gtcttcacac aatttctagt ctgtcatttt aattaattac 70260
aactgttcat ttcttctgct tttgtttcct cttcatgtgc tgcctagcgt tgctagagtt 70320
tcatcagttt cctgccttga gaggtttcta gtacaaatta acattttccc ttcctagttt 70380
atgcaggttc cttcctggta atttttatct ttttgatctg tttcattctg catgttagtt 70440
atttggaacc attctactgt gctcaaatga acagtcctat ccctagttct cttattcctt 70500
tttcatttca tattttatac ccttttttcct cagtctgtct taaagaataa agtgttttca 70560
tttcaaaagc ttattatctc tgtttttaat cttagccctt ctttcctcta ctatttttct 70620
tcctcttaat gctccatgct gggttctctg ccttatcaga cttaatcttg aaaagtacgt 70680
tacttccttc ccattatctc caaggttgtt atagtccatt ctaggtgtct ccaatttctc 70740
aactcttact caattacttt ctgaagtttg actattattt ctactagtgt tcagctttct 70800
taagtgtaag taaacacatt tcttacttaa ctaggtagat aaacattagc tggacggatc 70860
tggccgtaaa catgctatta tttccaagat aaaactgagt tccaaatggc taaatctttg 70920
tcttttcact tttcatccat tcctgtcttt tttagcattt gtttttttgc tgcttaacat 70980
tcacttctcc tttgtcttct gtaataaacc ttaatggttt ttctcctctc tctggctaaa 71040
tgtttgtttt ctttgttact gctttcttct tttatatacc acttatatat aaattgggtt 71100
gaagctttgc tcttagctct ttttcattac acatcatttt gaggagatgg tctcgtgttc 71160
attatgtaga ttatcacaaa tttgatgact cagaaatacc acatttttct tagtgacctg 71220
ttttaccact ttctcagtcg ccaggtcctt agcaccccaa aattgttatt tcccagtgga 71280
aagtttgtct tgtacaatgc ttgctatatg gttggaacta agtaaatgct ttttgaatca 71340
tgaactaact ccttatctgt cttttttttt cttaagataa tggttttaac tgtccaccta 71400

-continued

```
ttctcatgtc acaagccctg taatatctct gaccacttct tgtctacact tgttaatatt  71460
agttgtcata ttttggtcct aagtttgact aatgaggaag atgacatttt tgtctgcaga  71520
tggtggaaat aaaaatcaca gagattgtga tttccttatg gttttgtggg taatggtgga  71580
gtttaaactt acaacgaagt ttctggtgac atgtttccta gttttcacag aaaacattct  71640
ttttttttt gagacagaaa gtctcactgt gtcgcccagg ctggagtgca gtggtgtgat  71700
gtgtcggctc actgcaacct ctgcctcctg gattcaagtg attctcatgc gtcagcctcc  71760
aagtagctgg gattacaggc gcccaccacc acgcccagct aatttttgta tttttagtat  71820
agatggagtt tcaccatgtt gaccaggctg gtcttgaact cctggcctca agtgacccac  71880
ctgtctcagc ctcccaaagt gctgggatta caggcataag ccaccacacc cagccaaaaa  71940
cattctttat aatgatacaa gtaatatacc agacaagaaa ttactcagtg tactatgtga  72000
gattaaaaaa aaaaaaaaaa aaagactgga agtggaagtg ggagtacttc aaattcttgt  72060
ctgatgaggt aaagatttta acttggtgga aggaatagaa atcaaggatg tgagaaattt  72120
ttcattaatt agaatttcga gattcttctt ttaagaatgc agtgatgcta gtgaagtggt  72180
tgagtgaacc atctttcagc taacaattat aagatctgga caaaatattg aaagaaaaac  72240
tttaactgtt ttaaaagcca tggaaagtaa ccaaaaaagc aaagccagat gagagcctcc  72300
aactgcaatg tgtaattgta tgtttgtggc tttcttgcct tatggtgcat tttcgcctcc  72360
tgtctttcag tggcatagga aagaagttac gggtagcctg gcagttggaa atttactcag  72420
gggaatcatg gaagcaataa gtaagatcca aaatctgagt gtaaactctg tccaaatcat  72480
ggctaatcac gaaactatac atgcataggg gagaccccag gggacccagt gtaaaaacag  72540
gcagaaacaa gagcggaatc tgctcctgaa agaattgaac cctgtgagat ttgtgattgc  72600
ttcttttttt gacagtacat ttctcaactt gcatgcaatt tgcgtggcca acagctggct  72660
tgaggtatca gagcacagaa catattgttg acagaagagt taaaatttag ggaacaaaca  72720
ctgaaagcaa gataacatca gaggatgtag gccacacatc tcagtataat ctctgcccat  72780
ttccttcact gaccaccaga ctacccaggt gcagagggga tgccctgggc atcaggttag  72840
aagaaggaag cagctggaag gtgaaagaac taagcaaaat cattgttgct tactataagg  72900
gagacacaca gtaagtcctc acttaacatt attgataggt tcttggaatc tgactttaac  72960
tgaaacaacg tataacagaa cattttttc tcatcagttg tataacaaag cagtgttaaa  73020
ggaaacgaca gtattcaagg accttgctgt ttgtgttttg cttcaagttg ctgtttccaa  73080
gacctatcga tggtattaag tgaggactta ctgaagtttg cagtttgagt ccatacgagc  73140
ccattagaat catacaacat gaaaaccaaa tggtcctttg aaagattgcg acaaaatctg  73200
gttgctataa cttgctattt acaatgtgta ttttcaacta aaaattatta gatatgcaaa  73260
taaagtggaa atatgactca ttttcaggta aagaaaatca ttcaatagaa attaacccca  73320
agtatagcca gatattggat ttagcaagca aggactttaa aatagcccta aatataatca  73380
gaagaattta aggagtccta tgttcaaagg attaaagaaa aatacagtca cccctctgtt  73440
tccatgtttc tgcatttgca gattcaacca accgtggatc aaaaatagtt gggaaaaaac  73500
ataataaaat ttacagtaca gcaataaaaa ataatgccaa taaaaaacaa taaagtcttg  73560
ttcagtgaat agataggaga tcaaaacaga gaaacagata ctgtaaagaa gaagcaaaag  73620
agaattttag ggttgagatc agtaactgga atgaaatttt tatattatat tttattttat  73680
tttattttgt ggtggagtct tgctccgtcg cccaggctgg agtgcagtgg tgcgatctcg  73740
gctcaccaca acctccgcct cctgagtagc tgggattaca gacatgcacc aacatgtctg  73800
```

-continued

```
gctaatttt gtatttttag tagagacagg gtctcaccat gttggccagg ctggtcttga  73860
actccctccc gacctcaggt gatctgccta ccttggcctc ccaaagtact ttgattacag  73920
gcgtgagcca ctgtgctcgg ccaagcaaaa cagttgtttg gagatggcaa aagaatcagt  73980
taaagataga ttaataaaag tcatctattt gaaagagaaa gaatggagaa aaataagcag  74040
agtttgagag acctttgggg taatacaatg tttgaacatg catctaaatg gagtctcaga  74100
tggggaataa ataatggctg aaaacccccca caactttggt ggaaagtatc aatttacata  74160
tccaggaagc tcagcaaact tcaagcagga taaacacaca caaaaaaaca gatgttagca  74220
cataagtggt caaattgctc aataccagag aatttcttga aagtagccag aaatatctta  74280
ccagaaacaa tggcgacctc tagccatgga tatggtatat tcagctgaaa ggcaaaaagc  74340
tatcaaataa gaattctgtg ttcagctaga agtgaaggta aaataaatac atgttcagat  74400
aaaccaaaac tgggaaattt tcaccagcca gccaccattg caagcatttc taaaggaatc  74460
aatttcaagg gaaatggcac cagatggcaa gtaccatcta caggaggaaa tcaacatcaa  74520
aactagtaaa tacataattt actctaattt ttataaacta tatttttcct tattttaaaa  74580
acaagtacct gtgacttgaa gcaaaaatta tgatgctgta ttgttgggtt tataatggag  74640
tttgggaatt tacatattgt acaattttta atatgtaatg acatacaaat taacgtgtta  74700
atagtcttct aacttatgaa catggtatat ctcattaagg ttattgttta attttagtaa  74760
tgtataatag gtttctaaaa aacttaaaaa tgtggtaaaa tatgtacaaa ataaaatttg  74820
ccattttagc tgtacaattt ggtggcacag ttgcattcac agtgttgttc gttcattact  74880
actttttcca gaacttttct atcattccaa acagaaactc tgtacctact aagcagtaat  74940
ttcccatttc ccttccccga gtctctggca gtgtctaatc tactttctgt ctttatgaat  75000
ttggctattc tgtatttcat atatagtagt ccccccttatc cacagttttg ctttccacaa  75060
ttttggttat ctgtggtcat ccatggtctg aaaataggtg attatagcac aataagatgt  75120
tttgagagac cacattcata taactttatt acagtataat tgttcttttt tattattgtt  75180
gttgttaatc ttttactttg cccaatttac agattaaact aataagtata tatgtatagg  75240
aaaagacata gtatatatag agtttggttc tatctgtggt ttcaagcatc cactgggggg  75300
tctggaacat atgctctgtg gataagtggg ggactagtgt acttcctgcc ctacccccttg  75360
gtttggagtc gctgctgtat gaatataagg gcagtctgcc tgtgatgtga ctctccattg  75420
atcacctggg tgtatgaatt aattgctgtc tataaagagt cttggaatga ctattgagtt  75480
tgctctgtgt atgtatacat acaacagtat ggctactgtt gtagctgatt tggctatgat  75540
actgtagtat cttatttgct ccaaagagat ggagtagtga tgaaatctgg tttactaggt  75600
ggaagctagt gtaaaaatgg gtactctgtt ttattgaatt agcttgattg gaaaaagtga  75660
agtgctgatg gttttgaaaa tatgatgata atgatgtcat ccttctggtt taaatatttt  75720
gtagcacttg tggtagattg aatgctggtg tcggtagtaa agtcatgctg cagttatagt  75780
ctgaaccagc tgtactgttt tgggtagtaa cttagacagt agagaacacc actttctag  75840
gcagggctcc tcacctctcc tagggggcca tttcactgca tcttggagtg aatatacaga  75900
gaggaagtag ctagatccta atttctacaa gttatatcag ttggggaaca gttgtggttg  75960
tcaacctgtg ttagggctgt attggttttg ctttcagttg tgctataaag tggaaaaaat  76020
tgaattgttt atttatctct tattgtgaaa ctttcctgtg gcccatagaa gtggcatagc  76080
aagctgaaca tagctgggtt tgttcttcat tgcaagatcc taccccccacc tccctttctt  76140
```

tcctgcctgg tttcttgtgt ccatactgca agctcttttt cccagttaga agtaagttag 76200
ttcactctta atagagctga tttacaaagg aattttatgt gtgtcatact gtttgattct 76260
ctgaaaggta gatatgggac tgtggtaaca atccagcatg atgttaactg tgctctcatt 76320
tttaaatgtg caaatggatg tatgtgaaat ggtggtttgt ctgatacaat attggctgct 76380
aagacatgtc tgacctagag cctagatgtg ttggcttctt aataatgctg gatgatgtat 76440
atctggatca ttctttttaa ttgactgaga tgatgcgtat cttctacctc ttgagagtta 76500
ggaatgtaaa gggcaagtga aaaatttgtt agatgctctt aaaagatgaa aatagatgtg 76560
ctccatcact agtatagttt ctttttgacc actatgtcaa cctgtttaga aagtatattt 76620
taggccgggc gcggtggctc acgcctgtaa tcccagcact ttggggaggc tgaggcgggc 76680
ggatcacgag gtcgggagtt caagaccagc ctggccaaca tggtgaaacc ccatctctac 76740
taaaaataca aaaattagct gcgcgtggtg gtgcgtgcct gtaatcccag ctacttggga 76800
ggctgaggca ggagaatctc ttgaacccgg gaggcagagg ttgcagtgag ctgagactgc 76860
accagtgcac tggcatggca acagagactg ccaacagagc gagactccat ctcaaaaaca 76920
aaacaaaaca aaacaaaaaa caaagaaagt atattgtaaa catcaaatta aaagaatttc 76980
ctgaagtaac tttttttttt tttagtaggg gtggggaaga tatgagtaga agagaaatga 77040
attggaaact gagtaccact acccttttc ttaccttcta tccagaaatc tttcttaaat 77100
tccacagtat cagtgtaaca tcttttatct tttgagctgt ctttgagatt ctttactttg 77160
tctccagact gtttgttagg attctactag agaagttgtt ttcagatttt aatttctctg 77220
ctccatttta atcttctaat tttttaatga aaaaaaatcc agttttattg agttcttttt 77280
tttttttttt tttttttgag acagagtctt gctctgtcac ccaggctgga gtgcagtggc 77340
acgatctcag ctcactgcaa gctccgcctc ctgggttcac gccattctcc tgcctcagcc 77400
tcccaagtag ctgggactac aggcgcctgc caccacgccc agctaatttt ttttgtattt 77460
ttagcagaga tggggtttca ccgtgttagc caggatggtc tcgctctcct gacctcgtga 77520
tccgcctgcc tcggcctccc agagtgctgg gattacaggc gtgagccact gcacccggcc 77580
tattgagttc taattaatgc ataatttgtt gagttttgac gtatatgtgc actcatgaaa 77640
ccatcaccac aatgtatata tccagtgaat atatacatca cccttaaaag cctctttgta 77700
atctcttcac tccccacttc gcaggcaacc actgatttgc tttctgttac tgtaggtcag 77760
tttgtatatt cttgaatgtt atgtaggtag aatcatataa tgtgtctcct cttttgtctg 77820
acttctttca accctagctc aatatatttg agatttgtct atattgttgg atgaatgatc 77880
aaaactttgt ttttgttttt ttaactgggg aatagtattt catttttagt atatagtaca 77940
atttattttt tgcccatttc catttagctg ttattgctgg attgggttat taacagttat 78000
tgactattat gaataaagtg gtcacaaatg ttggtgcatg gttttttatg tggacttgtg 78060
ctcttatttc tgctatgagt ggaatggctg attcatatag taggtgtatg tttacctgta 78120
taagacactg ccaaactttt ccggtttgta tcagtttata ttaccacttg cagtgtatga 78180
gcattccagt tgcttcacat cctcagaatt cttggtatgg acagtatttt aatttgattt 78240
gttttagtag ctgtataata atgtcttatt gtggcattca ttaatcatta ggaaaatgcg 78300
aattatgttg aacatcttta cctatgcttg tttgccattc acatcttttt ctgttgaagt 78360
attttctcga atctttgctt attgatttat tgatttattt attttgagta agagtcttgc 78420
tctgtctcct aggctggagt gcagtggtgt gatcatagct cactgcagcc ttgaactcct 78480
gagttcaagt gatccccctg cctcagcctc ctgagtagct gggactacag atgtgtacta 78540
caacacttgg ctgttttttt tttttttttt tttttttttt aaggattttt ttaaagagat 78600
agggcctgac tgttgcccag gctggtctca aacttctggc ctcaagccat ccttccactt 78660
cagcctccag aagtgcaggg attacaggct tgagccacag tgcctaaatt ttttcattgt 78720
attgtttgtc ttattattga attataagag ttctttctat gtgctaaata ctagtccttt 78780
ggataattac ttgcagattt ttttcagttt gtggtttgcc ttttttttctt tacccatgtc 78840 ttctcaagtt caagtctttt attttgatga atacacattt atagtttttc ttttatattt 78900
catgcttttt gtgttgtatt ttggcaggcc aaataatgac ccctgaaaga tgtccatatc 78960
ctaatttcca aaagctgtat atatgttacc tgatatggct ccacaaactt tgcatatgtg 79020
attaagttaa agattttgaa atgaggagat tagccaggat tgtccaggtg agcccagtgt 79080
aatcagagag tccttgtaag aaggaggcaa aaccaatcag ggcagaagag atgaatgact 79140
gcagcagagg ttggaatgat gtgctttgaa gatgaaggga aggggccatg agctaaggcc 79200
atgagataat aaatttgtgt tgctttacac caagtttata gtaatttctt accacagccc 79260
atatagattt tgcctgtaag tggaatgccg ctgtaacaaa tacctaaaaa ggtgaaagtg 79320
gctttgaaat tggggtattg gcagaagctg gtagaatttt gaggaacata atggagaaaa 79380
cctagattat cttgaatgta cagatggtag aaatacagat gttaaaggct ctgctggtga 79440
tgccccagaa ggaagtgagg agcacagtag agaaaatgtg tatcgtctta gagaatacct 79500
aaatcatcat aaagagactg ttggtggaaa tgtgaacatt aaaggtgctg ctgcttgtga 79560
gtgctttgaa ggaaatgagg aagatgttat tggaaactga agtgaaggag atccttgttt 79620
agattgtaac agaaagttta cctgaattcc gtcctgtagt tatgtgacta actctcctgt 79680
gttgcctggg tatagcagca atcatttata catacatttg cagttctgtt ctgtacttgt 79740
tataaagtag ttttaattaa agtgacagat ttatgttttt ataaattaaa tttatattta 79800
aaaaatcagt atttagaaca aatatcttag tggactatat tcttgagata ttattattaa 79860
agtcttttta cagcttcctt tcaaataaat ggatatgtaa tttaaacctt taatttctgg 79920
atttcctgat gacttttctt taaaaagaat aatttttaaa aacacatttt aatttataac 79980
taaaatggtt atttaaggaa acacatatat tagttttatt tagatatatg ctttttttatt 80040 attaatttgg aaagtggagg tgcattgttt ggtagaataa ttttaaatgg tagctcttgt 80100
taatggctaa tatttattag tggatacaac ttacaaatat ctgtacattc agtctttatc 80160
cttatcttcc atatcttttt cttctgcatt ctaggttttt ttgtttgttt tttggaagga 80220
ggatatataa agtaattatt actacatttt tagctgttgc caagttgaaa gtcagtgttt 80280
agtttttttt aaaaagggct atttagtgtg gaattcctaa atattatagt tccctcttct 80340
gtcctttcag agctattgca ccctgttaaa ttttttttgc attcagttca accagtgttt 80400
gaaaattacc aatagactta aagtacttct ctgaagttag aagagctcct atgtctgatg 80460
ctatattgct agtatttcta ttcaggttgg aatttggaat agtcattatc aaaagttatt 80520
tgtaggcaaa agaaaacaaa aagaaaaaag ttatctgtag gaaatattgg agactggggt 80580
acaaggtaag tgacacagtg aagaagcaca gacaatttca gaatatgaga cacctaacat 80640
ggtttctgca aggtattggc gtggaaaaaa aaaaaaaagg gggggggggc ttagagagtt 80700
actctccagt aaaagagata taagaagcag tactatagtt atatacaaag ggtagttctt 80760
tggattctgt ttagatcaaa ttaactagaa aatacatttt taaaataaga tggggaattt 80820
gaatattgac tggtattact taatatcgtg gaaatatact tattttgaat gtgtatagtg 80880

```
actttgtgag tatgaaaggc agtggccaaa ttatttagtg atacataatg atgtatatgg  80940
atgagggaag taatgacgtg atgtctggaa tttactttaa aataccttgg aaaaaatgaa  81000
taaaagatag ataaagcaat attgctaata tttcagtacc tgttaaatat aggtgacagt  81060
atatatatag aggttcatta tactcctttc tccacgtttt gaaaaatttc atttaaaaat  81120
tcaaaaaaat tctaaaaaat attttttctt ttagaaacta acacatgctg aaaaaattca  81180
aattttgttc actgaccacg tttttgctgc caccactctt tcaacattta aaaaatgttc  81240
ttaaatcttt aaaaattcga tttacatttt cattaagaaa atgaggcatt tgctggccat  81300
ttcatccttc ctcttgtatt ttttctcctt acctgctgcc accgtttact agaaaaatat  81360
ttctcttgtt ttttctgtac cttctccttg aaatataaaa gttcagtgaa ggcaggagag  81420
attttagccc gtttttgtat ggctgcatct tccttatcca tacctgcata gcatgtggta  81480
ggtgctgagt aaatatttga atgactgaat gggtgactga atagactgaa tgaaccagag  81540
ttgtagaaga catggggtga cgtggggttt ggctaaggac agaaccaagg agaacccctt  81600
tgaaaattca ctctgtggga tttacagggg aaaatgtggg ctactacata agaaattaag  81660
ataagaaatc atctttcctg tttgactgta aagccttaat atttcaagca tttaacatat  81720
tctcagcata aataattaag tttttttctt ctttttttctg aaacagtctc actctgttgc  81780
ccaggctgga gtgcaatggt gcgatcttgg ctcactgcaa cctccgcctc ccaggttcaa  81840
gtgattctcc tgcctcagcc tcccgagtag ctgggattac aggcatgtgc caccacgcct  81900
ggctaatttt ttgtattttt agttgagacg gggtttcac catgttggcc aggctggtct  81960
caaactcctg acctcaggaa cccacctgcc tcagcctccc agagtggtgg gattacaggc  82020
gtgagccact gcgcctggcc agtaattaag tttttatact gtaagttctc taattgtctt  82080
taatgtattc ttgaaagtgt tttcctccta atttatttat tactgcaagg caatccgttc  82140
ttgaggttct atttaaagtt tatgtatttc ttctcaggaa aaaaaattac ttaaaactag  82200
tggtttgtac agtcaagatg agttttagaa gctgttctta taatttcttt ttatgttaaa  82260
catatataat gtcacatttc ccttttccta acaactgatc ttctttcttt ttcaacgtgt  82320
atttataagc tagattttta aattttgctc cagggactgc tgtagttgtt ctactactta  82380
aaaaaagaaa gatgttagta ttgaacacta ttctgagaca cagctgataa caattgtgct  82440
caacaatgaa gatggctaaa aattgggttt taaaaataac agtgaaaatt cagaagcatt  82500
ttatacttgc tattctaaag tgagtatttt tctaatctct gctttaaaat tactgaagtc  82560
cttttaatga ccaacgctgt attttaagga aaaaatgtga gcaaagattt ttagtgattc  82620
taaatttgtt ttgctctctg gatctcttta aacttttaaa aattattgaa gaccccaaaa  82680
agctttgact tatgtgggtt atctctcttg atatttaccc tgttagaaaa taaagctgag  82740
aagtttaaat agttttcatt tattaaattt atttaaaaat aacagctaat tacatgttta  82800
cacaattaac aaagtctggc ttacaggaag acagttggat gctcatatct gcttttgcat  82860
tcagtttgtt aggatattac atgctctata ctctgacaaa aactttactt tgtgtatact  82920
caagagacag agtaaaaaac ataagtaaca tcttagtatt atagaaataa ttttgatctt  82980
agaaactcca tgtaagtgtc tcaggaactc ccagggttca tattttgaaa attgctggag  83040
tcatctctca gaggctatgt gtgacaaatg gtgtttttaa atgaaacaat aatttttaaa  83100
atatagtgtc aattggctaa gtttttattt gatacttttt ttttcttttt tttttttgag  83160
acagggtctt gctctgtcgt ccaagctgga gtgcggtcac agctcactgc agcctccacc  83220
tcctgggctc aagtgatctt cccactttag cttcccaagt aggaagtagg tgggactaca  83280
```

ggcaagtgcc accatgcctc agtaattttt gtatgttttg tggagacagg gtttaccatg 83340
ttgcccaggc tgctctcata ctcctgggct caagcagtct acttgcaccc aactcagcat 83400
cccagagttc tgggagccgg attcttattt gatacatttt tacctttagg ggaactataa 83460
aaattagctt atgcttattt atgcaaataa atttgagcat tgaggaagga tgtctcttgt 83520
tcagggttgt gtttgtagat ttcacatctt ttagactacc atttaagaga agtgatcacc 83580
ttgtatctta aggaaatgaa aatcatttga tagaaatgga ttgttaaata tttttaaaac 83640
aagttttgac agttacttgc aattaaaggg gaaagcaact ttaaaatgca ttagttaatt 83700
gaagaaatac tcaagatcct taattgttgt tagtgagcaa gtattaatgt tctttcctct 83760
ttgaaaacgt atctgtacct agacaaagtt aattataaac tttttcataa acaatattat 83820
gcttcttttt cttctaattt ttaaacctta tctttgttgg tttgccttcc agctccatct 83880
atctgcaacc taagaatcaa caatactata catcaaatta gctgatgtgg aaggaaaatg 83940
ataaataatg aaaatacgtc atattgctta tactctaagt tataattaat ataagatcca 84000
agggatattg gtgtggggga cgaggaggaa ggaacattgc aagtcaagct atttcacaag 84060
tattctatac ctttgaatct tttatttcat agttttcttt agaaacaata gtgatgcaga 84120
ctgaatagct agtaagataa ctttcattaa tagcagtatg gcagggattt ttaattgatg 84180
cttgttggta atattagaca catgatttat ttataggctt ttaattagaa aactaataca 84240
aatatcaaat tgttatggac aggttataca ttttttggca acacaaatcc taccaggttt 84300
taatgcctgg tacttgtttt tacattagta tgtggtatta attttttcat tactactctt 84360
agcttcccta gcttacccat ttgctaggag tacatagcag cactaggaca tttttcgcta 84420
acgtggctgg catgcatctg aaagtgtgac agagcagggg tatagctaga ttttagaagt 84480
tcttttgctc atttaagaaa cttaaacttc agatttgata gtacttcaga ttctacataa 84540
tgtgctcttt cgatgaatag ctgtgtagca gcagcacagg aaaagcagag ttcttggcaa 84600
tacccagttc aattgcatct gcagatgagg atttaaaatt ctgtgcagca gacagtacct 84660
ccagcaggcg agtaaaaggt tactgcatta tttttcttgt ttgttaccat agcctttatc 84720
taccaaagga tttttaaaaa attgaatgtg aagtgcatgc ctgtttttag atattctgga 84780
aattgattta agtataacat gaatatcaaa agggcagtgc aaggtgaagg cagaggcagt 84840
gctggatctt tttagcttta aaccagggaa gaaattgagc atgttacata cacaaagaag 84900
aaacctttca gtgtcacaga caatgggaag ttttaaaata cgtattttaa ttcaaggtgt 84960
ttattattta gttttagact atcttcccca aaaagggtgc tcttacatta gcaatcattg 85020
gtctatgaat gttcatttaa gttacagtaa tttgaagtat gattatttgt gaagactata 85080
aagtatttgt attaatgcga ccctcccttg tcctggaaat tgtaatgtgg attaattaca 85140
ttgtataaac aaataccttt gtgcattatt ggcaaaggta gaatgcttaa gtataaaagg 85200
tatagtatag ctagcatact taatattgtt gcttatgttt tcagggtggt ttgtggtttt 85260
taaaataatc ttttaaataa aatgcagaca agtaagtggg agaaaattca gtatcaaaac 85320
aatgaggttt ttgatggctt tttacttgtg gtcagtacct acctatatag ccatatgtcc 85380
ttttttctca ttaaaactct tctaacattt atgatagcag gagcctcctt ggattatcca 85440
gcttgtttat tacatcatta tctgcaccag tatttttgct atagattttt attgttcatt 85500
acttctcaag tctacataaa gtatccagag ggaatttttg cttgtatatt ttattcagtt 85560
accctcctac cctcttccat cagtcctcaa agatttgtat tagctactgt ctacattttg 85620

-continued

```
tttatttaaa aaatacttag gcctatattt ttgtattgta gattgaataa taagattgaa  85680
aacaattctg taaattaatc tatagtatag aagtaaaatt tgttgattat tcttactgtg  85740
agtatttggc aggcttcttg aattgtagag tcataaaagg tcagcagttc tgattggtaa  85800
gttaaagaat ccatccagta atttgctccc tgttgtttct caaagcaatg cagcagcagt  85860
tcttttccag atattaaacg gttcttgaac agtgtgtgtg gagacgggga ggggtggagc  85920
tcattcctgt tggttgttga aatcgtgtgc atttacagag ggaacaggtt ggataggctg  85980
agctgaagga gtaggcaaac agatctaaac tgatggaaga cagaaagtgg ttagtataat  86040
tttggggtgt cttgagtttg ctcctttgtt aagtacttgg gctttaatat aaaacaattt  86100
aaaatattaa agcaccttac cttctttcta aagagtagct gggagacttc tgttttaata  86160
tccagttttt cttggcgatg agtttgtggc tggcatcttc tgtagcaaag ctgttgtttt  86220
attctttttt agtagtgttt ctttcagcca gagagctgca gaatgaggca gtttgacaat  86280
tttgagtata tatgtgacat caccagttct gatttttaa gtcaaattct catctaatga  86340
gcaagtcaat gtgtggctgt ggctgcagca ttatttcttc tttaatgaag aggttgagcc  86400
gttcgacctg ctgctccgat ttgttctctt gtagccatac atcagaccag ttgcagagat  86460
tatccatcga atgtcccagg caaccaaagg taactacata gatttatttc aaataaaaat  86520
atgcaatgaa aatggatgca ttatgactaa gaccaaatga ttaaaaataa aagaccaatt  86580
aaagatgttc ttagcagttt tcttgacctt gcagtagata tccaatatca ttttgtcatc  86640
atcagattgt gtagcaatgg aaatgcactg cagtaattga ttttgtaata ggatcaggtg  86700
atttactagc tgcactgaca accacttgct tgcttgctct gagctgtgga gcactctaat  86760
ggatgttgtg atttcagcct ggagtttatg tgagactgcc ggccacttaa agcagcagca  86820
cttattttaa agattagatt agtttttctt tcttgtttc ttcgtttcaa gttttgtgag  86880
tagcctcagt aactttatgg ttaagttgta tgccttcatg aaattttaga gattatatat  86940
tatttcattc atcaattcat agtctttctg ctccatattc ctagctaaat atcaacatat  87000
tctggtattg accatgagag catatctcta aaatatgaga gttattggta actatgctgt  87060
gttatctaaa tgaagtggaa tattcctcac attcgtagat ttcattagct tcagactcta  87120
gctgtaatta gaatgatggt aaggttcttg atctcttgag ttgtactgca gttgttttgc  87180
atcctttttt ggtcttttac tttcttagtg gtttcatggg taaggcacca tttaggaaat  87240
atgagttgta ttacttctaa gggatactga tgaggatata taaagctatt ttaaagtagt  87300
gtttaaggat atagcaaatt aaaaatctaa tatcaagtat tataaatttc aaagtgatta  87360
ttttaaaata atttttgttt tccttttcta tgccttttaa acaaataatt ggttcaaata  87420
tagaagtgta ggaatattgc taactgtaaa atagaactac tgtcatagaa actcagatgc  87480
tgtcaaagac tttgattact taaaagtttt gctgatggtg ttagattaga aaagaaactc  87540
tcttccactc ccttcctcac caatacctct acctcatgta aagtgtttta tacagactcc  87600
accacataaa aatactgaat tctttatcat tccctgtttc tgttcttgcc atgatagaga  87660
caccatttct ctcaaccaca tctaaaaaca tttacaaaaa ttaaataaga ttaacaattt  87720
actgtagtag aaacggggca taaaattgtc atcacatgtg gtattcaaat caccatgtta  87780
agagaacttt cctttttgat gtactcaaat agtcacttgt agtgtttgaa gccttagtgt  87840
ttctagaaag ttgaaaatat tatctgtgct agtctgcaca tttcctttaa ttcagatact  87900
ttaaacatta attatggaaa attgaaaata atttaaacac tagtatttgt aatcttttat  87960
tattcaacag gtaaaaagtt tatagactct cttgacttcc aagaaaaaaa cccttctgtg  88020
```

```
aacactgatg aacataagca tgttaatatc atttaggatt cggtcaagga tgtgtctgaa  88080
tttcatatat attgaaaatg tttaatgatg ggccaccagc aaattaatca tggatatgtt  88140
ttactggagt gccgtctatg acagcttctt ttcatgatgg gttcagcaaa taggaaacga  88200
ggaagtaaac accagagtgt tgactacttt ttataaaagt tagaaagata actatgattg  88260
gtctgtgatt agacagtatt ttatgtaaaa taaatgggca gcgtgaagtt ctagcctcag  88320
tggagctgcc ttttctaaag agccctggat cgagcattaa aagagttgga tttaatttgg  88380
ctctgccatt aatctatttg ataaccttga tcaaattatg tatgaacatt ttaaagtccc  88440
ttaaacatgc tcttaaaatg tccattaaaa agatttcaat ttacccttac cagtgggaag  88500
tattagaata cttgaccttg aagctataga agttagagtt aggaagaagg atgaagtttc  88560
ttaaagaatc aagttgtagg tgatgttaaa acctctcctt tcacttttta tgtctttttt  88620
tggggggtg ggtgggtaac atgtttttgc taagaatact gttttatctc tttgatatcc  88680
aatatttcct aagtaggata gtaattctgg aaattatcct agtggttaat agaatagacc  88740
tgggattaaa atctggtgct gccaattttt tctagacttt ctaacaaaga taatgtcatt  88800
agggagttta ttcagtacct aggatatttt ttagtaaaca cgttttaaga aggttggcca  88860
ttatgttatt ggtgctttct tcctgtatgg cctattagat aagcgctgtg cagtcatctt  88920
tgttgcctag gcaaaatggt ttgtaggttc attgattgaa ctcttacttt ggaccaagtg  88980
ctgtactaag cactttggtt tttttttttt tttttttttt tttttttttt aaagacagag  89040
tcttgctgtg tcacccaggt tggagtacag tggcgcgatc ttggctcact gcaacctctg  89100
cctcctaggt tcaagtgatt atcctgcctc agcctcccaa gtagctggga ttacaggcac  89160
ctgccaccac acccagctaa tttttttgta tgtttaatag agatggggtt ctgccatgtt  89220
gcccaggctg atctctaact cctggcctca agtgatctgc cccgcttggc ctcccaaggt  89280
gttgggatta caggtgtgag ccactgtgcc tggcctgtac taagcacttc tatgttaatt  89340
atgtcattta tgagaaagac tctaatgatt atttttaaag atgagagaac tgaagctcag  89400
agaggttcta caactcctaa aaatcacaca actgggaaat agcagaacca atgtcaaaac  89460
tttaggcatc agcctgctgc tcaaaggaag tgctcattga agcgcttcgg attttgaaat  89520
ttctgataag tataatgcaa atattttta aaaatcccaa atctgaaaca tttctggttc  89580
caagcatttc agataagaga tactcagttt gtatttgtac tttcaattaa gctgtgagtg  89640
tagagatgaa gccaaatttc atctgaagat gtaatataaa tgattaccta attttttag  89700
tcttgaataa gaaatgattt gttcacctct tactcagcaa taattcgtag gaaaaattat  89760
tcatataaag catatttgta ctatttggag taatgttttc caaagtgtgg ttcagggctg  89820
ggcacggtgg ctcacattgg taatcctagc gctttgggag gtagaggcag atgggtcgct  89880
tgagtcgaga agtttgagac cagcctggga cacgtggcaa aacctcatct ctacaaaaaa  89940
tacaagaaaa ttagccaggt gtggtggcat gtgcctgtag tcacagccat gtaggaggat  90000
catctgagtc tggcaggtcg agactgcagt gagctgagct attattgtgc cactgcagtc  90060
cagcctggac agcagagtga gaccctgtct caaacaaaga aagtatggtt caggaatcac  90120
ttgtatctat cactttggat ggtggttaaa agtaccagtt tacatcaggg cacattgaaa  90180
gaatcaccgg aatgggatcc agagatcttt gtttttaaat aagcctctca catgattctt  90240
ggttatacca aattgttaca accaatgata ttgagaatgt tttcctgttt taccttgttt  90300
ctatgccttg cagcttttcc tttaagaatt tgtttacaaa ccatagatgg tttgtaaaat  90360
```

-continued

```
tatccttctg acttatggtg aaatgtaaat tggttctttt gtggtactca ttttaggaac  90420
ttgtttagga ttaaaagtat tcataaactt tgactcagaa aacctacttc taggaattat  90480
agagataatt cctaaggaga tactcagatt cgcaggaaga cttaggcaca aggatgttcg  90540
taccattatc atctataatg gtgaaaaact ggaaacaact caatttcaaa catcagataa  90600
atggtttgtt ttttatatcc atttgtttgg actaaccatc cagccataaa atgttatatg  90660
gggaagattt tgtaagacat aggaaagtgc tcatgattta atgtaaagtc tcgaagaata  90720
taaaattatg gtcatacata tatgtacata tagtgcatat ggtcttaggt taaatcatat  90780
gaaattaccg tttttgtagg tcaagagtag tagaatatca gcattttcat gtagtgtaac  90840
ctaacatggc acccattttt aaagcacatg tttgtagaga agcacatgtt tgtagagaag  90900
cacatgtttg tagagaacgc tttgtagaga aggagctgga aggaaataca gcaaatttat  90960
aaagtgatta tctctggatg atgatattat ggataatttg aaatatttca tctttacatg  91020
tcttatgttt tcaaattttc tactatacct tagactcaac ctttgaaata ggacaaagta  91080
aattaataaa acagggaaca gttgcaaact ttctctgaaa aacattaaaa ttttttagaa  91140
gattgtaaat cctttaagct agtataagga ccccttata ctaatattct taactcttgt  91200
attaattatt gagtgtgttt atgcaaatgg atcatatatg cctttaccta cccacccagc  91260
aaattttgat tggattttaa tctgcagtag aaagtgtctt tcaaaagaag agaaaaaaat  91320
caattttcaa agtttttaaa aagaattggg ttcttaaaag accgccaact atatgcagga  91380
gtcagttggg tagccacgtt aagcacaaag ccctgtttta ggctgtgtgg ttttgatttt  91440
taattgtaat ttaactgatc gataaaactc tgtagattaa aattagtaat ttgtgtattt  91500
attttaaaat attactgtat ttttttgaaa ggaaaatgtt tctcccactt tcatacactt  91560
taatcgttta attttaaaga aatagcttaa ttaaagtaac agctaccata ttctggttat  91620
ctgccataca ccaggttttg ggtgctttaa tatgtttttt gttttgtttt gtttttttga  91680
gaaggagttt cactcttgtt gcccaggctg gagtgcaatg gtgcgatttc ggctcaccac  91740
aacctccgcc tcccgggttc aagtgatact ccggcctctg cctcccgagt agctgggatt  91800
acaggcatgc accaccacgc ccggctaatt ttgtattttt agtagagaca gggcttctcc  91860
gtgttggtca agctggtctt gaactcccaa cctcaggtta tccgcctgcc tcggcctccc  91920
aaagtggtgg gattacaggc atgagccacc gcgcctggcc ttgggtgctt taatatgtta  91980
cttctttcaa tcttcaccta gaatgtatta attagatatg agctttgttt tagcgttgag  92040
gaggcactga aactattata agctttcctg agatcatatt aagtggtgga tctaggtttt  92100
tacctcagta atgtctaact taaagaccca tgttcttatc cctgatactg tccttgttgg  92160
tctgtctgaa acttttaagt gttcataact tgggaaacaa aactgttgta taagccttcc  92220
taattcagac tgtcaaagtg tagagcaaag tatataatga gtcattattg ctgattttta  92280
ttcaactatt tgttacctgt cctttaatct ggtcagtaca tgtgtactgg catttaacga  92340
tcgcctgcta atagctaacc tcttgtgtaa accactggaa atactaaaac agagaagcca  92400
aaaattactt ccttggagtt tacagtccta atgagagaga cagacaacaa aatagttaca  92460
aggtatttca gaacataggt atggaataga acctgttgga acagaaagtt tttaaactaa  92520
taatgtttgg gagtagtggt gaagagttac ttgggaagcc atcttggaag aggtgaattt  92580
agaaggagcc atagatttcg tttttgctac cagcctagga atttacattt taatacaaga  92640
acccctgcct ccagagtgat ctgtaattct actgaagttt gagaaccacc actgtagatt  92700
gtagttgatg ctacgagaaa gcatataata ccctgaggaa gctgtgtgga gtgggaaatg  92760
```

```
agaagttgga aacctcagag caacaacatt gctttgataa gtaggggaag ttatatgata  92820
gttacgatta atatattata agcaatatct tttagtgcct agaagtaaga ttggaaatgt  92880
cttgaatttt gtataagatc acaaaactta caggaagaat atcaaaattc cgattgaggt  92940
tacttttttc tgggagggat ggtgaaatgt tattctttac cctacaatgt gtgattaaga  93000
gtgaataaaa atcgtgttaa ccttttaaag ataatgttta agaaacaggt ttaattttta  93060
aaagaaaagt gagcatagga gcaaagtttt gtaacatatt ctgcttctat ataggaaatt  93120
aattcctaaa ttttggaaat gactagttga aagtaatagc agtctatcct ccaaagagag  93180
ctttttaaaa tttatttttt agaatcagac ctgggttaac ttttagatat aatttggcat  93240
aaccagcaag tcattggtta ttcaaaaata aagattggaa ataattgcca tatagtcttg  93300
gctctttgcg tattttgtga tactgattgt tgcttcctcc tttacttcca ttttattatt  93360
agagcttcat taagagtgaa ttgaaaagaa aactgaattt tattatttta aaaatctgaa  93420
tagttggatt ggggcaactt tcttcctatt tatgagactt cactcattta tgttggtctt  93480
atattgacat taaagaatca gtgtcatata ctggtgaata ttaacaaaga gacaagatta  93540
agattaaaga aattgaacct ttaagcagga ggcgtgtgac taatggagca aatttctgaa  93600
aggcttaggg gtagagaaaa tcaaagctac tgatggtatt aatagtctta gaaatgatgg  93660
agattacatt tttcctctca gagacaggcg acaaagaagg gaggagtaaa gaaacaaaac  93720
ctttgagatt gagatatcac aagttgatag gtacacagct ctctgaaagc ttcagtcatc  93780
tcaataagga gaggaacata cttagccata taagttcgag ttgctgaata tacattctat  93840
gtaggtaggt ctgtgtaatt ttgatacgta ttttctgttt atcacagtgg aaattgttct  93900
tgatcaatgt ttttatttca ataagaaaga tatattgccg cttccatctt aaaatttcta  93960
catagaagag acatgacgct tagtgaacgt tattgaaaaa aaaaaaccgt ataaacttaa  94020
gcaatgaaga aagagaaaca gtgtttcaga atgttacagt attgaacctg aattggtaga  94080
gagaatagaa agtggtgtga acagtcaggg tccaaatgac attctatata aagcatatag  94140
gacatgattt ggagcaggga gtgggatggg gaatgcttag attacatctc tttactagat  94200
gggtgtactt gttctgtgca aggtaccatt ttctcccctt ttttgttagc tcatatatcc  94260
cttcccagtt ttgaagagtg ctccactggt atttataact ttagtgattt gacatttcag  94320
gatatacctg tttcagaaaa tcataagaag ttttaaaaat gccttgatgt aaaacaaaat  94380
ttcaggtaaa cttaaatatt ttaagttttt aataatttgt gttaccaaaa ttaaattttg  94440
gttagagttt gacattccta agtgatagaa tcatcttaaa cacatgttgt caacagaaat  94500
ttgaatgctg aagtcaattt ttgttattgt tattgttctg cttagtgaag aaatgtatcc  94560
tctctaacca gggacagtat gtactgcttt ctccttaata ctttgagatt ttcataaaga  94620
aaataatttc aaaggtgttg tgctgcaagc taaagagatt atttctaaag gaagaatttg  94680
tcattctaat ggttgtcatc ttccttgtgg cattattata aaattaagaa actgaaaaaa  94740
aattttttta gaagacatag tatataccag aatttaaatt tagtttggca taagaggcca  94800
catattctac ctatgctatt acagtctgta tttgttattg cctaattttg actcattttg  94860
aatatctcac tccagtcctt tttattagta tttcttaaaa caaaaatggg caatatgttg  94920
gattgactga aaataatttt taagtgttta gtagcaataa aatttaatct tttagtgcag  94980
attggtttac cccataacag cacatatgga agaagtaaag ccaggtctgt atgaagcagg  95040
aggtgacatt ggactttttt tttttttttt tttttgtgac ggagtcttgc tctgtcaccc  95100
```

-continued aggctggagt gcagtggcac gatcttggct cactgcaagc tccacctcct gggttcacac 95160
cattctcctg cctcagcctc ctgagtagct gggactacag gtgcctgcca ccacacctgg 95220
ctaatttttt tgtatttttt agtagagacg gggtttcact gggttagcca ggatgtctca 95280
atctcctgac ctcgtgatcg gcccgcctca gcctcccgaa gtgctgggat tacaggcctg 95340
agccaccgtg gacttcttta aataaccata gtacaggcag ttacttttgt tatataacag 95400
tatagttgtc tctgaagaaa acctgaagct ctgcaaaatc gggccctgaa aatcggtttc 95460
tgagtggctt gttcctgtgt aaacttgtaa tctctgtagt aacgaaacca gtacccattc 95520
taataaaaat attatatagc taaatattta ccccagttag ttctaagttc taggatttat 95580
gctttctcct ttgaaatgta ggtcctcgag aacattcatt tctacttatg atgaaattgt 95640
gaaaactagt aaatctgatc cagggtgtag tttttatcag ttgcctctca ccccttaaaa 95700
aaaaaaatta acgtgggaaa aatattgtca tggattttct atctgtactc acagcttgac 95760
cagatggttt taacattgtg gaatgcctag cagtttaaag ccattaacta gcctctggtt 95820
accctcttct ggatttctag ttttttttctt aaggtcatca tgtattgctt aagctctgtc 95880
tttgtgagaa agcttgtccc tgctggcttt aaaactttac tatgctgggg aaaattttgg 95940
actaaagtga cattcacatt atactgacct catcgcccaa atgatgaatg aatgaactaa 96000
tgtacactac aagaacatgt cttaatagga aagtagactg ttgtctgtag ttgtcccatt 96060
gttttatcat tgctgctact atattgacat gaagtagcag tgggtgtgca tgtttgtata 96120
tttttctgt gctgttaaat aagtccacgc acatctccca tgtgggtagg gtagtactgg 96180
gtgatggagt aggtttacca gtaccatttg tcccttactt tacttgtata gctttatgtt 96240
ttaaaataga gtgtttttgt ttttttgaga cagagtctca gtctgtcacc caggctcgag 96300
tgcagtgatg taatctcggc tcactgcaac ttttgcctct ggggttcaag tgattctcgt 96360
tcctcagcct cctgagtagc tgagattaca ggtgtgtgcc actcctggct aatttttatg 96420
tttttagtag agacagtgtt tcaccatgtt ggccaagttg gtctcgaact cctgacctca 96480
agtgatccac ctggcttggc ctcccaaagt gctgagatta caggcatgag ccaccgtgcc 96540
tggccacttt ttgttagaat taatactttg aagataccat ggatttggtt ctagaccact 96600
acaattaagc aaatatcata ataaagttag tcacaagaat ttattgtttc cccagtgcat 96660
ataaagttat atttacatgg cattgtagcc tattaagtat gcaatagcat tctgtctaaa 96720
aagtgtgcat accttaacta aaaaatactt tactatttat ttatttattg agacagtctt 96780
gctctgttgc ccaggctgga gtgcagtggt atggtattgg ctcgctgtaa cctccgcctc 96840
tcaggttcaa gcgattctct tgcctctgcc ttccaagtag ctgggattac aggcacccgc 96900
caccacaccc ggctaatttt atatttttag tagagaccgg gtttcaccat gttggccagg 96960
ctggtcttga actcctgacc tcaagtgatc tgcccacctc tgcctcccaa agtgctgaga 97020
ttacaagcgt gagccatcgc gcctggctaa aaaatacttg attgctaaaa aatgctaaca 97080
atcacctgag ccttcaggga gtcacgatca ttttactgct gtagtcttgc ctcagtgttg 97140
atggctgctg actgatagag tgatgttgct gagggttgga atggctgtgt cagtttctta 97200
aaataacaat gaagtttgct gcattgattg actcttcctg tcatgaacga tttctctgta 97260
gcgtgtgatg ctgtttgata gcattttatg cagagtagaa cttctttcaa aactggaggc 97320
aatcctttca aatcctgccg ctggtttatc aattaagtgt atgcagtatt ctaaattgtt 97380
taactttgtc tcaggaaact actttccttg ctcattcaga agaaacaaca ccttatccat 97440
tcaagtttta ttatgagatt gcaacagttt agtcacattg tcaaactcca gttctaattc 97500

-continued

```
tagttctctt gctatttcta cgcgcctgca gtgacttccg ccactgaatt tttttttttt  97560
ttgagatgga gtctggctct gtctcccagg ctggagtgca gtggcacgat ctcagtcagc  97620
tcactgcaac ttgcgcctgc cgggttcaag tgattcttct gcctcagcct cctgagtagc  97680
cctccactga agtcttgaac ccctcaaagt catccacgag ggttggaatc aacttcttcc  97740
aaactcctgt tgatgttgat attttgacct ccttctgtga aacacagata ttcttaatgg  97800
tatctggagt gcagttatcc ttctcaaaag gttttcaatt tactttgccc agatccatca  97860
gaggattcac tatgtatata tataaaacag ctaatgtatt tctaaaacaa gactggaaag  97920
tagaaatgac ccttgattaa tgggctgcag aatgggtatt gtattattag gcatgaaaac  97980
aacatgaatc tccatgtaca tctccatcag agctcttggg tgaccaggtt cgttgtcatt  98040
gagcaatgag taatatttga aaggaatctt tcattctgag cagtaggtct caacagtggg  98100
cttaaaatgt ctagtaaagt cttgcaataa atggatgtgc tgccatctag gctctgttat  98160
tccatttgta gagcacaggg agagtatatt tagcctaatt cttaagagct ctacagtttt  98220
tggaatggta aatgagcact gttctaccta aagtcaacag cagcatcagc ccctaacaag  98280
agagtcagcc tgtcctttag tttggaaggc aggtattgac ttcacctgtc cagctagaag  98340
agtcatggat ggcatcttcc agcagggggc tgtttcatct acagtgaaaa tctgttgttt  98400
agtgtagcca ccttcgtcag tgatcttagt tagctagacc ttttaggtaa cttgctgcag  98460
cttctgcatc agcatttgct gctttacctt gtacttatat gttatcaaga cagcttcttt  98520
ttttaagccc gtgaaccaac ctctgctagc ttccagcttt tcttctgaag ctttctcacc  98580
tctctcagcc ttcatagaat tgaagtgagt tagggccttg ctctggataa agctttggtc  98640
taaggaaatg ttatggttga tttgaccttt tattcagatc actcaaaact ttttccatat  98700
caacaataag gctatttcac tttcttatca tttatgtgtt cactggagta gcacttttaa  98760
tttccttcaa gaacttttct tttgcatttc tagcttttga tttaaagtga gactcttcct  98820
ttttgcctga atgcttagag gccattttag gattattaat tggcctaatt ttaatattgt  98880
tttgtcttag gggataggga ggcctaagga gagggacaaa gatgggggaa tggctggttg  98940
gtgtagtagt cagaatacac aacatttttg ccgtcttcca tgggtgcggt ttgtggcacc  99000
ccaaaacaat tacagtagta acatgaaaga tcactgatca ttgatcatca taatagatac  99060
aataataatg aaaaagtttg aaatactgca agaattacca aaatgtgata cagagacatg  99120
aagttaccac atgcttttga aaaaattgtg ctgatagact tgctcaacat aggattgcca  99180
caaacttcca atttttaaaa aaatatacta tttgtgaagt gcagtaaact gcagtccagt  99240
aaaatgaggt atgcctgtaa aacaaacccg cagaaaaaaa atcgtctact cagaagagca  99300
ctgacaagta tcattgaatt attatatcta caacttgcta atcaagctaa tgtagtgtga  99360
gttgtagata caaccatttt aatgcagggg ttcctgagat ctgaaaatta ttttaagtgt  99420
gcctccagtg tagaaagatt gagaaaggtt gaaagtgaag atcaataatg ggatgaactg  99480
gaaatatgcc tacctgataa tacaaagcaa tgagagaaac atagtatcac ttccgtcata  99540
ttcctgcctg cgatgcataa tgtgaatcca aaattagaca aaccaaaatt aagggccgtt  99600
atacaaaatg aatggcttat aatctttcaa agttgttaaa ggaatgaaaa taaagaaagg  99660
atcaaggaag tatttcagat acaaaactca aatgggttct gaggaataga cagtctgata  99720
tgtcagtgcc attttcctta ctttaacatt tatattgtga ttatgaagaa gtatgtcctt  99780
tttataagaa atgcatactt acgtgtttgg taggggatgg tgcatcatgt tggaaacccc  99840
```

-continued

```
tcccctcccc tcccctcccc tcccctcccc tccccaggcc tctcgttagt agtttccaaa  99900
ccttttgcat gctgaaccca ttgctcaaat gaaggcagaa tattaaacat gtaaaggaag  99960
agcttgtgtg tgggggggg ggagcggggg gaaaggaggt tgggggaaca gagaattagg 100020
aacccctgag tgactacaga acttctgaaa accactgttc tgtaggataa aatctaaact 100080
ctgaagcaca ttatacaaac ctctatctat acacatcagt ttgtctgaaa ttgtatattt 100140
ctcaacaata ttgatctatt tgtatttcaa tatgttgtat gctctcatat gtctgtatct 100200
ttgcaaatga tattttcttc tctttaacga tttttgtctt accctgctgg taaggaagtc 100260
accttccctc tcccttctgt atatccttgt caaggaacta tggaaattga atggcatagg 100320
tcttgataca agaacctctc ttttctcttt ataaaaaagt cagtaaatag tggtggaaca 100380
ttcaggagaa agttggggac atagagacta agaaggcaat gcagtattat taggacaggg 100440
ggtaaactaa ggcatagagg acagatttga tgaacatatt atcttttta tatacattat 100500
aagaagtaga aggctagaaa agtgaacatg cttgctattg cacgtctcac tttccaattt 100560
catgaagaaa gcaaaaacta cttctacttt attacttctt tttgatgtta attggtacca 100620
catagcaagt ttgcattata gtactgagct ttaaaatgca aggatatact catgtatata 100680
cacagacaat aaataatagg ttcttttcca cattcaggaa gtgaaactca gctgtccgta 100740
cgacacttac tgtccatata taggcatccc tcagtatctg caggggattg gttccaggac 100800
cctcacacca aaatctaggt atactagtcc tgcagaacca acatatatgc aaagttggtc 100860
ctctgtatac ttgggtttct atatcccatt aatgtggaga atacttttga tatgtggata 100920
tggagagctg actgtattta ttgaaaaaaa atccacgtat aagtgcacct gtgctgttca 100980
aactcatgtt gtttgaggga caactgtatt ctgttacttc ctatagtttc taaaagcatt 101040
aaccaacaaa tacatgtaag atgcgtggaa taatttttcc atttcctaga aaatagtcaa 101100
tcattttttt ttcagattgt gaactagaaa gcatagtgaa tatagatttt taaacatgaa 101160
aatgtaagtg tccattttaa attgttatgg atatttctgt ttgctgaagt tcaagactga 101220
agactactgg aaaaaatcct gtgactgaga gcacatagat tccttctttt taggtagagc 101280
gcaacagtca ccatgacttc agtgtttgca tatggaagct aaaatctgtc tgagaaaggg 101340
caaacaatca caggagtcat tgatttattt atttgttcat ttttaatgca aattttaatt 101400
gagtgaaaaa gtggtggaaa aaacagttga ctaaagaaga tatgagaagg gttaatacat 101460
gaagaagtcc tcaataatat tagccaccat ggagatgcag attaaaacca caatgccata 101520
ctactttcca tccacaagaa tagctaaaat taaaagaagt cagtcaccac tgaatgttgg 101580
tgaaaatagg aagcagctga aactctctta catggctggt ggaagtgtaa aatggtacca 101640
ttcctgtgga aaactaattg acagtttctt agaaaaaaca ctcaccctat gagcaagcac 101700
tcctagttat ttacccagga gaaatgtcca caaataggct ggcacaagaa tgcttatagc 101760
agctttattc agaatgacca aaaactgaaa acaactcccc aacattcatc aagagaagtg 101820
ataaataaat tgaggtatat tcatacaata gaaagtacac agggacagaa aagaatggat 101880
ttctgataca tgcgacaaca cgaatatcaa aaacagtatg ctgaattaag gaaaaagaca 101940
acaaaagtaa tgcagcatga gtcatataaa catcatataa aaatgatgtt tcaaaatcca 102000
caaaactaat ctgcactgat ggaacagtag ttatctaaat gtgctaagga gtgattagaa 102060
tgggaatggg acatgagaaa agagggaact ttatggagtg atgaaaatat tcaataccctt 102120
tttctttttg agacagtgtc tcgctctgtt tcccaggctg gagtgcagtg tcgcgatctc 102180
gtctcactgc aacctgtgcc tcccaggttc aagtgattct cctgcctcag cctctttagt 102240
```

-continued agctgggact gcaggcttgt gccgccatac ccggctaatt tttttttgt gtttttagta 102300 gagatggggg ttcactatgt tggtcaggct ggtcttgaac tcctgacctc aaatgatcca 102360
cctgccttgg ccccccaaag tgctgggatt gcaggcatga gccaccgcac ctggctgaaa 102420
tattctgtgt cttgattaag gtgttgtata tatagatata tatgtttttc aaaactcact 102480
gcgctttcta ctttatataa aaagtacctc aattaaatta catattaatt gaaggcaaat 102540
taaaaacatc tctgtctgta actctcctac tgtgagtctg ttccatgttg aagaatgctc 102600
ttgtcttctt ttctttgctc ttcttggttg ggacttccct gttctaatat caggtatgct 102660
cacgttagaa agctaggaca gaggcctaga atactgattt ttttccattt caacaggcaa 102720
ggtgacagtt ttcctagagt tcacaactct tggtattcca agtcagcaca tagttcacgg 102780
tgaaacattc tctaggaggt agagagaatt gtgaccgaag aatatgatag gaccaaataa 102840
gtagctatac tagaaggaag cacatttgag accactaccc taaacagcca atgactacag 102900
aaccagagaa aaccagaatc tgccaaattt cagaaataac tcagcatctt tacagggagc 102960
ctctacacaa tcacaatgag actctgaaga gtagcaagta ctgattcaaa tccttttagc 103020
tgtggactcc actctgcctc acaatcattt tagaagaggg ttttgagctt tagaataagc 103080
ccaccactgt ataaaactag tgagtctgtt ttttaaggta ggattcccat cttagtaatc 103140
ataattttgg catggcaatt attaaatatg aaccacaagg agaaaaaaat gtcctcttgt 103200
tattactttt taaattaggc attttaattt catttactac tgcttgatac tctcttctct 103260
gggttcctgg gaggtttcat ttggtaagta ttgttcagta aaaattatgg gacaccattg 103320
ttttggactg tgctcctgcc ctaggcccca gtggaccaga tcaaactaaa atgtagtcat 103380
tcatgttaac tgccacataa tcaaatagaa acttccagga agcagacaga tcccaaagca 103440
gaccattttt ttccctgaga acaggagatt ccagtctagc tgaatcccct gtgctttaaa 103500
cccttagaaa aagtaaactg aagtaacctg atattaacaa atcagctttt ttttcctgtt 103560
ctgtttcctt gttcccacct tacaaaaccc actgttgtgc tgttgctcag taggacctct 103620
cattctacct tgcagaatgg gggctgccct gattcatgaa atgcaaataa atgccagtta 103680
gatctgtaac taaactgttg taattttgtc ttttgacaga atgcagttaa aactcaggta 103740
tatccacact gcttttattt cgtctccttc ccatttcaga aactcctgtc tagatttctt 103800
ttcttgctct ctaaggcaaa caattaccac agttagatga atatgcctgg caatcgctat 103860
tgacagatag actctcagaa acactcgttc cattttcctt ttcaaattct tggcaggaag 103920
actgggtgga tatattgaag gaggtactgt ttgattgtac tgcacacagt gtggtttcaa 103980
aaatgtgtat ttgaattgga aaagagaaat atatgtcagg cactggggat acaatactga 104040
ccaaaggtat ataccctgaa tccaaaaata aatataatgt agttgctgta aacatattaa 104100
ttttaaagat tgtcagaaga atatccatct tagttagacc tttgcaagat atatagataa 104160
gaaaatttct gaaagttaca taactaaaat agaaaccagt caaaatgaac ttcattctac 104220
cctggtttct tccctctaat gttcttatct gtcaatactg tgactgaaaa agccaaacct 104280
accaccacca ccaccactga caaaatccaa aaaactacag atatctacaa cattaattct 104340
aacaccaagt aacattataa cccacttaaa actgttcttt tttctttctt tttttagtac 104400
agacagaact ttttttttt taatggtaag aaatatcatg attttcttat aaagaccttc 104460
tgtatgtaca aataaagcta tactatcata gtggataaat cagtaaacaa tatcttatgt 104520
aatctgtaat ttttcacaca agaaatttaa aaagtttttc aggttataga acagtatttc 104580

-continued tggacacacc taacaaggca gtagctgaca ttctcaaact tcaaaacacc ctcactttca 104640
atacaaataa tgctgtgttg tacatttaac ctaaaactaa gagaaagcat tgttggttgg 104700
ccacaacttg aatttcttat tacaatgagg actgcttcag gattttacca ctaaactcag 104760
ccgttcagag aactaggaag atagtaacca tggtcactgt tcttcaaaag cactgatttc 104820
agatttgttg aagggatatt tcttagatct tcaagtttct gaaaaggttt ccttcattct 104880
ggttttctgg atttccttgt cattctgaag ttattcctct tgcacaggca aaattagagt 104940
actcattcaa taacaacaac aacaacaaca acaaagccat aaaatatgcc ttcttttttc 105000
tacaacacca atttagctac tcaagataca gaactaaaat attagcagaa aatcttgtag 105060
gtatgaagcc agttatgtat tcacattagt aaagatgatt ccactgcatt catttaatca 105120
gcaaacattt acagaatgcc tactacatac caacaatata ttagtgactg catattcatt 105180
taatcccgaa ctctgaaatc attattcctg gtttacaaaa taggaaacag gcttggatta 105240
aggttgcttg cccaaagatt tatagttagt aagattcact accaagtttg aaactcagat 105300
atgtctgagc caaaatttct gctccttcca ctaagccaag ctgtcttcca gcatggcttc 105360
cagcatactt agtatcttgc tgtatcaaga gaaaacaagg tacaggtgac agtgacgtga 105420
tgccattatg actatctctt tttatataaa aagacccttg ttgagataac tacaactctc 105480
tctttctcag acctcctaca cattgctttt ccttcaatca tcagggtcat gagccttctc 105540
ccctctcctc ccccgccgcc ccccaccacc caacttcccc ctaacaaagt aaaagaaatc 105600
aaatgagatt tgattaaagt gttttgtcta gactgcttca ggactaaagg gtcttggtaa 105660
tttgtaccag cacctcactt cttccccacg cccaaaaact cacgtacaca gtttgattgt 105720
tcttgctttc taaagtgttc tctttttttt gagatggagt ttcgctcttg ttgcccatgc 105780
tggagtgcaa tgacccgatc tcggctcaac acaacctccg cctcccaggt tcaagtgatt 105840
ctcctgcctc ggcctcccaa gtagctggga ttataggcat gtgtcaccat gcccagctaa 105900
tttttgtatt tttagtagag acggagtttc tccatgttgg ttaggctggt ctcaaactcc 105960
ctacctcagg tgatccaccc gccttggcct cccaaagtgc tgggattaca ggcatgagcc 106020
cggccaaagt gttctgaaag ctatgtgtga atctgttaag tacaatctat acttacattt 106080
gattataaat attttgacga tctgaattgg taagatttta ggcaaaacaa caaaatcaaa 106140
tcccgtggac tctgacccaa agaatatatt cagctttgtt tgaatatatt tcatcttgct 106200
tccttaccaa ttctcaacac aactccagaa taactgttat taactcttat tgaatcttat 106260
tttgtactaa gccttgttaa atgttttacc tatgaattgt gatttcattg ttacagcaaa 106320
cctatgatat agatgctata taacagatga agaaatgagg ttcagaacct gtgctacgct 106380
gcctcgcagg cacaatccat ctgataaaag tagtcccttg aatctctctt tctgaattcc 106440
agtcccagga cagtggaaat acacagtatt gtggtcaaag ataaaccatt cttggctcca 106500
ggtgagctaa tggttttaga taagaataaa gaatatttat tagaaataaa aaattttgta 106560
agtataaaat tagactagga aaaagctccc ggttgaattt tatatttata aaatccttta 106620
ctgaagttga aatcttctcc ttgaaatttc tgcttggtat ggcctctctg tttgcctcac 106680
aagtgaaatt taatcctaat gttaccttat tttccaagca taaccacacc agtaggctgc 106740
tttgtcatga gtttagtatg gtgtcagtag aaacgagacc agcagtcatt agggttacct 106800
aattcaaatc ttgactcatt ttgggtactt cctacaagat tagaataatt atcttccaaa 106860
ccaaaaacat acccaaggtt ccatgggaaa gggtgtagct tcaactcttt ttaggtggca 106920
agaaaatcat tctctaacct ctcaaaggtc aggaataggg tcgatggtcc ttaaaatttg 106980

-continued gtctggggac cactggttgc tgaacctttt gcaggaggtc tgaaaggtca gacctgtttt 107040
cacaatacat gttaagaagt taatggcttt tttgttgtca ttcttttcca agtgtatttg 107100
attatacaac ttgggatgat gttcctctga tagttaatgc aattatactt atgttttaaa 107160
agtttgttag ttttgatttc taatacagta agtctcaaca gatagaactc acataacaaa 107220
acacttttgg gagtccttca taattttaa gagtgtaaag gaggttctaa gaccaaaagg 107280
tgtggaaact gctcttctag gtttcagaat tatgaagcat acaaagactc ttcatctgga 107340
agggtttaga ggtaatttta tctaatcccc ttattttaca ggtttagaaa ctgattctag 107400
acatttaagt tcccagacta atgtcacaga agctaatgaa ttgcagaggt taattggaag 107460
cctggtctta acactcccag gttatcttaa tgagttcatg aggatggcat atggataatg 107520
cacttcaaag ggtgttgtaa gtattaacta agttaataca ggtcaaatgc atatattagc 107580
actcaatgca cggccattga tcaataaatg ctagtggttc tgatcagtga gaatctaacc 107640
tctgcttaaa tacctttagt catcagcagc ttccactccc tgagtaacat gttgcatttc 107700
ttgatcaatt atatttttac agaattcttc ctttactgaa gttgaaatcg tctccttgaa 107760
atttctactt ggtatggcct ctctgtttgc tacacaaata aatttaatcc taattttatc 107820
tagcttattt tccaagcata accacaccaa tttcattaaa tgattcctca tgtggcatga 107880
ctttaaactc cgtcaccatc ctatttgttt ttctcaaaga gctccagttg actgctcctg 107940
tgaaattgtc catctattaa tgtaaatgtt ttttctaatt ttacagagct ccccgttgta 108000
ttgtgtacag tgttaaaata gttttctgag atttcttgac tctgttttcc caagtttctt 108060
gtggcccttc tctttccttc gtctctattc tgtgcggttt ttatttcact cccacagttt 108120
ctcattgctg tgaggccctg ttatggaatg agagccctgg ttttgaaagt tcacagaggc 108180
tagacttctc ttgtccctgt agtcctggct gagggcccac tacacttgtc tgttatccga 108240
gtgggcaaac gacctacccg ttttcatctg ctgggcggcc ggttatttgg ggggatcccc 108300
ctgttacagg tctgatctct gttgcttcct ttgggaggcc gaggcgggcg gatcaccagg 108360
tcaggagttt gagaccagcc tgaccaatat ggtgacactc ctgtctctac taaaaatgca 108420
aaaactagct gggcatggtg acgtgcgcct gtagtcccag ctactctgga ggctgaggca 108480
gaagaatcgc ttgaacccgg gaggcggagg ctacagtgag tcgagattgt gccactgcac 108540
tccagcctgg gcaacagagc gagactgttt aaaaaaaaaa aaaaaaagtt tgtagccatt 108600
atctctggaa atatttactc ttcctcattc ttctgcttat ctcttttctgg aactccaact 108660
agatatatac tagacctttg attctatttt tccacacctc ttaacctgtc tagcttattt 108720
agtcatacat ctctcaagct gcattcttcc ttggagcttt atctgtagga attctttgag 108780
ccttgattga gtttatattg cttcagagaa aactaaggtt tgcttcagct agttgcccag 108840
gaacattacc acctggttac cacttttaat taaggtcact gcttgaggat ttcagagcga 108900
cacagagccc tgtatgaggg cctgtttatg gttataaatt cttggggtgt aggcaggggt 108960
ggggatcctg cttctttacc tggagctaaa actgagacag aaaaatccct gactgtccat 109020
ttttgtgtgg tgggtttatt ttctgttcac cctgaacaat gataggtgtt caccttgtag 109080
agctccccgc tttatgtggg ggtttcctat tagagaacta tcatatgtgg cctgttggct 109140
tattttcttg ccttcagcac ctgtgccagt acataagtta gaaacccaag gtttccaggt 109200
ttcgaaaaac tctcagggca aaagttcgtt ttagcctatg cttagctccc agggtccttt 109260
gtacttggcc atatggattt cttttttttt ttttcttcat gtcaacactg tggttatatt 109320

-continued tatctgtcta acctactctt ttaatttttg ttttatctgg tattttaatt gtttcatttg 109380
agaaagtttt tcatagtatc tgtttggtag ttggccattc tactaggagt ttaggagtta 109440
tacttaactc cttccaggga gatgttggaa gatttttact aaaaatacaa tatttaaggt 109500
gggtattgaa gtactatcag aggggacctg gggtggagta tgaaaacaaa acaaaacctt 109560
acaaacggga ataattaaga gttaggatat gtgagatgtt tggttttgct gggcttaaaa 109620
tagaattgtg gggtatggaa ttgctgcaaa tgaggaagat ggactcagag atgaggctca 109680
agagaggcca catgcaactt ttgagagtct ttgtgtgtca cagtaaggaa gatgaacttg 109740
tgaaatcacc aaagggtgga atatataagg aggaagctga cactgtcata tctatgcctt 109800
aggatgttta ttttggcagc agtgaaaaca aatcaggtag acaagagtgg agcattgctc 109860
ttcaaaattt agtcattgac tggcagtaat ggcatcatct gggagcttgt tagaaatgca 109920
gaatctcggg tcctatttca gatttaccaa ctcagaatct gcattttaac aagactccta 109980
agtgtttcat atgcatagtc agttgatgtc tcaaccagtg acctgcagag ccagtgatct 110040
gcaaagcaag tgaacgttag ctttatttta aatttcaaga aagaagtctt aatttgccta 110100
gagtacatat catttgatgt tcacagtgtc actttatttg cctaataact agctgactct 110160
agatccttag cagcattaga tttagtattt gaggttttga ccctatgtac ctttgataag 110220
tagtgatttg taacttatga attaaatttg aattccttaa catgttgcta gttacaaaac 110280
tctagtgtct ctagcagact attaagaaat tgagcaggtt tcgttctcca ttcactgtta 110340
acacatgcgg taactcacca ggcgcttaaa acaagtgggc tgtggtgcag ggtacttctt 110400
gtttagtgac agaaatgaaa agatctaaga atatgatggt tttaaataaa tatgataaga 110460
gatgaagaga gttttaagta atagaactat tctaagtttt ggatgtttgg tttagtgtct 110520
ctagctatat ttctgtttaa tgtcaaggca taatatattc gaaccatttt atttattaaa 110580
tttaataaac attgattgtc ctattagtca aagtttcaga aaaatgcaaa aagtcttgtt 110640
ctcaaaggaa tgctccctgg accatgcaca tcaaagtcgt gggtggctgc ttgtgggggt 110700
agaaaatatt aaaaatgcag aaactgggcc ctactgccga atcccaatgt acattttaaa 110760
ataagcagct tcctggccag gtacggtggc tttcacctgt aatcccagta ttttgggagg 110820
ctgaggcagg aggatcactt gaactcagga gttcaagcct gggcaacata gtgggacccc 110880
catctctgca aaaaatggaa aaaaagtaaa agcatctccc aaggaattct gccagcagga 110940
aagttgtgtt ttcccccctc aaatctggaa accataattg ttcacttttt gaccttttac 111000
tggaatacag catactctga gaaaagtaac aacactcaaa taaaaaaata gaacattcta 111060
ttccagaacc tcctctagtg actccttcta gaaagcagtc tagcacccca cccctccaaa 111120
cacaaacata accaccatag tgacttttaa caccatagat tagtttttcc tttttttgaac 111180 tctttaaagt ggaataatac aatttatact ctgtctgttt tgtgttgttt ttgcttagca 111240
ttatgtctgt aaaatttgtc tatattgtta gctgcagttt gtcattctca ttctcattgc 111300
tgtgtggttc tctgttgttt aaaagtacca gtggtaaaat tatcatttat gtggtttatc 111360
tctgatggac attagaggta tggtggtacc actgataggc accaaaatca agtttaataa 111420
ccactgttgt atattatttg ggaaaatgtg tactcttgac atgtttggca aatttttatt 111480
tctccaatct aaaatttaga aaattataat tttaaaatta tcaataaaaa tttacaaagt 111540
ttttactgtc aaatattatc taatagctca actagctcat gctagagtaa tacagccatg 111600
taatacagca ttaccaactt ttctaagtgg tctatagcac tgaggaatta aatagcaaat 111660
aagggaagca tttcttcatg aaatcatttc ttttaataaa ttaaaaagaa atgagagtat 111720
tagaatacca ccattttgcc accttcagtg tattaatgga tggaggcaat gaatatcaac 111780
agctgctaaa atcataagaa ggaaaccaga tgctagatga cacataatga agtaacacat 111840
tattagacaa aggaacaaac caagttcaat aaagcctctg gatccagctt ccaatttgcc 111900
acaaataaag agaccagatg aatatgctga attgcattat gtgtaaataa tcagtcaaat 111960
ctacactacg aaaagtcaga tcaaacataa attttaagaa aaagaaaaga atggaaaata 112020
aacctgtaga ttaaaagaga ctgaatagaa gtagcaactc ttcttaaaaa tggtcaagat 112080
taaataatag ttatctaggg aggcttactt agctgataaa gtgataaata caggatgtaa 112140
ttaagaataa tttaaaagaa gtgagttact tagaggaagg gaaggggcta tgactgaatc 112200
agcacttgga ggagcttctg ggctcgctgg caaattgctg tgtggtggtc acaagaatgt 112260
attctcttaa tatgctaagg tataaagttt ttgtatagtt ttctgtatct gtattttatt 112320
ttactctaaa ggaagtagtt ttttaaaaaa gattatagat ttgctaatct aatataaact 112380
cccctagagc ttcatcagta atagtctagt gtcatctgga ttatcttcag caatcatttt 112440
cattctaaat tgtcatagtg tcatctcaaa gcagaaagag acagagagtt tgacaaagtg 112500
tcttaaaatg cctgatgtct gtcttaatga ttctaataga aactcttcag tacaatactc 112560
agacttactg cgcttacaac tacataatgg cttataaatt tgggaaactc aacagatttg 112620
ggaatacaac acatatcttg aagccagtta atttactttt tacatacctc ttcactattc 112680
cactaccagt gtgcaactgg taattcagtt gaattcataa agaattcact gagtttttct 112740
gaatttcttc tgatttcaag aggctagaag aactcagatt ataaagcatc aggttatcac 112800
ttttactata taggcacacc atggtttatt gcactttgct tctgattttt tttttaaaca 112860
aattgaaggg ttggagcaat cctgtgttga gcaagtctct tggtgccatt ttccagcagc 112920
tcactgtgtg tctctgtgtc ccattttggt aattctggca atatttcaat ctttttcatt 112980
attattatac ctattatggt tatctatgat cagcgatctc ttttatgtta ctatcataat 113040
tgtttgggga tgccatgaac cacacccata gaagaataaa agatggcaaa cttaataaat 113100
gttgtatgta ttctgaccac tccaccaacc agctgttccc atctctcttt tctcaggcct 113160
ttttattccc tgagacacaa cattgaaatt ttgccaatta ataaccctac agtggcttct 113220
aagtgttcaa gtgaaaagaa gagttgcatg tctctcattt taaatcaaaa gctagaaatg 113280
attagtgaag aaggcatgtt gaaagcagag acagggcaaa agctaggcct tttgtgccaa 113340
acatccaagt tgtgagtaca gaggaaaagt tcctttcttt ttttcacttt ttcgtatgtt 113400
taaaaagtag agacagggtc tcgctatgtt gatcaggctg ttcttgaact cctgacctca 113460
agcagtcctc ccacctcggc ttcctcaagt gctgggatta taagcatgag ccactacacc 113520
cagctgaaaa gttcttgaag gaaattaaaa gtgctactct ggtgaacaca tgaattataa 113580
gcaaaacagc cttattgctg atatggagaa agttttagtg tctggataga agatcaaatc 113640
aaccataaca ttcccttaaa caaaagccta atccagagca aggcccgaac ttacttcaat 113700
tctatgaagg gtaagagggg aggaagcttc agaagaaaag ttggaagcta gcagtttggt 113760
tcctgaggtt taaggaaata agctgtctcg ataacatgta agtacaaggt aaagtagcaa 113820
gtgctgatgg agaagctgct gcagcatgtt atctagaatg tctagctaag atcactgatg 113880
aaggtggcta ccctaaaaga ttttcaatgt agatgaaaca gcactctatt ggaagatgcc 113940
atctaagact tttctagctg gataggggaa gtcagtacct ggcttcaaaa catcaaagga 114000
caggctgact ctcttgttag ggctaatgc tgctggtgac ctcaagtgga agccagtgct 114060

-continued

```
cattggtcat tccgaaaatc acagggtcct aagaattatg ctaaatctac tctgcccatg 114120
ctctgtaaat ggaacagagc ctggatgaca gcacagtttg ctagatatgt taagcccact 114180
cttgagtcct actgctctca gtgaaagatt cctttcaaaa tattactgct cactgacaat 114240
gcacctggta acccaagaac tctgatggag atgtacaagg agattcctat tttttcatgc 114300
ttgataaaca taataacatc tattgtgtag cccgtggatc aaggagtcat ttctactttc 114360
aagttttatt atttaaaaaa tatatttctt aaggctgtag ctgccgcagt gattcctgtg 114420
atgaatctgg gcaaagtaaa ccaaaaacct tctgggaagg attcaccatt ctaagtacca 114480
ttgagaacat tcgtgattta tgggaggggg tcaaaatatc agcattaata agagttggga 114540
agaaattgat tctacccca tgggcaactt tgaagggctc aagactacag tggaggaagt 114600
cactgcagtt gtggtagaaa tagcaagaga agtagaagta gaacttgaca cagcgtgaca 114660
attgctgaaa tctcaagata aaatttgaat ggctgaggtg ttgcttttta ttgatgagca 114720
aagaaagctg tttcttgaga tggaacctac tcctagtgaa gaggctttga aaattgttga 114780
aatatcaaca aaggacttag aatattacat aaaattagtt gacaaattga taaagcagcg 114840
gtggtttggg aggattgcct ccaatcttga aagaagatct acagttaggt aaaatgctgt 114900
cacatagcct agtgtctttc atgaaaggaa gagtcaattg atgtggctaa ctttattgtt 114960
gtcttatttt aagaaattgc cacagccata ctgattagtc agcagccatc aatatcaaga 115020
taagaccccc caccggcaaa aaaattggac tcactgaagt ctcagttgat cattagcatt 115080
tttttaagca gtatagtcct tttaaattaa ggtatgtaca tttttttac acataatgct 115140
attacacact taatagtagt gtaaatataa cttttattgc actgggaaac caaaacattt 115200
tttgtgacct gctgtattgc aatattacct ttattgcagt ggtctggaat tgaacctgca 115260
gttttctgag gtgtaagtat tggtgaaatc attaacctcc tcctctgtgt gtgtggtttc 115320
ttcaactcac aaaggatagc agccccagtg aaagtcgtta cagaaggcag ataaactcca 115380
tttttttaa gactttgcca ctctgtgtgt gtgtgtgtgt gtgtgtgtgt gtgtgtgtgt 115440
gtgtgtttac cttatcctag tgggccttac cacacatttc tattatgtga gatccaaaag 115500
tgatgtggta tacacaagag taattttcac cccattctta aaactgaaaa tgatgtttaa 115560
atcacttttt cttgggggaa aattcaaccc cgtggtaatt aagcttcact tttcctgaaa 115620
ttaatctttt tataaatttt ataaacttat aagaaatgta atacattttg cttaagtaac 115680
tagcataagc caaaatggca cttcattttt cttaggctca gcagatttaa tttaataaag 115740
attataaatt gattttaatt aatgatgttt acgaaatgaa aattaattga cagtgttgaa 115800
tagtaaagct gctaaaacca taagccaaag caatatgaat aaaagtataa tttagacaca 115860
attttaaacc agattttgaa aaactttact cggtgatatg gtcaggctca attgtatgcc 115920
tgctagttag attacttctt gtataggctg atatatgcat aaaattatta tttttgaatt 115980
ttaaataaaa ttatatttat ctctttaatg tgaatttacc tctttaatgt aaaaattata 116040
tttgtttttt gtccttgttt cttactgcac atatcaattc caggtcaagc atgagataag 116100
caaatcatgt taatttcatt ttcaactgaa ataagactat ttctgagctt attcttgttt 116160
gctgaataaa aaaagattgt tcatatgtgc gagaaattgc tgcagcataa tgttcactgt 116220
ttttctgtga gtagcaggat aatcttttct tcatagaaat ctacatcttg tctgggaaag 116280
attagtaaaa ctcatcttta atgtatgata aaactgcaga tctttttcct tttttctcaa 116340
gtcaaatttt cacagtcaga acattcagaa acaggatccc ttttccagtt ctacacttgt 116400
gttcaagtga aggaaaatct gttcagtttt ttttctgcag ctcctccagg tgatttccag 116460
```

taagacttga gacttgctga tatccttcct cactctcaag cccaaacagc aatagaaaca 116520
tttcaagatt ttcttttgta acatgttttt caaaagctca ttttcctttt acatccaaga 116580
atgttgtcct ttgaaataaa gaaaacccaa ccattttctt cacaccttac agagactgaa 116640
aaataagtac tacgtaggct agtttctaca gccattaatg tttaagtatt caacagactg 116700
tagcctactg ttttctttaa aggacccatt tcagttcaaa taccctattg agaagttttc 116760
cactgctaag tggattttgt gtgtgtgtgt gtgtgtgtgt gtgtgtgtgt gtggtaagag 116820
ctgttcttta aatgagtgaa atgacctttg tttaatgaag ttaaccattt tataacatct 116880
ttcagatgtt aaaacatttt gccccaagag cttttgatat cagtactctt aacacagatg 116940
ttttttgtgt tagtttgggt cttctgagac acagatgtca agacaagatt tgatgcgcag 117000
ggaatctccc accccaccct actaccctcc tattgtcctt tggagcaatc cccattctag 117060
tacttctgcc ctgcttggta gcttgctggg agaagcccag aggcagcaag gccaggggtg 117120
gttgccatgg attccaaggt gcgatagatg gaggctgtca agcagttctg ttcctcatag 117180
caggttaggt tgaggggata tctgagtagg gtaccactgt ggccactgca ccctcctctt 117240
cagcctttga catctttccc tcatgtggac actctttact gtgttacgca cccacaggga 117300
tgttgtcact gtgttctgcc tttgacctac gggggcttct ttactatatg gattattcct 117360
catgcttctt agagtcaagc tttgccacct tgcccccttg ttggtctgcc tctgttcctc 117420
cccgccgcca tccctcacta cagaaaggct cttttcattc tgctttgact cccaaatttt 117480
ggactacctg cctgccacat acatacctaa cttgcttggc tccatctaat agctttttga 117540
ctaaattttt gaggaaaaga aggaagaaga gccatctggg tttcttacat ctgcaactag 117600
ctagaatatg attccattca ctgaaataga gaaaataata ggaggctcta agaacaaatt 117660
tgggccttac gtatgtgtgc atgttgtggg gaaatagaag tttggatgtt aaaataatga 117720
atttggtgtg actttgggac accttcttga aattaatagg ctcagtagag gagtctgact 117780
ggagataata gtatggggag tcattagctt ctgtgtgata gttggaaccc tgactttcaa 117840
cgaaacaaca aaggagggag gagctagcga tggagcacag taacagtgct gcctgaggga 117900
tgcactgagg aatgtaccaa ggaaaattaa gggacaggag agagttgtaa agagagctag 117960
tgaccaacag aatataaaga tacaaaaatg gcaaaagagt ctttgagatt taacaaccag 118020
tttaaaattt agttattatg gagtaagccc atatcacaca ggtggtggcg tatcacacag 118080
ggattaaatt tagccaaaac aaaatatgta ttataattca aataacaaaa aatatatatt 118140
gtcatgtgga ctgaggaata gtcttttgca tcctttccag taaagatata tatgattgac 118200
tagtgaagtc tatttaaatt attcagtgta catccataaa actttatcaa ttactttctg 118260
tgtatatgat gacacttgcc agtattgccc attttgtgct gattttgtta gtgtacatta 118320
ctaaggagct tttcatcaaa ttttgcagtc cctgaaagat tttcatcttt aaagttacaa 118380
atgtgatttc tcagctgcag tatagaatat atggaaccag aaatactcaa aaaataattg 118440
ttttcgaagt attaatcttt ttagtcacag ttgttttttt acatcctgtg ctgaaaataa 118500
caagaaattt gatacagagg gaaaaatgat ttattatgac ttagtagaca atttacaaat 118560
gtgtgttaag atattaggat atatgtccta ccagtttcaa aagtactaca agtgacttgt 118620
tcaatacaga gtacaacttt aaaaaatgta tttaaagtaa ttgacgttgt gtttgtgacc 118680
tggctcgaag ttcttttttg gtgaagagca tgcttagtac atgattgtct ttaaaaagat 118740
ctgataatta tttactcagt aaatgttttg agtgccttat gagtcaggca tttttgtggg 118800

-continued tgctggagat aatagtgatg aaaaacaaaa gtccctttc cttatagaac ttaaattcta 118860
gtgtgggaag gcagatagta cagaaataaa ttgatggatg gatagatgga taggtaggta 118920
tttgctatat agcaggtact atttttgctt ttatatagtg ctgtggaaat gagtaaagtc 118980
aggacaaagg aaaagagaag gtgatgctgg ggggtattat tttaagttgg atggttaggg 119040
aaagtatcat tgaatagggg acatttgaac agagtcctct atgaaggaag taaaagaaat 119100
aaaaagagga atagctagca caaagactct gaggttgcag cacactttac ccctcaagaa 119160
agaacggtga cagaaagggt ggaacaaagt gagagagtag taaaatatga gttcacagtg 119220
gtggggatgt atgtagatga tagaaggacc caacaggcaa ccataaaaga cattggcttt 119280
tactctgagt gaaatgggaa gctcttagtg ggtgttgagc agtggagtaa taagataaaa 119340
cttatttcat catgcatttc aggtacttac tcctaatcat agtaattaat aaattattaa 119400
tttggggtat agaaagttca tatatgaagt ggagggtgtt ggctctttta agaattcagt 119460
gaaaatccta aacttcttgc agaaagtgat tccaagcttt gagttattct tcctgatgat 119520
cagtacagtt ggtttacttt cttgttatct ttgtcctaaa gcttcttaaa tcactttgta 119580
gctcaagcct aatggattat acctgcccat gtaaattctg aaaatgttaa tgttgcctag 119640
tgattcagag gctttagtaa tttacttaaa ctacttcttg ttttattggt ataaactgta 119700
ttcctcagtg tctactatga tttcaaagtt agtatttgcc ttggaatttt tctttgaagc 119760
tggcaactct agttcaatat aagacaggct ctcagagctc cacttattta acaactgtat 119820
ctatgcccac ttttattcct ctaagcattc ctagaataag catttcaaat ggttttgaat 119880
tatcaaaggt ctttttgaaa aacaaggtta ttgagaaaat gtttaaaaag ttcatgagaa 119940
agttgtctaa aatacacccc cctcccccaa ggtaggcctg aaatgccact aaatcaacaa 120000
aggatagtca ctaaaagtta ccctgtattt tctaggactt ggggaaagtc atggagtagc 120060
tgtgctttct ctaagtaacc tattttaaat ttttttgaag agcaaaatta ttatacctct 120120
ttttcatcca gaatggagct gactgtaggc atctttttaa agtacccata ggtcaggacc 120180
tctctggact ttccactacc ttgaaagaca ctgccagaag aatgttgttc cccacactta 120240
aaaaaggaaa agtaatgttc ttttctccag ccattatttt atgcaaagtc caactttatt 120300
ttatctgagc tatctgaact ttcaatttat ttgaaacatt tattgattaa tatctataat 120360
ggagctttta atttctctga tcatttatcc tttgttaggt tagcagaact gtaacaacac 120420
agtcactttc acagccacga atgatacttt tatagtcatt tgtggacata tactgtgcag 120480
agtatcacaa agtttgagcc acctgacaaa cttatttcca gttgagatct gcagggtgat 120540
gctctgcctt cttgttgcag ctctcatacc atgaacaagt gtcattttca tggtccatga 120600
ggaaaaagca ttttcctcat tttggtgctt tttgttagtg attgtgcagt ttagaatggc 120660
ccccaaacat agcctgaagt tctgtttaat gttccgaagt gcaggaaggc tgtaatttgc 120720
cttaaagata aactaatgtg tgttaaagaa acttaattca ggcattagtt ataatgctgt 120780
tgaccatgag ttcgatgcta atgaatcaat gtatattaaa gatatattta ggcagaaaca 120840
cgcataaaaa aggttatgca ttgatcagtt ggcaacagtg ttgtgaccag aggcttgtga 120900
gaactgtatt tcccctagga gcaatggctc agtatttgtt aattcagtgg ttgcagcaat 120960
tttatagaac acaattactg tgaatgggaa tcaactgtat ttgattaacg gtggtgattt 121020
atagggactt tagataccag aaatgtttca taattccctt tctctgaaat cactgtttta 121080
atatgtttaa atgcatgcat gcagagttgt gatgttaaac ataattttac tgtgggttct 121140
ggtcaaaaaa gatgaaatgt cattggttaa cttgaaagag acattattct aaacattatc 121200
ctccagaaaa ttgacatgta caggaagcat attgaatgct cagcaaataa tttgttttag 121260
agtaataatc tttgagtatt gtagtgattc gagttttgga aaagaaggca gtatcagtgt 121320
tagagaataa tattctttca ggattttatg tagttacttt aaggtgcatg aaaggagact 121380
cagttgggtg ttaaattctt gtccctgctt tacttgaaac tagtaatctt gagaaattta 121440
ctaaatcatt ttgagccttg attaccttgc ctgcaaagtg aggaacattt tcaatttaaa 121500
attctatttc ttttattagt attcttcctg accttgaatc atttctattc ccatcatgtc 121560
cagttgccaa gaaaaccatg caacttaatg ttgtttgtta gccatcagat tttattttac 121620
tgaactcaag ttcagtcaca tcagttaccg ataaaataat aagttctata ttaatatttg 121680
atatatcttg acattttgta ttatggtagg aagaaataaa agaccttcct caaattttag 121740
gatatgggct tctgtttgtt gatgtttgtg ttttatgata cactgttgta aatcatacta 121800
aaggttttct ctgaaaaaga ctagaattga caatacttca tttgttagca gtttcaagtt 121860
ttagatcacg ggtgcataat ttcttgtgtg tgcacaacat gttggcattt tatctgactt 121920
caaagatgtc catatagata ccagcaaagg ataaaatgta agaatgaata tcatgaaaag 121980
atgctgtatc agataaaatt ctagagccta ggttaaaaaa cataaaggca aacatgcttg 122040
atatataaaa attgagaaat atgataaaaa gaagtaagtt taaagcatca gtaataccac 122100
tgcctaagat gcagtttatt ttgaaatgtt gtcttctagt cttcatacag tttaaaaatc 122160
atactataat cacaatttcc agcattttcc ccttagcata atatattata acatccatgt 122220
ttttaaaaat attttatgaa cgtcatgttt agggattaca ccatatatat cccatctcat 122280
agattccttt atattgaaca tttggatttt tatttacatt tttatttaca tttattttta 122340
tctttatttt ttgctttcgt ggataaactg cagtgagcat cctctgtata aatttttttt 122400
ttctgtttta ggattacttc cttaggatag attgccagaa gtggagttac tgggtcagag 122460
ggtatgaact tatgaacttt ttttttaaat aaattttttg ttcattttct gtccagtcat 122520
ttgtaaaaaa attaaaataa taatgattat aattgttacc tgctagaaaa ctgtgtctga 122580
aggcaagatt ctgtgatcag aaaagtttgg gaaataccca gggtaaaaag ccttttaatc 122640
tgatttacct cagcatttcc caaattaact gaacactgaa aatttttttt gatacacttc 122700
ttaaaatttt gtggaagttt tatataggat atagtctatg aactactgat gtaaaattaa 122760
aattgtttta tttgcttgaa atattatgtt ttattggtca aaggaattaa actataaatc 122820
ttcatgctaa aaattattaa aagggattag tgttgtttac tatggttttt gtgcatgtct 122880
ttataaagtc ttataacttt taaaattgaa atgttctata ttgtttacta aagaacattt 122940
taatgccttg gtggcatcaa tacttttttg caatcattaa tgatatttag aaagtagaca 123000
tataacatga aagtagaaca taatatagat tgtacaaatc ttgtttttta ccctattttc 123060
ccctgcag 123068

<210> SEQ ID NO 5
<211> LENGTH: 23
<212> TYPE: RNA
<213> ORGANISM: Homo sapiens

<400> SEQUENCE: 5
uuauugcuua agaauacgcg uag 23

<210> SEQ ID NO 6
<211> LENGTH: 102
<212> TYPE: RNA

<213> ORGANISM: Homo sapiens

<400> SEQUENCE: 6

```
gguccucuga cucucuucgg ugacggguau ucuugggugg auaauacgga uuacguuguu     60

auugcuuaag aauacgcgua gucgaggaga guaccagcgg ca                       102
```

<210> SEQ ID NO 7
<211> LENGTH: 2469
<212> TYPE: DNA
<213> ORGANISM: Homo sapiens

<400> SEQUENCE: 7

```
agatggtgta gatcagatcg atttgattgc attagatgat tttttccctt ccccactcct     60

ttctggaagc tcgcatcagc tgaaggctat cgcctgggac tcctcggaag catgagcaag    120

ccgccaccac gcgaaggcac tggggcacag ccagcgcgag gcgccgaggt cccttcccaa    180

ggcttgttaa cactgtaacc cggcactcgg agagaagaag cagctcacac tgcccagagc    240

ctacctcact gcacatcaga tgactccctg gcttctacac acagttggag ttccgcttga    300

aacctggatt tagaggggtt ctctggccgc catggcactc aatcatacca cctagagtgg    360

actggccgag accagactgg gtaccaagca gagaagtgca gaggaaagca ctgggagagc    420

accagaattg gaaatagagc ggccatttgg atttgggcag gaagcagccg agcacagctt    480

tggatccttc tttagggaaa tcgagttatg gatttatggt cccggtcaag ctcagcccat    540

ccccaggcag gggcgggctc agcgagcagc aagagttctg gtggcggcgg cggcggcagt    600

agcagcggca gcggtagcag cggcagcggt agcagcggca gcggcagctt ggtcctctga    660

ctctcttcgg tgacgggtat tcttgggtgg ataatacgga ttacgttgtt attgcttaag    720

aatacgcgta gtcgaggaga gtaccagcgg caggggggca gcggccgccc tccccagccc    780

accagctggc cactaaacgc ccgtggttgc caaggcatcc aaagcctctg ggatgtgttc    840

tgactgtaaa aactctgatg ttgtgaaaaa agcttacgct ttgcctccac tcaaaccaga    900

tggtgtttcg ctcttattgc ccaggctgga gtgcaatgac gtgatcttga ctcaccacag    960

cctctgcatc caggattcaa gctattcccc tgcctcagcc tcccaaaatg ctgggattat   1020

aggcgtgagc caccacgcct ggccagcatt cccaattttt aaaaatgaat gattggcaca   1080

aatcttagaa agccattttc tgtagatttg aaagcaatgc tatttacatt gttactactt   1140

tcttgttaaa tcttgcatgt ctgcagtatg tgttgtaata gaaacctaag attatgatct   1200

gctgtattca tatttgaaga agaaaatttc agactgtata atcaactagt tgatgattca   1260

tatttgcttg tacaaagtta aaagtgtaac ttgccagaaa agaaggaagc ctgaaaagta   1320

ttctaaatac attaataaga agggttctac atgaattaat ttttgttttg ccatctacag   1380

agttcctgcc acattctagg cacttcatat ttgctgcaac atttattcag acattgacag   1440

aacaagagaa acgaagttaa attttaagta ccatggattg aaattaaatt tagggaagat   1500

attttatagt atgaattgtt catctgtatt taacaaggta ttcatttatt ttgggcgatt   1560

taaggaaggt cctttctgga aacaggatta caaacatatg gacctattta gtcaatttca   1620

accttgtgat tttgaatctg acaggttctc agctgctttt attaaataac ggattttctt   1680

aataattact gtactcaaac ttagcaaaaa gctctattta tagcccagtt ttttagtcac   1740

acactattgt gtcttgtcaa attgaaacca tatactacat tctttactta ttaagatggt   1800

ctttctttgt aataattttg gagtaaatag tttacttatc taaacctctg atttctgatt   1860

taacagattt ttgaagcatt tattttcctt accatacata aaaattgtca gttgaggaca   1920
```

aggaaggatt aacctggact acggtgaata attgttcagg ttgcttactg tgtaactcca 1980
gaggagcatt cacatggtac aatttgcaga tttaagtatt tattacaacc attttctggc 2040
agataacagt ggaacaccct gttctgttaa aattagttta ttatgacaaa ttgcctacag 2100
atggacataa actgtcttga ggaagggcac ctgctttgga ctgaatcgtg tccccccaaa 2160
atcaaatgtt gaagcctaat ctctaatatg atggtatttg gagatggggc ctttgggaga 2220
taactaggtt tagatgaggt caagagtgtg gggccttcct gattagtacc ctgaaaagag 2280
aaaacaccag agagcttgcc ctctctccct cttaccccac aggcacacaa agaggtcatg 2340
tgagtacaca gtgagataac aaccacctat gagaaaacag aagaggcttc agagtgaaat 2400
ctactttgct ggtactgtaa tcttggacat tattctctag aactgtgaga taataaattt 2460
atcttattt 2469

<210> SEQ ID NO 8
<211> LENGTH: 21
<212> TYPE: RNA
<213> ORGANISM: Homo sapiens

<400> SEQUENCE: 8
agaccuggcc cagaccucag c 21

<210> SEQ ID NO 9
<211> LENGTH: 75
<212> TYPE: RNA
<213> ORGANISM: Homo sapiens

<400> SEQUENCE: 9
guggggagcc ugguuagacc uggcccagac cucagcuaca caagcugaug gacugaguca 60
ggggccacac ucucc 75

<210> SEQ ID NO 10
<211> LENGTH: 1037
<212> TYPE: DNA
<213> ORGANISM: Homo sapiens

<400> SEQUENCE: 10
ctgtgggaca gaggaacagg cagagatcag agggcaggct caggttggga ggagtgggga 60
gcctggttag acctggccca gacctcagct acacaagctg atggactgag tcaggggcca 120
cactctccct cctctggtga tgtgacctca gctggtttct tcccactcgg ccatgggttt 180
cccatcctgg agtgggatta agaatccttg tcctggccct gtgcagtggc cacacctgta 240
atcccgacac tttgggaagc ttagatggga gaatccctag gggccaggag ttcaatacca 300
gcctgggcaa catagggaga ccctgtctct acaaaaaaaa tttttaacaa ttagcccggt 360
gtggtggtgt gagcctgtag tcctagctac ttagaggcag atgtgggagg atcacttgag 420
cccagtttga ggctagtcca ggcaacatgg caagatccta tctctaccaa aaatatatat 480
aaacgtgcgt gtgtgtgtgt gtgtgtgtgt gtgtataaat atataaaaga atccttgtcc 540
tgcctgtctc atgggcagct tggaggaaac actgtttttt tgtttttttt ttttttgaga 600
tggagttttg ctcttgttgc ccaggctgga gtgcaatggc acgatctcag ctcaactgca 660
acctccacct cctgggttta agcgattttc ctgcctcatc ctcccgagta gctgagatta 720
caggtgccca ccaccacacc tggctaattt tttgcatttt tagtagagat ggggtttcac 780
catgttggcc aggatggtct cgaactcctg acctcaggtg agccacccca ctcggcctcc 840
cgaagtgctg ggattacagg catgagccac tgcgcccagc ctggaaacac tattgacaag 900
tgaggaggcc tagtccattg agtatcagct agggctacaa acttccaaat cggtgaatca 960
ggtccagaga gggacaagtg ccccagggtt acacaatcat ttgctgaagc agaggttgct 1020
gccatctttg gcctcac 1037

<210> SEQ ID NO 11
<211> LENGTH: 23
<212> TYPE: RNA
<213> ORGANISM: Homo sapiens

<400> SEQUENCE: 11
ggcagguucu cacccucucu agg 23

<210> SEQ ID NO 12
<211> LENGTH: 98
<212> TYPE: RNA
<213> ORGANISM: Homo sapiens

<400> SEQUENCE: 12
guguaguaga gcuaggagga gagggguccug gagaagcgug gaccgguccg gguggguucc 60
ggcagguucu cacccucucu aggccccauu cuccucug 98

<210> SEQ ID NO 13
<211> LENGTH: 1412
<212> TYPE: DNA
<213> ORGANISM: Homo sapiens

<400> SEQUENCE: 13
gtgagggcgg gcgcgggcca gcggccggga agccctaggc caggcccctc ccctgaagga 60
agggcatagg gcgggtcctg cctcaggggg cttgcgagga ccggccaggt tcatctcatg 120
cagcatcaga caaccactat gcagagggat tttatgacgt ttttgaaaaa ttgggaagac 180
aatggtttga cacccacttt gcaggtttag acgaagagat gcgtactgtc aagctggcct 240
gttctctgtc cccgaggcag tcagccagca ccctgcagcc ccgcgccaac cccacactct 300
gctaagccct cgctttgggg cttgagggag acagaccctg cttcgaagga ccctggaggg 360
agggttctgt cctgcttggg ccaggatgcc cagcccctgg ggaccccggg gggacatgct 420
ggaagaagtg gcgaaggaca cgtggccccg tcagccccag acgccgcacg gctgtcctct 480
ccaacaatat cctggtgctg agtgatgact caggcgactc cagcatcagt gattttgttg 540
aagagggcag ctgccagcct cccgacctgc ctgccgggcc ccagctgccc tgccccccaac 600 cccaacccac cccactccac cccctaggcc caggacacat ggccctgtag cgatcccctg 660
gcacgcagac atgggtttta tgtggggagg gacaggctgg gttggcctct gtccccaccc 720
tgagtcctga gcacagaagt aatacggcag ctgtggtaat atctacccag taccctgtgc 780
ctcctcacac ccacgtgacc agccaggcag ggttcaaagc cagcagccaa ggcaggctgg 840
gttggaggta gtgccaggcg taacctgcat tctttccaga ccctacccaa ccctggggcc 900
agtggtggct caagtgagag tgagctccag ctctgagtgg gcatggcagg gctggaccct 960
aaaactggac tccggcagcc ggcaggaccc ctgggacact ccaggcctca gtttccccat 1020
caattcccac ctcctgggga gccgagagtg atagtgtagt agagctagga ggagagggtc 1080
ctggagaagc gtggaccggt ccgggtgggt tccggcaggt tctcaccctc tctaggcccc 1140
attctcctct gcactgtaac atttgaggcc cacgcacaca gtccctcccc aggtctcagg 1200
gttgggcaca gagtagggcc ctgggcaggg atggggggtg gcagtgtctc caacgcccct 1260

```
tccagcctgg actgtgagcc atccaagtgt tggcaaagga ccctgtgctg gatgcccccg   1320

cccggcacac cccactgacc ctccccctgc ccccacccgg cacaccctgc tcaccctgct   1380

caccctgccc ctgcccctgc ccctgcctgc ag                                 1412


<210> SEQ ID NO 14
<211> LENGTH: 6
<212> TYPE: PRT
<213> ORGANISM: Artificial Sequence
<220> FEATURE:
<223> OTHER INFORMATION: synthetic peptide

<400> SEQUENCE: 14

Gly Gly Gly Gly Asp Asp
1               5


<210> SEQ ID NO 15
<211> LENGTH: 8
<212> TYPE: PRT
<213> ORGANISM: Artificial Sequence
<220> FEATURE:
<223> OTHER INFORMATION: synthetic peptide

<400> SEQUENCE: 15

Gly Gly Gly Gly Gly Gly Asp Asp
1               5


<210> SEQ ID NO 16
<211> LENGTH: 10
<212> TYPE: PRT
<213> ORGANISM: Artificial Sequence
<220> FEATURE:
<223> OTHER INFORMATION: synthetic peptide

<400> SEQUENCE: 16

Gly Gly Gly Gly Gly Gly Gly Gly Asp Asp
1               5                   10


<210> SEQ ID NO 17
<211> LENGTH: 12
<212> TYPE: PRT
<213> ORGANISM: Artificial Sequence
<220> FEATURE:
<223> OTHER INFORMATION: synthetic peptide

<400> SEQUENCE: 17

Gly Gly Gly Gly Gly Gly Gly Gly Gly Gly Asp Asp
1               5                   10


<210> SEQ ID NO 18
<211> LENGTH: 7
<212> TYPE: PRT
<213> ORGANISM: Artificial Sequence
<220> FEATURE:
<223> OTHER INFORMATION: synthetic peptide

<400> SEQUENCE: 18

Ala Ala Ala Ala Ala Ala Asp
1               5


<210> SEQ ID NO 19
<211> LENGTH: 8
<212> TYPE: PRT
<213> ORGANISM: Artificial Sequence
<220> FEATURE:
<223> OTHER INFORMATION: synthetic peptide
```

<400> SEQUENCE: 19

Ala Ala Ala Ala Ala Ala Asp Asp
1 5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide

<400> SEQUENCE: 20

Ala Ala Ala Ala Ala Ala Lys
1 5

<210> SEQ ID NO 21
<211> LENGTH: 8
<212> TYPE: PRT
<213> ORGANISM: Artificial Sequence
<220> FEATURE:
<223> OTHER INFORMATION: synthetic peptide

<400> SEQUENCE: 21

Ala Ala Ala Ala Ala Ala Lys Lys
1 5

<210> SEQ ID NO 22
<211> LENGTH: 7
<212> TYPE: PRT
<213> ORGANISM: Artificial Sequence
<220> FEATURE:
<223> OTHER INFORMATION: synthetic peptide

<400> SEQUENCE: 22

Val Val Val Val Val Val Asp
1 5

<210> SEQ ID NO 23
<211> LENGTH: 8
<212> TYPE: PRT
<213> ORGANISM: Artificial Sequence
<220> FEATURE:
<223> OTHER INFORMATION: synthetic peptide

<400> SEQUENCE: 23

Val Val Val Val Val Val Asp Asp
1 5

<210> SEQ ID NO 24
<211> LENGTH: 7
<212> TYPE: PRT
<213> ORGANISM: Artificial Sequence
<220> FEATURE:
<223> OTHER INFORMATION: synthetic peptide

<400> SEQUENCE: 24

Val Val Val Val Val Val Lys
1 5

<210> SEQ ID NO 25
<211> LENGTH: 8
<212> TYPE: PRT
<213> ORGANISM: Artificial Sequence
<220> FEATURE:
<223> OTHER INFORMATION: synthetic peptide

<400> SEQUENCE: 25

Val Val Val Val Val Val Lys Lys
1 5

<210> SEQ ID NO 26
<211> LENGTH: 7
<212> TYPE: PRT
<213> ORGANISM: Artificial Sequence
<220> FEATURE:
<223> OTHER INFORMATION: synthetic peptide

<400> SEQUENCE: 26

Leu Leu Leu Leu Leu Leu Asp
1 5

<210> SEQ ID NO 27
<211> LENGTH: 8
<212> TYPE: PRT
<213> ORGANISM: Artificial Sequence
<220> FEATURE:
<223> OTHER INFORMATION: synthetic peptide

<400> SEQUENCE: 27

Leu Leu Leu Leu Leu Leu Asp Asp
1 5

<210> SEQ ID NO 28
<211> LENGTH: 7
<212> TYPE: PRT
<213> ORGANISM: Artificial Sequence
<220> FEATURE:
<223> OTHER INFORMATION: synthetic peptide

<400> SEQUENCE: 28

Leu Leu Leu Leu Leu Leu Lys
1 5

<210> SEQ ID NO 29
<211> LENGTH: 8
<212> TYPE: PRT
<213> ORGANISM: Artificial Sequence
<220> FEATURE:
<223> OTHER INFORMATION: synthetic peptide

<400> SEQUENCE: 29

Leu Leu Leu Leu Leu Leu Lys Lys
1 5

<210> SEQ ID NO 30
<211> LENGTH: 19
<212> TYPE: RNA
<213> ORGANISM: Artificial Sequence
<220> FEATURE:
<223> OTHER INFORMATION: synthetic RNA

<400> SEQUENCE: 30
uucuccgaac gugucacgu 19

<210> SEQ ID NO 31
<211> LENGTH: 19
<212> TYPE: RNA
<213> ORGANISM: Artificial Sequence
<220> FEATURE:
<223> OTHER INFORMATION: synthetic RNA

<400> SEQUENCE: 31

-continued

```
acgucacacg uucggagaa                                         19


<210> SEQ ID NO 32
<211> LENGTH: 22
<212> TYPE: RNA
<213> ORGANISM: Artificial Sequence
<220> FEATURE:
<223> OTHER INFORMATION: synthetic RNA

<400> SEQUENCE: 32

uaccugaauu cccaaaagcu uu                                     22
```